United States Patent
Gilligan et al.

(10) Patent No.: US 11,279,913 B2
(45) Date of Patent: Mar. 22, 2022

(54) SPERM PROCESSING METHOD, APPARATUS AND RELATED MEDIA COMPOSITIONS

(71) Applicant: Inguran, LLC, Navasota, TX (US)

(72) Inventors: Thomas B. Gilligan, College Station, TX (US); Clara Gonzalez-Marin, College Station, TX (US); Ramakrishnan Vishwanath, Hamilton (NZ)

(73) Assignee: Inguran, LLC, Navasota, TX (US)

( * ) Notice: Subject to any disclaimer, the term of this patent is extended or adjusted under 35 U.S.C. 154(b) by 0 days.

(21) Appl. No.: 15/875,679

(22) Filed: Jan. 19, 2018

(65) Prior Publication Data

US 2018/0208894 A1    Jul. 26, 2018

Related U.S. Application Data

(60) Provisional application No. 62/448,829, filed on Jan. 20, 2017, provisional application No. 62/584,557, filed on Nov. 10, 2017.

(51) Int. Cl.
*C12N 5/071* (2010.01)
*A01N 1/02* (2006.01)

(52) U.S. Cl.
CPC ......... *C12N 5/0612* (2013.01); *A01N 1/0205* (2013.01); *A01N 1/0215* (2013.01); *A01N 1/0221* (2013.01); *A01N 1/0226* (2013.01)

(58) Field of Classification Search
None
See application file for complete search history.

(56) References Cited

U.S. PATENT DOCUMENTS

| | | | |
|---|---|---|---|
| 3,185,623 A | 5/1965 | Smith et al. | |
| 5,135,759 A | 8/1992 | Johnson | |
| 9,140,688 B2 * | 9/2015 | Evans | G01N 33/5005 |
| 9,347,038 B2 * | 5/2016 | Lenz | A01N 1/0226 |
| 2006/0121440 A1 | 6/2006 | Schenk et al. | |
| 2007/0099171 A1 | 5/2007 | Schenk et al. | |
| 2013/0183656 A1 | 7/2013 | Lenz et al. | |
| 2014/0099627 A1 | 4/2014 | Gilligan et al. | |
| 2016/0145568 A1 | 5/2016 | Gilligan et al. | |

FOREIGN PATENT DOCUMENTS

| | | |
|---|---|---|
| RU | 2605616 C1 | 11/2015 |
| WO | 99/33956 A1 | 7/1999 |
| WO | 2001/37655 A1 | 5/2001 |
| WO | 2001/85913 A2 | 11/2001 |
| WO | 2004088283 A2 | 10/2004 |
| WO | 2004/104178 A1 | 12/2004 |
| WO | 2005/095960 A1 | 10/2005 |
| WO | 2010/021627 A1 | 2/2010 |
| WO | 2011/097032 A1 | 8/2011 |
| WO | 2011/123166 A2 | 10/2011 |
| WO | 2012/167151 A1 | 12/2012 |
| WO | 2013/049631 A1 | 4/2013 |

OTHER PUBLICATIONS

Salamon et al, "Storage of Raw semen" Animal Reproduction Science, 2000, vol. 62, pp. 77-111. (Year: 2000).*
Russian Office Action dated Oct. 4, 2019 in related RU Appl. No. 2019125565.
Drevuis, L.-O. "Permeability Coefficients of Bull Spermatozoa for Water and Polyhydric Alcohols." Experimental Cell Research 69 (1971) 212-216.
Ahluwalia et al. "Free Carbohydrates in Seminal Plasma and Sperm Cells of Semen of Fowl." J. Reprod. Fert. (1966) 12, 359-361.
Wilmut et a. "The Low Temperature Preservation of Boar Spermatozoa. 1. The Motility and Morphology of Boar Spermatozoa Frozen and Thawed in the Presence of Permeating Protective Agents." Cryobiology 14, 471-478 (1977).
Kim et al. "Antioxidant Effect of Erythritol on Boar Spermatozoa During Cryopreservation." Program/Abstract # 306. Society for Developmental Biology 70th Annual Meeting Jul. 21-25, 2011.
Visser et al. "Effect of Composition of Tris-based Diluent on Survival of Boar Spermatozoa following Deep Freezing." Aust. J. Biol. Sci., 1974, 27, 485-97.
Drevuis, L.-O. "Bull Spermatozoa as Osmometers." J. Reprod. Fert. (1972) 28, 29-39.
Clark et al. "D-Mannitol, Erythritol and Glycerol in Bovine Semen." J. Reprod. Fert. (1967) 13, 189-197.
Bucak et al. "Effects of Curcumin and Dithioerythritol on Frozen-Thawed Bovine Semen." Andrologia 2012, 44, 102-109.
White, I G. "Metabolism of Glycerol and Similar Compounds by Bull Spermatozoa." American Journal of Physiology. vol. 189 No. 2. 1957.
Utsumi et al. "Cryoprotective Effect of Polyols on Rat Embryos during Two-Step Freezing." Cryobiology 29, 332-341 (1992).
Miyamoto et al. "Survival of Mouse Embryos After Freezing and Thawing in the Presence of Erythritol." The Journal of Experimental Zoology 216:337-340 (1981).
Kasai et al. "Effects of Various Cryoprotective Agents on the Survival of Unfrozen and Frozen Mouse Embryos." J. Reprod. Fert. (1981) 63, 175-180.
Miyamoto et al. "Survival of Mouse Embryos Frozen-Thawed Slowly or Rapidly in the Presence of Various Cryoprotectants." The Journal of Experimental Zoology 226:123-127 (1983).

(Continued)

*Primary Examiner* — Allison M Fox
(74) *Attorney, Agent, or Firm* — Ryan Christensen; Hashim Rahman

(57) ABSTRACT

Embodiments of the present invention relate generally to processes, systems, and compositions useful in manipulating a ratio of viable X chromosome bearing sperm to viable Y chromosome bearing sperm in at least one sperm population and useful for preserving the resulting manipulated sperm population. In some embodiments a cryoprotectant may be incorporated into various medias used in manipulating the sperm sample, such as in a staining media, a sheath fluid, and a collection media.

30 Claims, 34 Drawing Sheets

(56) References Cited

OTHER PUBLICATIONS

Miyamoto et al. "Liquid Nitrogen Vapour Freezing of Mouse Embryos." J. Reprod. Fert. (1986) 78,471-478.
Turner et al. "Stereochemical Arrangement of Hydroxyl Groups in Sugar and Polyalcohol Molecules as an Important Factor in Effective Cryopreservation." Plant Science 160 (2001) 489-497.
Verberckmoes et al. "Comparison of Three Diluents for the Storage of Fresh Bovine Semen." Theriogenology 63 (2005) 912-922.
Verberckmoes et al. "Corrigendum to Comparison of Three Diluents for the Storage of Fresh Bovine Semen." Theriogenology 66 (2006) 2219.
Gertjan et al. "Erythritol is a Sweet Antioxidant." Nutrition (2009) 1-10.
Wilson, D E. and Reeder, D.M., Mammal Species of the World, Smithsonian Institution Press, (1993).
International Search Report and Written Opinion dated Jun. 14, 2018 in related PCT Appl. No. PCT/US18/14474.
Canadian Examination Report dated May 25, 2020 in related CA Appl. No. 3,049,264.
Extended European Search Report dated Aug. 10, 2020 in related EP Appl. No. 18742360.3.
Russian Office Action dated Jun. 17, 2020 in related RU Appl. No. 2019125565.
Russian Office Action dated Nov. 16, 2020 in related RU Appl. No. 2019125565.
Russian Examination Report dated Apr. 13, 2021 in related RU Appl. No. 2019125565.
New Zealand Examination Report dated May 13, 2021 in related NZ Appl. No. 755215.
New Zealand Examination Report dated Jul. 29, 2021 in related NZ Appl. No. 755215.

* cited by examiner

FIG. 2
FIG. 3
FIG. 4
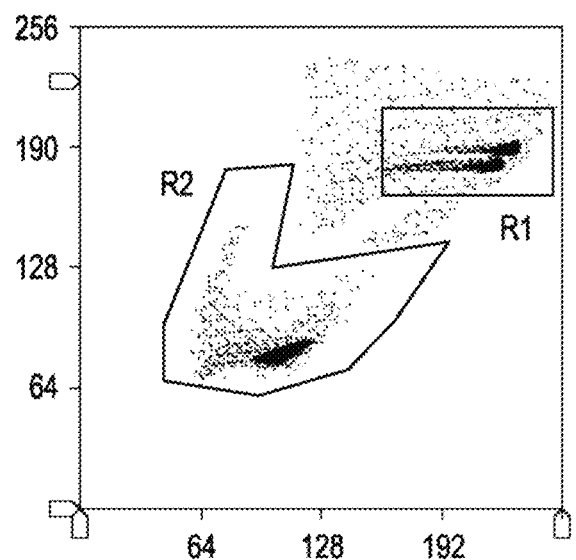
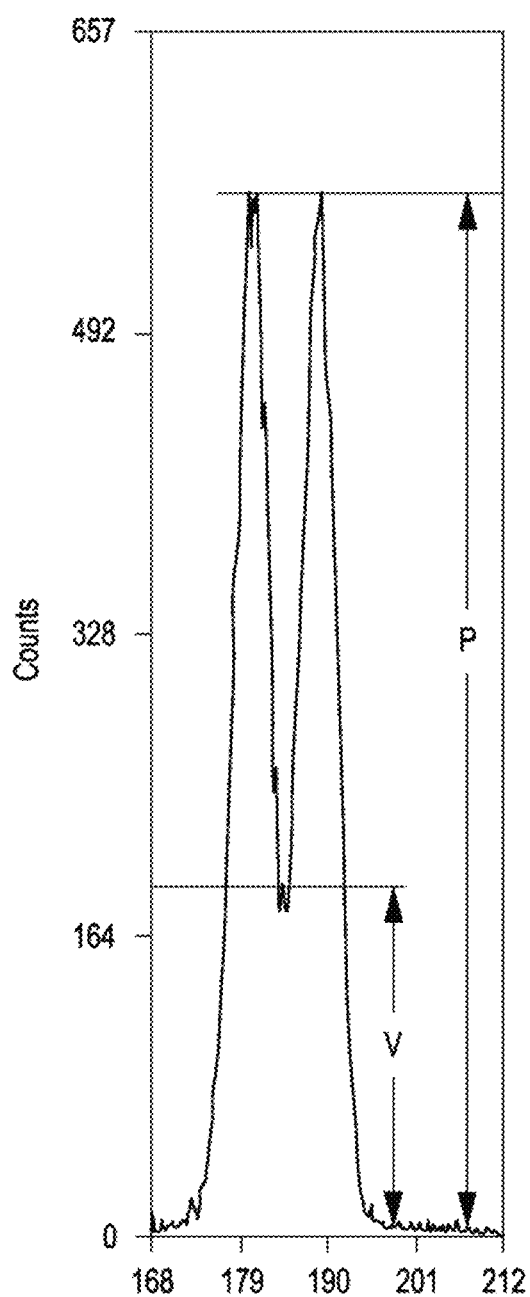
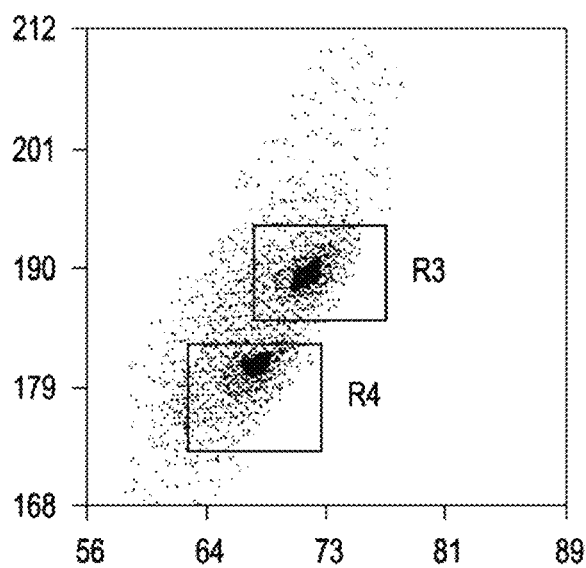

GDL % PVR (Average of 3 bulls):

FIG. 13

Post-thaw QC (average of 10 bulls):

| Motility | | IVOS | | | | A. Sorter | | | |
|---|---|---|---|---|---|---|---|---|---|
| | | 0 h | | 3 h | | 0 h | | 3 h | |
| 0 Hour | 3 Hour | MOTILE | PROG | MOTILE | PROG | Viable | PIA | Viable | PIA |
| CONTROL 54 | 50 | 52.1 | 38.9 | 46.7 | 24.5 | 44.6 | 76.1 | 38.4 | 64.4 |
| T1 55 | 48 | 52.2 | 42.3 | 45.1 | 27.0 | 47.6 | 79.6 | 38.1 | 68.0 |
| T2 54 | 43 | 55.2 | 44.4 | 44.6 | 21.2 | 48.7 | 79.7 | 42.7 | 69.1 |
| T3 55 | 48 | 55.6 | 41.4 | 47.8 | 28.7 | 50.1 | 81.9 | 43.4 | 72.3 |
| T4 55 | 41 | 57.9 | 45.8 | 38.6 | 22.7 | 47.6 | 81.2 | 41.4 | 70.1 |

FIG. 14

| | Convergence | | | | |
|---|---|---|---|---|---|
| | Visual | IVOS | | A. Sorter | |
| | Motility | MOTILE | PROGRESIVE | Viable | PIA |
| CONTROL | 92% | 90% | 63% | 86% | 85% |
| T1 | 86% | 86% | 64% | 80% | 85% |
| T2 | 78% | 81% | 48% | 88% | 87% |
| T3 | 87% | 86% | 69% | 87% | 88% |
| T4 | 75% | 67% | 50% | 87% | 86% |

Post-thaw QC (average of 4 bulls) – 0 h:

Post-thaw QC (average of 4 bulls) – 3 h:

FIG. 26
Post-thaw QC (average of 4 bulls) – 3 h:
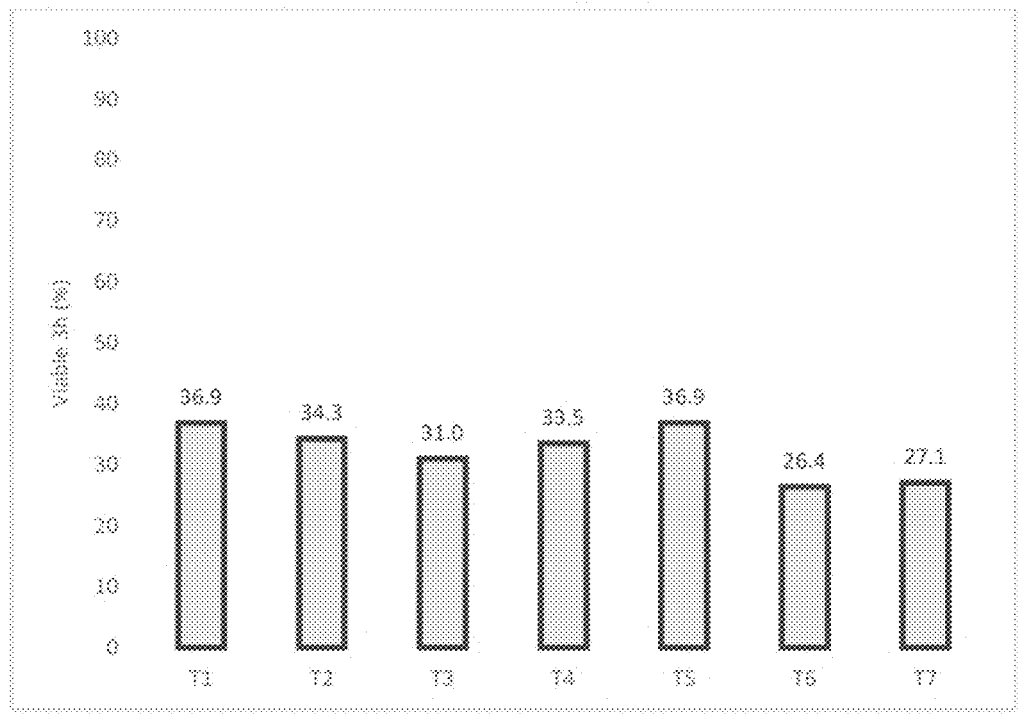
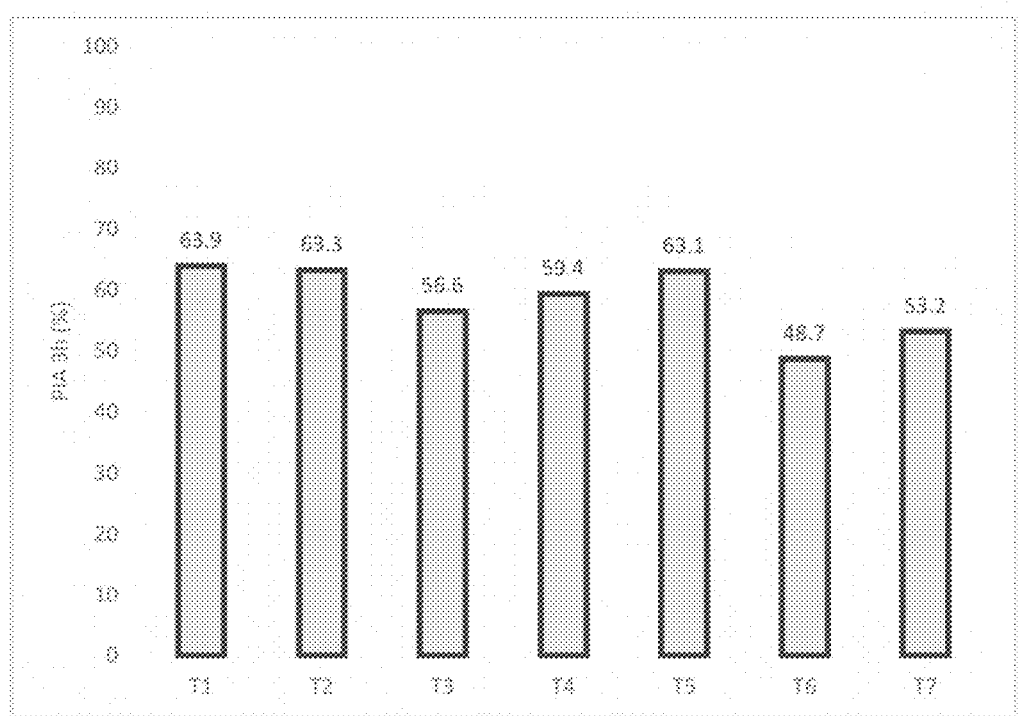

FIG. 27
Post-thaw QC (average of 4 bulls) – Convergence:
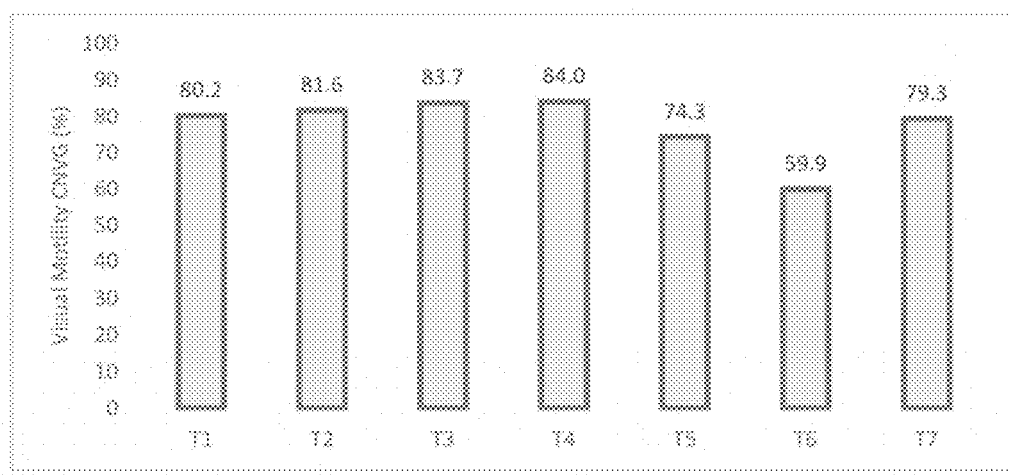
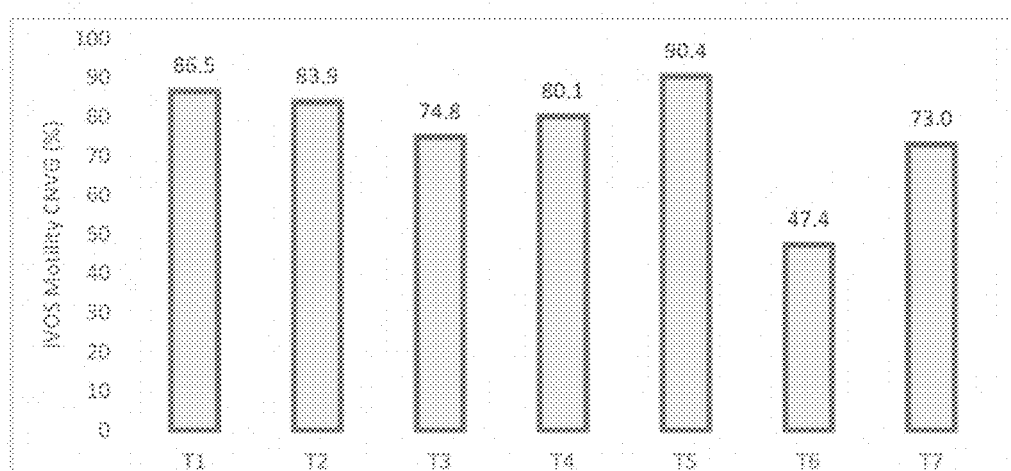
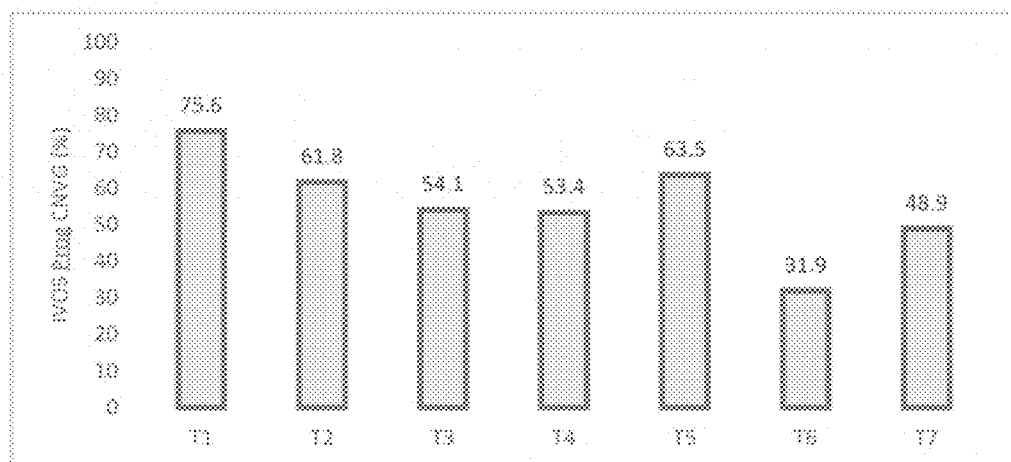

FIG. 28
Post-thaw QC (average of 4 bulls) – Convergence:
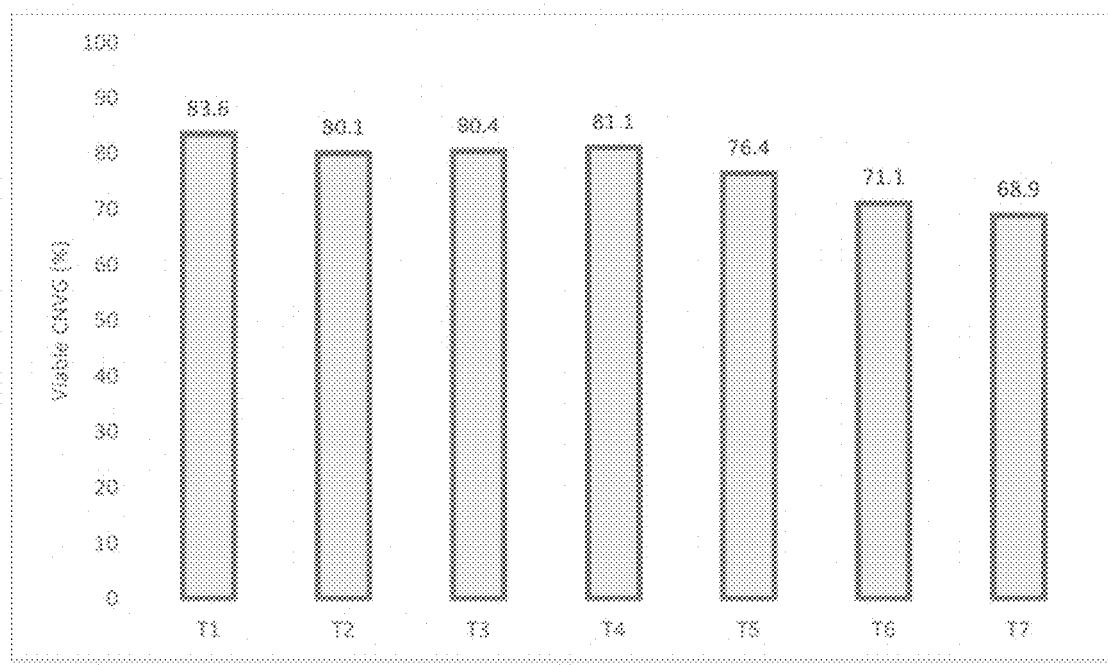
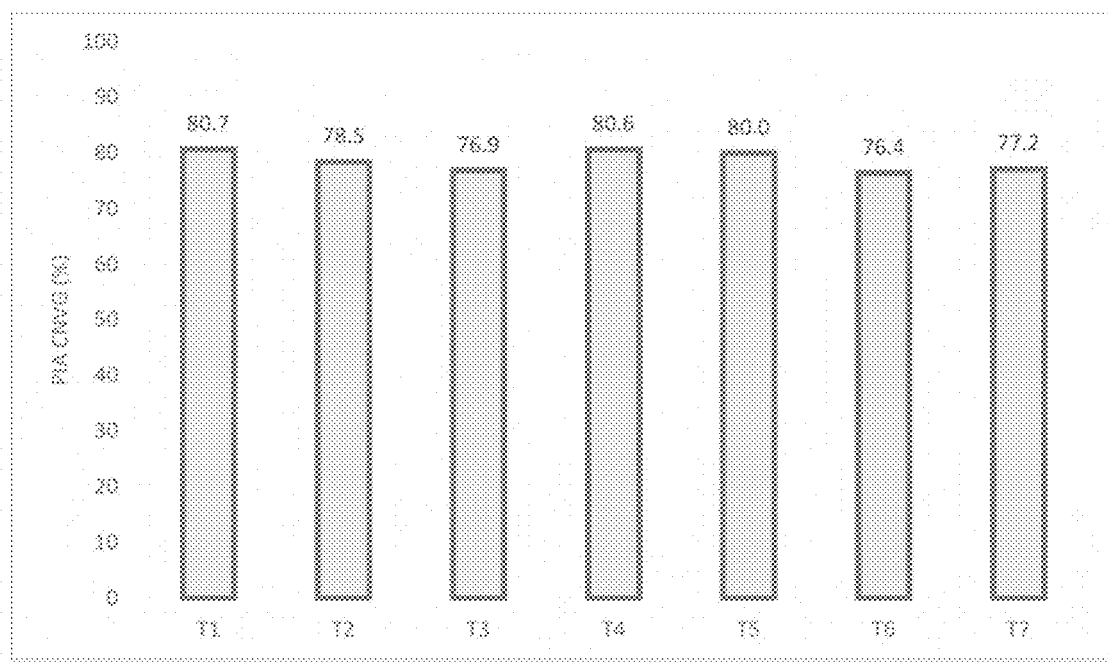

FIG. 29
Post-thaw QC (average of 10 bulls) – 0h:
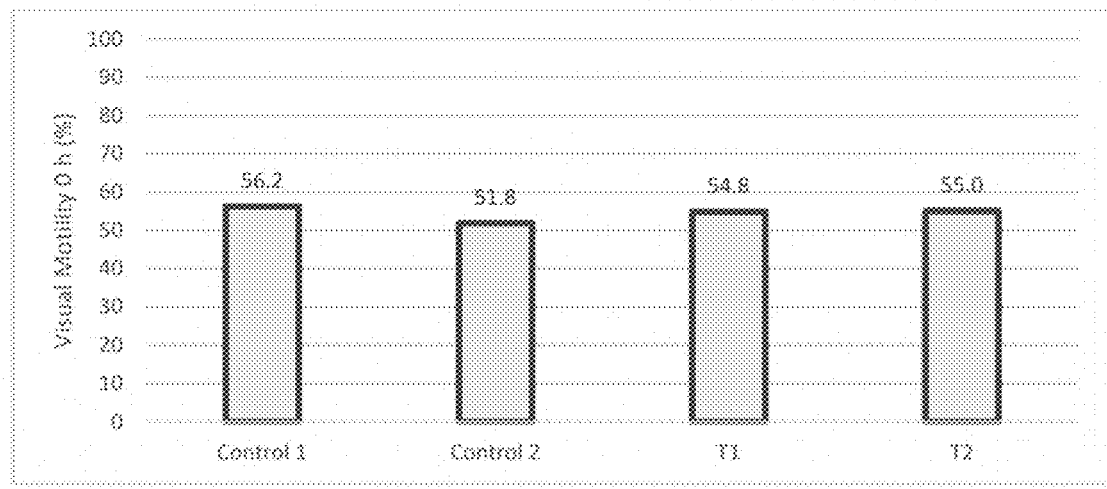
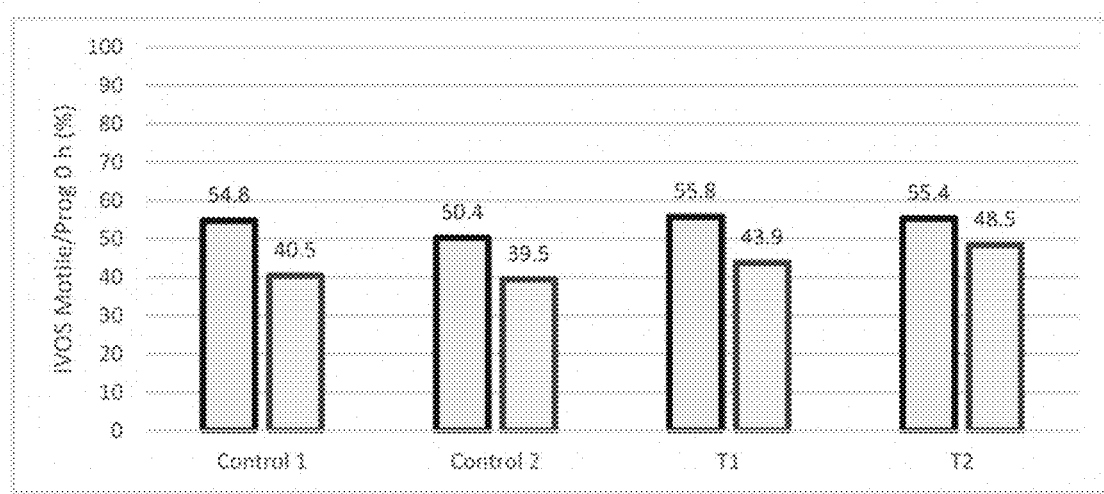
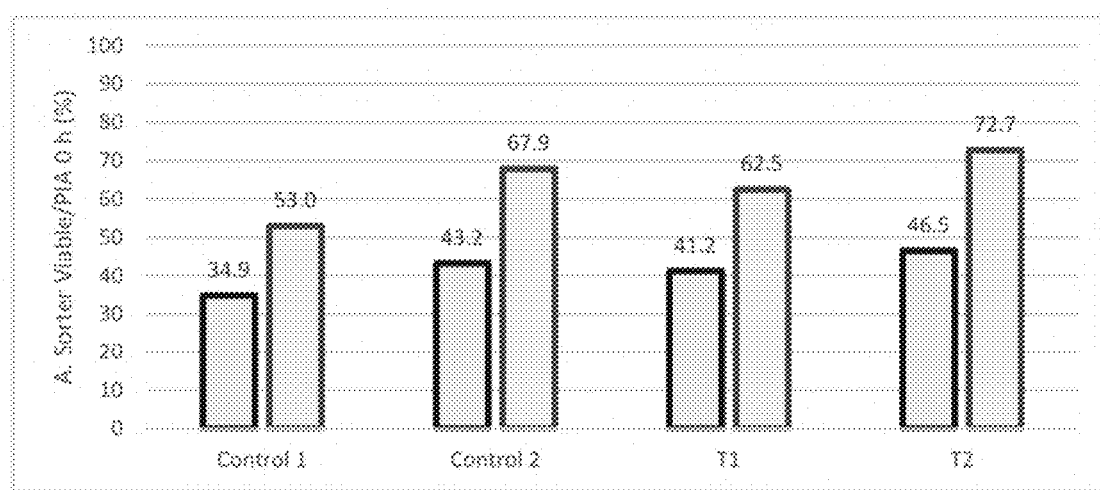

FIG. 32

IVF summary:

|  | OOCYTES # | CLEAVED # | % | EMBRYOS PRODUCED | % | FREEZABLE | % |
|---|---|---|---|---|---|---|---|
| Bull1 Rep1 Control | 187 | 125 | 66.8% | 62 | 33.2% | 40 | 64.5% |
| Bull1 Rep2 Control | 190 | 136 | 71.6% | 68 | 35.8% | 40 | 58.8% |
|  | 377 | 261 | 69.2% | 130 | 34.5% | 80 | 61.5% |
| Bull2 Rep1 Control | 189 | 138 | 73.0% | 63 | 33.3% | 36 | 57.1% |
| Bull2 Rep2 Control | 187 | 101 | 54.0% | 48 | 25.7% | 22 | 45.8% |
|  | 376 | 239 | 63.6% | 111 | 29.5% | 58 | 52.3% |
| Bull3 Rep1 Control | 186 | 130 | 69.9% | 37 | 19.9% | 13 | 35.1% |
| Bull3 Rep2 Control | 186 | 124 | 66.7% | 28 | 15.1% | 10 | 35.7% |
|  | 372 | 254 | 68.3% | 65 | 17.5% | 23 | 35.4% |
|  | 1125 | 754 | 67.0% | 306 | 27.2% | 161 | 52.6% |

|  | OOCYTES # | CLEAVED # | % | EMBRYOS PRODUCED | % | FREEZABLE | % |
|---|---|---|---|---|---|---|---|
| Bull1 Rep1 3% glycerol | 187 | 126 | 67.4% | 57 | 30.5% | 36 | 63.2% |
| Bull1 Rep2 3% glycerol | 179 | 137 | 76.5% | 63 | 35.2% | 39 | 61.9% |
|  | 366 | 263 | 71.9% | 120 | 32.8% | 75 | 62.5% |
| Bull2 Rep1 3% glycerol | 185 | 139 | 75.1% | 61 | 33.0% | 39 | 63.9% |
| Bull2 Rep2 3% glycerol | 190 | 106 | 55.8% | 48 | 25.3% | 25 | 52.1% |
|  | 375 | 245 | 65.3% | 109 | 29.1% | 64 | 58.7% |
| Bull3 Rep1 3% glycerol | 183 | 134 | 73.2% | 45 | 24.6% | 13 | 28.9% |
| Bull3 Rep2 3% glycerol | 174 | 128 | 73.6% | 33 | 19.0% | 10 | 30.3% |
|  | 357 | 262 | 73.4% | 78 | 21.8% | 23 | 29.5% |
|  | 1098 | 770 | 70.1% | 307 | 28.0% | 162 | 52.8% |

|  | Production QC | | R&D QC | | | | | |
| --- | --- | --- | --- | --- | --- | --- | --- | --- |
| Treatment | 3H Mot | 3 H PIA | 0H Mot | 3H Mot | CNVG | 0H Viable | 3H Viable | 0H PIA |
| Control | 57 | 75 | 62 | 44 | 73% | 51.5 | 42.2 | 79.3 |
| 3% Glycerol + AKG SF | 60 | 76 | 62 | 46 | 75% | 45.1 | 35.7 | 79.9 |

Fig. 33

631 is equal to Control 635 is equal to Glycerol Sheath Fluid

SPERM PROCESSING METHOD, APPARATUS AND RELATED MEDIA COMPOSITIONS

TECHNICAL FIELD

Generally, this disclosure relates to processing sperm, and more particularly relates to processes, systems, and compositions useful in manipulating a ratio of viable X chromosome bearing sperm to viable Y chromosome bearing sperm in at least one sperm population and useful for preserving the resulting manipulated sperm population.

BACKGROUND

Chromosomal content of male haploid gametes determine the sex of mammalian offspring. More specifically, fertilization of an oocyte with a Y-chromosome bearing sperm yields male offspring and fertilization with an X-chromosome bearing sperm yields female offspring. While a number of technologies have been investigated for predetermining the sex of mammalian offspring, only the flow cytometric sorting enjoys widespread commercial acceptance.

Flow cytometers modified for sperm sorting detect relative differences in the DNA content of X-chromosome bearing sperm and Y-chromosome bearing sperm. In order to measure the DNA content of sperm, a sperm population is generally stoichiometrically stained with a DNA selective fluorescent dye that binds to nuclear DNA. One such DNA selective fluorescent dye, Hoechst 33342, sometimes referred to as Hoechst bisbenzimide 33342, can be used in sufficient quantities to differentiate small variations in nuclear DNA without exhibiting the toxicity of other dyes.

These relative differences between X-chromosome bearing sperm and Y-chromosome bearing sperm are typically small variations. In bovine, for example, Holstein bulls have about a 3.8% difference in DNA content, while Jersey bulls have about a 4.1% difference. Due to the inexact nature of stoichiometric DNA staining, these small differences are difficult to ascertain. Sperm samples, even samples within a single breed, may vary a great deal in concentration, pH, motilities and morphologies. As such, staining conditions that worked well in one circumstance may understain or overstain other sperm samples, even sperm samples collected from the same breed, or even from the same animal. The shape of sperm create additional difficulties in differentiating X-chromosome from Y-chromosome bearing cells. In particular, sperm heads, which contain the nuclear DNA, are roughly paddle-like shape in most species. This geometry presents an additionally confounding effect by producing different levels of fluorescent emissions at different angles and these differences outweigh the detectable differences in X and Y chromosome bearing sperm. Most sperm sorting flow cytometers include a side detector to determine sperm orientation and an orienting nozzle to provide sperm with a more uniform orientation.

Despite these difficulties, Hoechst 33342 can be used in non-toxic concentrations. Unfortunately, the staining process is damaging to non-regenerative, time critical cells. In particular, uniform staining with Hoechst 33342 requires incubation at elevated temperatures and elevated pHs and both elevating sperm temperature and elevating sperm pH contribute to sperm damage. Once stained, the pressure experienced by sperm in a flow cytometer may present additional damage to sperm, and the associated shear forces may present more damage.

The limited life span of sperm frequently necessitates freezing for storage and shipment. Intracellular fluids, including water, are removed from the cell during this process to reduce the volume of intracellular fluids that freeze. Otherwise, intracellular fluids would crystallize and expand from their liquid volume. This expansion causes intracellular stress and mechanical damage to the sperm and reduces sperm fertility. A number of cryoprotectants may be suitable for this purpose, the most common of which is glycerol. Even glycerol, however, presents a number of drawbacks. For example, glycerol poses at least a degree of toxicity to sperm, the effect of which may become more pronounced with larger amounts of glycerol. Further, glycerol may be hyperosmotic to sperm, which may result in a degree of shock to sperm to which glycerol has been added. Such hyperosmotic properties may cause a sperm coming into contact with glycerol to rapidly shrink or expand as a result of a difference in solute concentration across the sperm's cell membrane. Such rapid shrinking and expanding may cause damage to the sperm. This toxicity and damage may have a compounding effective, particularly for sorted sperm which have suffered through the injurious staining and sorting steps.

In most commercial settings, however, the benefit of freezing sorted sperm generally outweighs the negative impact of damage caused and certain procedures have been developed to minimize the adverse effects of glycerol on sperm. As one example, glycerol may be combined with sperm at reduced temperatures to mitigate the toxic effects of glycerol on the sperm. For this purpose, extenders or other media incorporating glycerol may be prepared in a multiple step process involving two or more extender fractions. In particular, sperm extenders may comprise an "A" fraction without glycerol and a "B" fraction with glycerol. The "A" and "B" fractions allow a sperm extender to be introduced in two or more steps, for example, a first step in which A fraction is added to the sperm, such as sex selected sperm, which may be at room temperature, followed by a second step in which the sperm and the A fraction are cooled to a lower temperature, and the B fraction containing glycerol added at such a lower temperature. Moreover, to reduce the hyperosmotic effects of glycerol on sperm cells, the B fraction may be added in multiple steps, possibly so as to reduce the shock to sperm cells by subjecting sperm cells to lowered amounts of glycerol at each added glycerol step. As described in International Application WO/200137655, for example, the extended sperm may be reconcentrated by centrifugation and suspension in a freezing extender, sometimes called an "AB" extender which has half the glycerol content of the "B" fraction.

SUMMARY OF THE INVENTION

Certain embodiments of the claimed invention are summarized below. These embodiments are not intended to limit the scope of the claimed invention, but rather serve as brief descriptions of possible forms of the invention. The invention may encompass a variety of forms which differ from these summaries.

One broad embodiment described herein relates to the composition of a sperm staining media that includes a buffer, a DNA selective dye; and a cryoprotectant. The cryoprotectant can be a sugar alcohol, such as, ethylene glycol; glycerol; erythritol; threitol; arabitol; ribitol; xylitol; sorbitol; galactitol; iditol; volemitol; fucitol; inositol; a glycylglycitol, or any combination of sugar alcohols. Alternatively, the cryoprotectant can be a glycol, such as propylene glycol, butane triol or a combinations thereof. The cryoprotectant in the staining media may have a volume/volume (vol./vol.) concentration between about 0.1% and about 1%; between about 1% and about 2%; between about 2% and about 3%; between about 3% and about 4%; between about 2% and about 4%; or between about 1.5% and about 3%. The buffer can be anyone of HEPES ((4-(2-hydroxyethyl)-1-piperazineethanesulfonic acid)), sodium bicarbonate, MOPS ((3-(N-morpholino)propanesulfonic acid)), TRIS (tris(hydroxymethyl)aminomethane), TES (2-[[1,3-dihydroxy-2-(hydroxymethyl)propan-2-yl]amino]ethanesulfonic acid), TALP (Tyrode's Albumen Lactate Pyruvate), TCA (trichloroacetic acid), PBS (phosphate buffered saline), milk, derivatives thereof or combinations thereof. The DNA selective dye can be a DNA selective fluorescent dye such as Hoechest 33342, which may be supplied at a concentration between about 10 μM and about 200 μM, between about 20 μM and about 100 μM, between about 30 μM and about 70 μM. The sperm staining media can comprise an incubated sperm media composition incubated at a temperature between about 30° C. and about 39° C., between about 32° C. and about 37° C., or at about 34° C.

Another broad embodiment of the invention described herein relates to a method of processing sperm in which cryoprotectant is introduced at earlier stages than previously contemplated. Sperm sample having viable X-chromosome bearing sperm to viable Y-chromosome bearing sperm is stained with a staining media and contacted with a sheath fluid in a flow path. The staining media and/or the sheath fluid include a cryoprotectant. The method can continue by manipulating the ratio of viable X-chromosome bearing sperm to viable Y-chromosome bearing sperm in the sperm sample to form at least one manipulated sperm population. Certain embodiments can further include the step of collecting the manipulated sperm population in a collection media, sometimes referred to as a catch fluid or a collection fluid. In some embodiments each of the staining media, the sheath fluid and the collection media include an amount of cryoprotectant. Certain embodiments can further include the step of cryopreserving/freezing the manipulated sperm sample. The cryoprotectant can be a polyalcohol, low molecular weight amide, or methylamide; in one embodiment the polyalcohol is a sugar alcohol, such as, ethylene glycol; glycerol; erythritol; threitol; arabitol; ribitol; xylitol; sorbitol; galactitol; iditol; volemitol; fucitol; inositol; a glycylglycitol, or any combination of sugar alcohols. In another embodiment the polyalcohol can be a glycol, such as propylene glycol, butane triol or combinations thereof.

When present in the staining media, the cryoprotectant may have a vol./vol. or weight/volume (wt./vol.) concentration between about 0.1% and about 1%; between about 1% and about 2%; between about 2% and about 3%; between about 4% and about 5%; between about 2% and about 4%; about 1%, 2%, 3%, 4%, 5%; or between about 1.5% and about 3%.

When present in the sheath fluid, the cryoprotectant may have a vol./vol. or wt./vol. concentration between about 0.1% and about 6%; between about 0.1% and about 2%; between about 2% and about 4%; between about 4% and about 6%; between about 1% and about 2%; between about 2% and about 3%; about 3%; between about 3% and about 4%; between about 4% and about 5%; between about 5% and about 6%; between about 2% and about 6%; about 1%, 2%, 3%, 4%, 5%; or between about 3% and about 5%. When present in the collection media, the cryoprotectant may have a vol./vol. or wt./vol. concentration between about 1% and about 2% cryoprotectant by volume; between about 2% and about 4% cryoprotectant by volume; between about 4% and about 6% cryoprotectant by volume; between about 3% and about 5% cryoprotectant by volume; about 1%, 2%, 3%, 4%, or 5% cryoprotectant by volume; between about 3.5% and about 5.5% cryoprotectant by volume, or at about 4.5% concentration by volume.

In certain embodiments of the broad method, cryoprotectant may be added in more than one of the staining media, sheath fluid, collection media. The cryoprotectant may be present in differing amounts in each of the staining media, sheath fluid, collection media. In one embodiment, the concentration of cryoprotectant is increased, when present, at each subsequent step in which cryoprotectant is present. Similarly, in embodiments in which the manipulated sperm sample is extended in a freezing extender for freezing, and where cryoprotectant has been added in more than one of the staining media, sheath fluid, collection media the cryoprotectant may present in the freezing extender at a vol./vol. or wt./vol.concentration less than 6%. In such an embodiment, the cryoprotectant may be present in the freezing extender at a vol./vol. or wt./vol. concentration between about 1% and about 6%, between about 3% and about 5%, between about 3.5% and about 5.5%, about 3.5%, between about 4% and about 5%, or at a concentration of about 4.5%.

One broad embodiment described herein relates a system for manipulating a sperm sample in the presence of a cryoprotectant. The system includes a sample source containing a sperm sample and a sheath source containing sheath fluid having a cryoprotectant additive. A fluid delivery structure forms a coaxial flow of sperm sample from the sample source surrounded by sheath fluid from the sheath fluid source and directs the coaxial flow through an interrogation location. A source of electromagnetic radiation illuminates sperm at the interrogation location and at least one detector generates signals in response to such illumination. An analyzer determines sperm characteristics based on the signals produced by the at least one detector.

In some embodiments of the system for manipulating a sperm sample the fluid delivery structure comprises a nozzle, such as an orienting nozzle. While in other embodiments the fluid delivery structure comprises a flow channel, such as in a cuvette or in a microfluidic chip. Some embodiments of the system include the necessary components for forming, charging and deflecting droplets from the coaxial flow, while in other embodiments, photo-damaging (i.e. ablation) laser damages selected sperm in the coaxial flow.

The cryoprotectant present in the sheath fluid if such a system can be a sugar alcohol, such as, ethylene glycol; glycerol; erythritol; threitol; arabitol; ribitol; xylitol; sorbitol; galactitol; iditol; volemitol; fucitol; inositol; a glycylglycitol, or any combination of sugar alcohols. Alternatively, the cryoprotectant can be a glycol, such as propylene glycol, butane triol or combinations thereof. The cryoprotect and may be present in the sheath fluid at a vol./vol. or wt./vol. concentration between about 0.1% and about 6%; between about 0.1% and about 2%; between about 2% and about 4%; between about 4% and about 6%; between about 1% and about 2%; between about 2% and about 3%; between about 3% and about 4%; between about 4% and about 5%; between about 5% and about 6%; between about 2% and about 6%; or between about 3% and about 5%.

Still another broad embodiment described herein relates to a method of processing sperm in which cryoprotectant is introduced at earlier stages than previously contemplated. Sperm sample having viable X-chromosome bearing sperm to viable Y-chromosome bearing sperm is stained with a staining media having a DNA select dye and injected into a flow of sheath fluid. Stained sperm in the sperm sample are then exposed to an electromagnetic radiation source that causes a detectable response in the DNA selective dye. The detectable response of the DNA selective dye is then detected and a ratio of viable X-chromosome bearing sperm to viable Y-chromosome bearing sperm is manipulated to form at least one manipulated sperm population. The at least one manipulated sperm population is collected in one or more collection vessels having collection medias therein. In this broad method one or more of the staining media, sheath fluid and collection media includes a cryoprotectant.

The cryoprotectant can be a sugar alcohol, such as, ethylene glycol; glycerol; erythritol; threitol; arabitol; ribitol; xylitol; sorbitol; galactitol; iditol; volemitol; fucitol; inositol; a glycylglycitol, or any combination of sugar alcohols. Alternatively, the cryoprotectant can be a glycol, such as propylene glycol, butane triol or combinations thereof.

When present in the staining media, the cryoprotectant may have a vol./vol. or wt./vol. concentration between about 0.1% and about 1%; between about 1% and about 2%; between about 2% and about 3%; between about 4% and about 5%; between about 2% and about 4%; or between about 1.5% and about 3%.

When present in the sheath fluid, the cryoprotectant may have a vol./vol. or wt./vol. concentration less than 6%; less than 5%; less than 4%; less than 3%; less than 2%; less than 1%; between about 0.1% and about 6%; between about 0.1% and about 2%; between about 2% and about 4%; between about 4% and about 6%; between about 1% and about 2%; between about 2% and about 3%; between about 3% and about 4%; between about 4% and about 5%; between about 5% and about 6%; between about 2% and about 6%; or between about 3% and about 5%.

Similarly, when present in the collection media, the cryoprotectant may have a vol./vol. or wt./vol. concentration between about 1% and about 2%; between about 2% and about 4%; between about 4% and about 6%; between about 3% and about 5%; between about 3.5% and about 5.5%; or at a concentration of about 4.5.

The cryoprotectant may be present in differing amounts in each of the staining media, sheath fluid, collection media. In one embodiment, the concentration of cryoprotectant is increased, when present, at each subsequent step in which cryoprotectant is present.

In embodiments in which the manipulated sperm sample is extended in a freezing extender for freezing, and where cryoprotectant has been added in more than one of the staining media, sheath fluid, collection media the cryoprotectant may present in the freezing extender at a vol./vol. or wt./vol. concentration less than 6%. In such an embodiment, the cryoprotectant may be present at a concentration between 1% and 6%, between 3.5% and 5.5%, between 4% and 5%, or at a concentration of about 4.5%.

Yet another broad embodiment described herein relates to a method of freezing/cryopreserving a population of manipulated sperm collected as a mixture which includes a cryoprotectant. One such embodiment comprises contacting a stained sperm sample with a sheath fluid in a flow path; manipulating a ratio of viable X-chromosome bearing sperm to viable Y-chromosome bearing sperm to form at least one manipulated sperm population; collecting the manipulated sperm sample in the presence of a cryoprotectant; concentrating the collected sperm sample; resuspending the concentrated sperm sample in a freezing extender; and freezing the resuspended sperm sample. The method may further comprise the step of cooling sperm for a period of less than 90 minutes. Additionally, the step of collecting a mixture further comprises: collecting the mixture in a container that contains between about 5 ml and about 50 ml of collection media. In certain embodiments, the step of collecting a mixture further comprises collecting a sorted sperm sample from a flow cytometer until the container is filled to between about 60% to about 90% of the containers capacity. In further embodiments, the step of concentrating the collected mixture is performed in the container. In yet a further embodiment, the step of concentrating the collected sperm sample directly follows the step of collecting the manipulated sperm sample in the presence of a cryoprotectant without any further dilution occurring between the steps. The freezing extender in this embodiment may comprise less than 6% vol./vol. or wt./vol. cryoprotectant; between 3.5 and 5.5% vol./vol. or wt./vol. cryoprotectant; or between 4 and 5% vol./vol. or wt./vol. cryoprotectant. In a further embodiment, the step of manipulating a ratio of viable X-chromosome bearing sperm to viable Y-chromosome bearing sperm to form at least one manipulated sperm population may comprise either forming droplets expected to contain selected sperm and deflecting those droplets for collection or photo-damaging selected sperm in the flow path.

A further aspect of the invention include using sperm processed using any of the methods disclosed herein to fertilize an oocyte. Such fertilization may be achieved by contacting the processed sperm with an oocyte. This embodiment of the invention encompasses the use of any in vitro fertilization (IVF) techniques known in the art, or any artificial insemination techniques that are known in the art, to achieve the fertilization.

With respect to any and all embodiments of the invention disclosed herein, including the aforementioned embodiments, the sheath fluid, staining media or collection media may comprise any of the aforementioned cryoprotectants at a vol./vol. or wt./vol. concentration of less than 8%; less than 7%; 6%; less than 6%; less than 5%; 4.5%; less than 4%; less than 3%; less than 2%; or less than 1%.

Additionally with respect to any and all embodiments of the invention disclosed herein, including the aforementioned embodiments, the sheath fluid, staining media or collection media may comprise any of the aforementioned cryoprotectants at any of the following concentrations: 10 mM to 1000 mM; 10 mM to 500 mM; 10 mM to 300 mM; 10 mM to 200 mM; 10 mM to 150 mM; less than 1000 mM; less than 900 mM; less than 800 mM; less than 700 mM; less than 600 mM; less than 500 mM; less than 400 mM; less than 300 mM; less than 200 mM; less than 150 mM; less than 100 mM; less than 50 mM; or less than 25 mM.

In an additional embodiment of the invention, the cryoprotectant for use in any of the above mentioned embodiments, including in a staining media, in a sheath fluid, in a catch fluid, or in a freezing media, can comprise erythritol. In a further embodiment, the erythritol is at a concentration of about 10 to 300 mM, about 15 to 250 mM, about 25 to 125 mM, about 40 to 80 mM, about 0.01 to 1000 mM, about 0.01 to 400 mM, about 35 mM, about 65 mM, about 135 mM, about 270 mM, about 400 mM, about 400 to 1000 mM, about 400 to 500 mM, or about 400 to 600 mM.

BRIEF DESCRIPTION OF THE DRAWINGS

FIG. 2 illustrates a graphical representation of parameters acquired in a flow cytometer while manipulating a sperm sample according to various embodiments described herein.

FIG. 3 illustrates a graphical representation of parameters acquired in a flow cytometer while manipulating a sperm sample according to various embodiments described herein.

FIG. 4 illustrates a graphical representation of sort parameters acquired in a flow cytometer while sorting sperm according to various embodiments described herein.

FIG. 13 shows post-thaw motility, viability and PIAs of sperm sorted using varying amounts of glycerol in sheath fluid.

FIG. 14 shows convergence of post-thaw motility, viability and PIAs of sperm sorted using varying amounts of glycerol in sheath fluid.

FIG. 26 shows 3 h post-thaw viability and PIAs for sperm sorted using 3% glycerol in the sheath fluid and cryopreserved in media having varying concentrations of glycerol.

FIG. 27 shows convergence of post-thaw motility for sperm sorted using 3% glycerol in the sheath fluid and cryopreserved in media having varying concentrations of glycerol.

FIG. 28 shows convergence of post-thaw viability and PIAs for sperm sorted using 3% glycerol in the sheath fluid and cryopreserved in media having varying concentrations of glycerol.

FIG. 29 shows 0 h post-thaw motility, viability and PIAs for sperm sorted using varying amounts of glycerol in the sheath fluid and cryopreserved in media having varying concentrations of glycerol.

FIG. 32 shows results of IVF using sperm sorted with either glycerol in the sheath fluid or absent from the sheath fluid.

FIG. 33 shows the post thaw motility, PIAs, convergence and viability of sperm sorted with either glycerol in the sheath fluid or absent from the sheath fluid.

MODES FOR CARRYING OUT THE INVENTION

Figure 1:
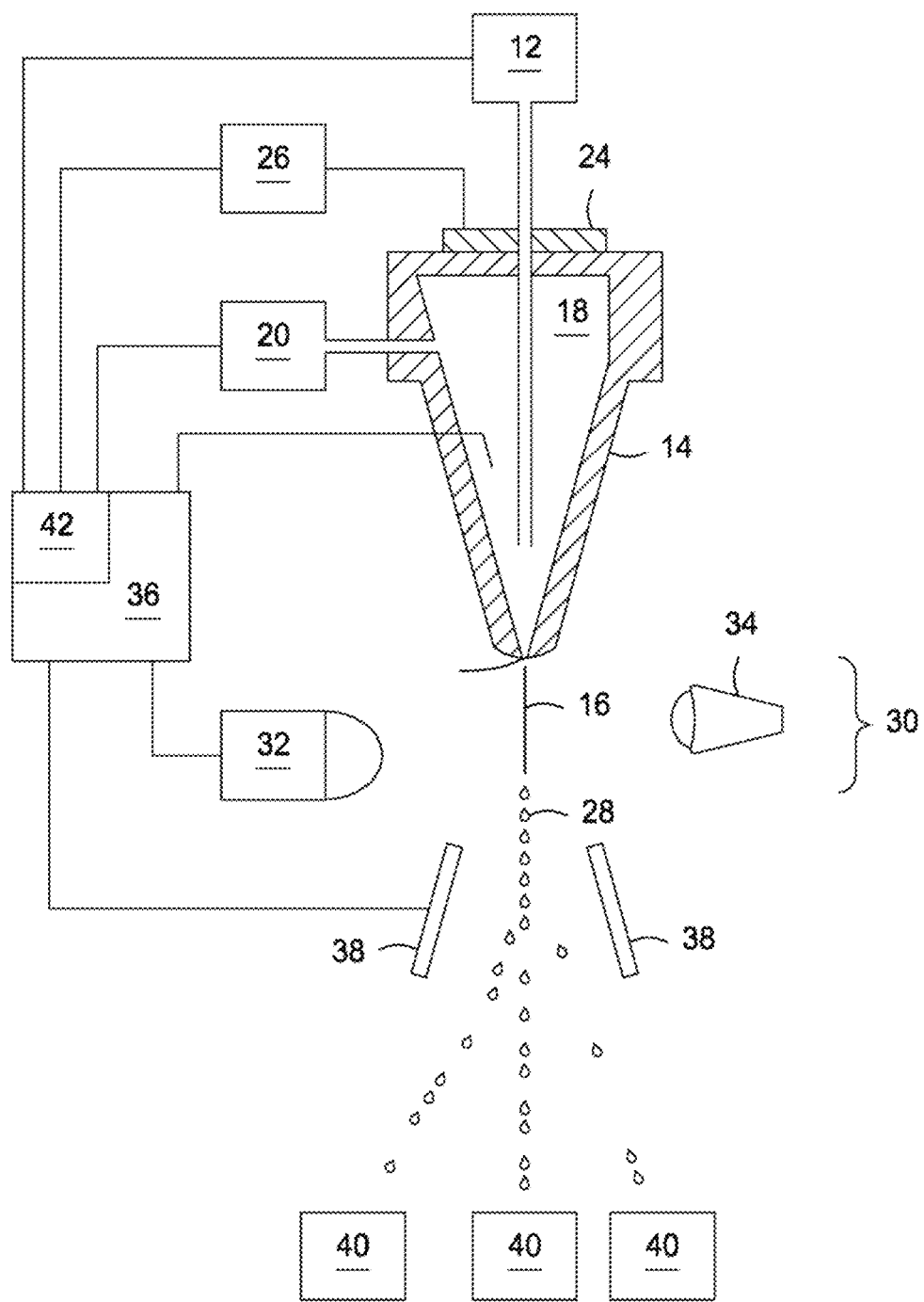
FIG. 1 illustrates a schematic of a flow cytometer for manipulating a sperm sample in accordance with certain embodiments described herein.

Sperm can be obtained, or provided, by virtue of obtaining a sperm sample or sperm solution which contains spermatozoon. As used throughout, the term "sperm" refers to the singular or plural of the male reproductive cell, whereas a "sperm sample" refers to carrier fluid in addition to the sperm contained therein. Examples of sperm samples include neat semen or sperm extended in another solution, such as an extender or buffer, and includes frozen-thawed sperm. A sperm sample can be obtained at the same location the remaining steps are performed, or can be extended in an appropriate sperm extender for transport to a sorting facility. Once obtained, the sperm can be maintained at room temperature, chilled, or even frozen in an appropriate extender for later use. Sperm for staining and sorting may be acquiring from a mammal, or may be acquired sperm from storage, such as a frozen or chilled straw obtained from storage. Alternatively, frozen or extended sperm may be pooled.

A sperm sample can originate from mammals, such as a non-human mammals listed by Wilson, D. E. and Reeder, D. M., *Mammal Species of the World*, Smithsonian Institution Press, (1993), the entire contents of which are incorporated herein by reference. At the time of collection, or thawing, or even pooling, sperm may be checked for concentration, pH, motility, and/or morphology. Additionally, antibiotics may be added prior to further processing steps.

Once obtained, sperm may optionally be standardized to a predetermined concentration and/or towards a predetermined pH. As used herein, "standardizing" may be understood as an action performed in order to bring various characteristics of an ejaculate into a predetermined range or near to said predetermined range. While bovine ejaculates, for example, may vary a great deal in pH and sperm concentration, the step of standardizing sperm concentration or pH, may include the addition of a high capacity buffer which serves to both standardize the pH and buffer against the tendency of ejaculates to become more acidic over time.

Each of the predetermined concentration and pH may be specific to different species, or even to different breeds of animals within a species. In one embodiment, the sperm may be combined with an initial extender in the form of a high capacity buffer, or an extender having a large pH buffering capacity. Suitable extenders may include TRIS citrate, sodium citrate, sodium bicarbonate, HEPES, TRIS, TEST, MOPS, KMT, TALP, derivatives thereof and combinations thereof. Any extender having a buffer with a high capacity for buffering pH may also be employed, and may be used in combination with additional components which promote sperm viability. As an example of an additive, protein may be incorporated in the form of egg yolk, milk, lipoproteins, lecithin, casein or albumin or other protein sources. An energy source may also be incorporated in the form of a monosaccharide such as fructose, glucose, or mannose, or even a disaccharide or trisaccharide. Additionally, antioxidants and antibiotics may be employed in the initial extender to promote sperm viability.

The initial extender may be set at a predetermined pH to standardize the pH of all the obtained sperm samples, such as a pH between about 6.8 and 7.4. In one embodiment, the extender is adjusted to a pH of 7.2. Additionally, semen may become increasingly acidic over time, possibly due to proteins in the seminal fluid, or due to acidic products of metabolism or byproducts of dead or dying cells. The initial extender introduces enough free proton (i.e. $H^+$) binding sites to maintain pH near the predetermined target. Even in light of the natural tendency for sperm to become more acidic over time, the initial extender provides a means for stabilizing pH throughout additional processing steps.

The initial extender may contain additives for the purpose of maintaining sperm health. The initial extender may include antibiotics to prevent the proliferation of bacteria. As non-limiting examples, tylosin, gentamicin, lincomycin, linco-spectin, spectinomycin, penicillin, streptomycin, and combinations thereof, may be incorporated into the initial extender.

Antioxidants may also be incorporated into the initial extender for reducing free radicals and oxidative stresses. While the instant discussion relates to the use of antioxidants in an initial extender, it should be appreciated antioxidants may be incorporated into multiple stages of the sperm sorting process, independently or in combination, as described in International Patent Application WO2012167151, the entire contents of which are incorporated herein by reference. A non-limiting list of antioxidants which may be incorporated includes: catalase, SOD, an SOD mimic, glutathione, glutathione reductase, glutathione peroxidase, pyruvate, caproic acid, mercaptoethanol, BHT, lipoic acid, flavins, quinines, vitamin K (and related vitamers), vitamin B12, vitamin B12 vitamers, vitamin E (and related vitamers), tocopherols, tocotrienols, α-tocopheryl, alpha ketoglutarate (AKG), malondialdehyde (MDA), asymmetric dimethylarginine (ADMA) and biologically active derivatives thereof, and combinations thereof.

The concentration of antioxidants may be in the range of 0.01 mg/ml to 0.5 mg/ml, and as non-limiting examples antioxidants listed above may be provided in the concentration 0.01 mg/ml to 5.0 mg/ml; 0.01 mg/ml to 0.25 mg/ml; 0.01 mg/ml to 0.5 mg/ml; 0.01 mg/ml to 1 mg/ml; 0.01 mg/ml to 2.5 mg/ml; 0.01 mg/ml to 5 mg/ml; 0.05 mg/ml to 0.1 mg/ml; 0.05 mg/ml to 1.0 mg/ml; 0.05 mg/ml to 2.5 mg/ml; 0.1 mg/ml to 0.25 mg/ml; 0.1 mg/ml to 0.5 mg/ml; 0.1 mg/ml to 1 mg/ml; 0.1 mg/ml to 2.5 mg/ml; 0.1 mg/ml to 5 mg/ml; 0.15 mg/ml to 0.45 mg/ml; 0.15 mg/ml to 0.5 mg/ml; 0.25 mg/ml to 0.35 mg/ml; 0.25 mg/ml to 0.5 mg/ml; 0.25 mg/ml to 1 mg/ml; 0.25 mg/ml to 2.5 mg/ml; 0.25 mg/ml to 5 mg/ml; 0.35 mg/ml to 0.5 mg/ml; 0.35 mg/ml to 1 mg/ml; 0.35 mg/ml to 2.5 mg/ml; 0.35 mg/ml to 5 mg/ml; 0.5 mg/ml to 1 mg/ml; 0.5 mg/ml to 2.5 mg/ml; 0.5 mg/ml to 5 mg/ml; 1 mg/ml to 2.5 mg/ml; and 1 mg/ml to 5 mg/ml.

As one example, the sperm sample may be diluted in the high capacity buffer in ratios from about 1:1 to about 1:10. The resulting mixture will have a sperm concentration many times below natural sperm concentrations for a particular species. The extended sperm may be centrifuged in order to reconcentrate sperm. Centrifuging the sperm and removing supernatant allows the sperm to be reconcentrated into a predetermined concentration. The predetermined concentration may be selected based on additional sperm processing steps. For example, in the case of sex sorting bovine, sperm may be reconcentrated at between about 2400 million sperm per ml and about 500 million sperm per ml to simulate a natural range of concentrations while replacing seminal plasma components with extender. Other concentrations, such as between about 1400 million sperm per ml and about 2100 million sperm per ml, or between about 1700 million sperm per ml and about 2100 million sperm per ml may also be achieved for further processing.

In one embodiment, sperm concentration and pH may provide a uniform starting point for further processing. For example, a relatively consistent pH and concentration may provide greater predictability in staining sperm, for example with a DNA selective dye. If each sample is adjusted to the same predetermined pH and concentration, fewer trials may be required on each new collection to ensure adequate staining for sex sorting.

A population of sperm will include both X-chromosome bearing sperm and Y-chromosome bearing sperm. Additionally, each of the X-chromosome bearing sperm and the Y-chromosome bearing sperm will include viable sperm and nonviable sperm. Viable sperm can be considered sperm with intact membranes while nonviable sperm can be considered sperm with compromised membranes. The distinction between viable sperm and non-viable sperm in conventional sperm sorting is determined with the inclusion of a quenching dye that permeates membrane compromised sperm. Sperm which tends to be dead or dying absorbs the quenching dye and produces fluorescence signals distinct from the remaining sperm population, whereas sperm having intact membranes tend to be viable and will prevent uptake of the quenching dye. Viable sperm, in the appropriate dosage, will generally be capable of achieving fertilization in an artificial insemination, while nonviable sperm, or membrane compromised sperm, may be incapable of achieving fertilization in an artificial insemination or will have a greatly reduced capacity to do so. However, some sperm capable of fertilization may have compromised membranes, and some sperm with intact membranes may be incapable of fertilization.

Whether standardized or not, sperm may be stained with a staining media for introducing a DNA selective dye. In the staining step, at least a portion of the population of sperm is incubated with a staining media and a DNA selective fluorescent dye in order to stoichiometrically stain the DNA content of each cell in the sperm population. Hoechst 33342 tends to be less toxic than other DNA selective dyes. The vehicle for delivering this dye may be in the form of a modified TALP buffer adjusted to a pH of about 7.4. Hoechest 33342 is described in U.S. Pat. No. 5,135,759 and is commonly used for this purpose. However, other UV excitable dyes, as well as visible light excitable dyes, fluorescent polyamides, fluorescent nucleotide sequences, and sex specific antibodies could also be used.

Sperm in a natural state is often not readily permeable to such dyes. In order to produce a uniform staining, the first step of staining can include incubating at least a portion of the sperm population at an elevated temperature in a staining media (sometimes referred to herein as a staining buffer) at an elevated pH in addition to the dye. Examples of appropriate staining solutions can be a TALP, TES-TRIS, TRIS citrate, sodium citrate, or a HEPES based medium, each described in WO2005/095960, which is incorporated herein by reference. A non-limiting example of a modified TALP described in WO2001/37655, incorporated herein by reference, is illustrated in Table 1.

TABLE 1

Modified TALP buffer

| Ingredient | Concentration |
|---|---|
| NaCl | 95.0 mM |
| KCl | 3.0 mM |
| NaHPO$_4$ | 0.3 mM |
| NaHCO$_3$ | 10.0 mM |
| MgCL$_2$ 6H$_2$O | 0.4 mM |
| Na Pyruvate | 2.0 mM |
| Glucose | 5.0 mM |
| Na Lactate | 25.0 mM |
| HEPES | 40.0 mM |
| bovine serum albumin | 3.0 mg/ml |

As one example, the population of sperm, or a portion of the population of sperm, could be diluted with the staining media to between $640 \times 10^6$ and $40 \times 10^6$ sperm/ml, to between about $320 \times 10^6$ and $80 \times 10^6$ sperm/ml, or to about $160 \times 10^6$ sperm/ml in the buffer. The DNA selective fluorescent dye can be added to the sperm suspended in the buffer in a concentration of between about 10 μM and 200 μM; between about 20 μM and 100 μM, or between about 30 μM and 70 μM. The pH of the buffer can be between about 6.8 and 7.9; about 7.1 and 7.6; or at about 7.4 in order to help ensure a uniform staining of nuclear DNA. Those of ordinary skill in the art will appreciate the pH can be elevated with the addition of NaOH and dropped with the addition of HCl. Optionally, the previously described antioxidants and concentrations may be incorporated into the staining solution.

The population of sperm can be incubated between 30-39° C., between about 32-37° C., or at about 34° C. The period of incubation can range between about 20 minutes and about three hours, between about 30 minutes and about 90 minutes, or for about 45 minutes to about 60 minutes. As one example, the population of sperm can be incubated for about 45 minutes at 34° C. Even within a single species, sperm concentration and pH and other factors affecting stainability can vary from animal to animal. Those of ordinary skill in the art can appreciate minor variations for incubating sperm between species and even between breeds or animals of the same breed to achieve uniform staining without over staining a population of sperm.

In addition to the DNA selective fluorescent dye, a quenching dye may be applied for the purpose of permeating membrane compromised sperm and quenching the signals they produce. A quenching dye can be understood to include dyes which differentially associate with membrane compromised sperm. It may be that these dyes enter membrane compromised sperm more easily because the membranes are breaking down or otherwise increasingly porous. It may also be that quenching dyes readily enter all sperm membranes and that healthy sperm actively pump quenching dyes out faster than membrane compromised sperm. In either case, the sperm with which the quenching dyes associate includes a large portion of dead and dying sperm, although not necessarily all dead and dying sperm. The quenched signals produced from membrane compromised sperm having an association with quenching dye are distinct enough from the signals of healthy sperm that they may be removed from the further analysis and sorting applied to viable sperm.

In one embodiment, a second staining step is preformed which further reduces the concentration of sperm and introduces the quenching dye. The pH of the second staining media may be targeted to achieve a target pH in the final sperm sample. Non-limiting examples of two step staining processes are described in published PCT International Application WO 2011/123166 and International Application PCT/US12/58008, the entire disclosure of both are incorporated herein by reference.

In another embodiment, the quenching dye and the DNA selective dye are applied together in a single dilution. In this embodiment, the quenching dye is incubated along with the DNA selective dye at an elevated temperature in the staining solution. As an example, the staining media may be a modified TALP with a pH of 7.4. However, other stains may be employed including a TES-TRIS, TRIS citrate, sodium citrate or a HEPES based medium having the DNA selective dye and the quenching dye and pH may range between about 7.0 and 7.8. In one embodiment, a synergy may exist when sperm is standardized at an elevated pH of about 7.2 before staining at a pH of 7.4. In this way, the pH to which the sperm is exposed remains in a constant range with minimal variations. Because both the staining media and the initial extender have high buffering capacities, it is believed the natural tendency of sperm to become more acidic over time will be avoided.

In one embodiment, independent of whether a one step or a two step staining protocol is employed, a cryoprotectant may be incorporated into the staining step or steps. It should be understood that as used herein the term "cryoprotectant" refers to a substance that protects cells or biological tissue from freezing damage. Cryoprotectants may include those substances which act to remove intracellular water to prevent damage associated with the formation and expansion of intracellular ice. Such action may be induced by increasing solute concentrations within cells. Substances that protect cells and tissue from other types of damage, such as osmotic shock and chilling, but not freezing, are not considered cryoprotectants. As but a few examples, sources of lipoproteins, phospholipids, lecithin and the like, such as egg yolk, an egg yolk extract, milk, a milk extract, casein, albumin, lecithin, and cholesterol, are not cryoprotectants, as the term is used herein. Additionally, energy sources such as monosaccharides, disaccharides, and trisaccharides, are not cryoprotectants as used herein.

Cryoprotectants which may be incorporated at the staining step include a number of sugar alcohols and glycols. As non-limiting examples sugar alcohols such as ethylene glycol; glycerol; erythritol; threitol; arabitol; ribitol; xylitol; sorbitol; galactitol; iditol; volemitol; fucitol; inositol; a glycylglycitol, and combinations thereof may be included as a cryoprotectant introduced at the time of staining. U.S. Pat. No. 3,185,623, the entire contents of which are incorporate herein by reference, describes a number of carbohydrate alcohols (i.e. sugar alcohols or alditols) which may be suitable cryoprotectants usable in the present invention. Additionally, glycols such as propylene glycol, butane triol may be included as a cryoprotectant. Many such cryoprotectants are toxic to sperm at certain concentrations and temperatures. Glycerol, for example, is generally added to sperm after chilling the sperm to a temperature of 5° C. specifically because of this toxicity. Unexpectedly, as described in more detail in the Examples, the presence of a cryoprotectant during the staining step has been shown to improve the post thaw motility of subsequently frozen sperm and to improve the sperm sorting resolution. This is a particularly surprising and unexpected result in view of the fact staining sperm for the purpose of sex sorting is typically carried out at temperatures in excess of 34° C.

The cryoprotectant may be provided during the staining step, such as in a staining media, at vol/.vol. or wt./vol. concentrations between about 0.1% and about 5%. For example, the stained sperm sample to undergo further processing, such a sorting in a flow cytometer may comprise cryoprotectant at a vol./vol. or wt./vol. concentration between about 0.1% and about 1%; between about 1% and about 2%; between about 2% and about 3%; between about 3% and about 4%; between about 2% and about 4%; or between about 1.5% and about 3%.

The stain may be supplemented with an antioxidant in the previously described concentration ranges. In some embodiments, elevated pressures may increase free radicals and oxidative stresses endured by sperm being stained. Accordingly, antioxidants may serve to neutralize free radicals and reduce the oxidative stresses endured by the sperm being stained. A non-limiting list of antioxidants which may be incorporated in the staining process includes: catalase, SOD, an SOD mimic, glutathione, glutathione reductase, glutathione peroxidase, pyruvate, caproic acid, mercaptoethanol, BHT, lipoic acid, flavins, quinines, vitamin K (and related vitamers), vitamin B12, vitamin B12 vitamers, vitamin E (and related vitamers), tocopherols, tocotrienols, α-tocopheryl, alpha ketoglutarate (AKG), malondialdehyde (MDA), asymmetric dimethylarginine (ADMA) and biologically active derivatives thereof, and combinations thereof. Any of the previously described concentrations may be used.

The step or steps of staining may optionally include components for reducing motility or respiration of sperm during staining. As but a few examples, the staining step or steps may reduce sperm respiration by including additives, or by reducing and/or reducing sperm exposure to certain substances. In particular, a low sugar stain may be utilized in which only residual level of fructose, sucrose, glucose or another sugar is present. Similarly, sperm respiration may be reduced by staining under a partial pressure of nitrogen or carbon dioxide to displace oxygen in the stain. Alternatively, substances may be added to the stain which have certain potassium and sodium ratios that tend to reduce sperm respiration. As another alternative, fluoride or sodium fluoride may be added to the staining step or steps in order to reduce sperm respiration.

Whether standardized or not and whether stained in a single step or in two steps, the sperm population can be sorted by a particle sorting instrument, such as flow cytometer, including without limitation a jet-in-air flow cytometer, a flow cytometer with a cuvette, or a microfluidic chip. Referring to FIG. 1, a jet-in-air flow cytometer (10) is illustrated, although sorting may be performed with microfluidic chips or other types of flow cytometers, including flow cytometer having closed chambers and cytometers and cytometers incorporating ablating lasers. The flow cytometer (10) includes a cell source (12) for producing a flow of sperm sample, such as a flow of stained sperm sample, for sorting. The rate at which the sperm sample is delivered to the nozzle (14) may be considered the sample flow rate, and may be determined by a sample pressure. The flow of stained sperm sample is deposited within a nozzle (14) and introduced into, or flowed into, a fluid stream (16) of sheath fluid (18). The sheath fluid (18) can be supplied by a sheath fluid source (20) so that as the cell source (12) supplies the sperm into the sheath fluid (18) they are concurrently fed through the nozzle (14). The sheath fluid (18) may be supplied at a sheath flow rate which is determined by a sheath fluid pressure.

Whereas prior sheath fluids utilized in flow cytometry generally comprised a phosphate buffered saline (PBS), perhaps supplemented with bovine serum albumin (BSA), sperm sorting has incorporated sodium citrate, TRIS citrate, or citric acid as a sheath fluid to preserve sperm heath during the sorting process. As described in International Patent Application WO 99/33956, the entire contents of which are incorporated herein by reference, suitable buffers may be incorporated as sheath fluids. In certain embodiments of the present invention, the prior sheath fluids are supplemented with a cryoprotectant. As described above, cryoprotectants refer to a substances that protect cells or biological tissue from freezing damage and may include those substances which act to remove intracellular water to prevent damage associated with the formation and expansion of intracellular ice. Such action may be induced by increasing solute concentrations within cells. Substances which protect cells and tissue from other types of damage, such as osmotic shock and chilling, but not freezing, are not considered cryoprotectants.

Cryoprotectants include a number of sugar alcohols and glycols described above. As non-limiting examples sugar alcohols such as ethylene glycol; glycerol; erythritol; threitol; arabitol; ribitol; xylitol; sorbitol; galactitol; iditol; volemitol; fucitol; inositol; a glycylglycitol, and combinations thereof may be included in the sheath fluid as a cryoprotectant. Additionally, glycols such as propylene glycol, butane triol may be included in the sheath fluid as a cryoprotectant. Unexpectedly, as described in more detail in the Examples, the presence of a cryoprotectant in the sheath fluid has been shown to improve the post thaw motility of subsequently frozen sperm and to improve the sperm sorting resolution. Surprisingly, as seen in Example 1, the modification of a sorting instrument by the inclusion of a cryoprotectant in the sheath fluid according to certain embodiments of the invention improved the sorting resolution, meaning that productivity, throughput, and purity could be simultaneously improved to varying degrees.

In some embodiments, the same cryoprotectant may be used during both the staining step and in the sheath fluid. As a non-limiting example of such an embodiment, glycerol may be provided at a first vol./vol. or wt./vol. concentration during the staining step and at a second vol./vol. or wt./vol. concentration in the sheath fluid. In one embodiment, the first vol./vol. or wt./vol. concentration provided during staining may be lower than the second vol./vol. or wt./vol. concentration provided in the sheath fluid. In this way, sperm cells undergoing the sperm sorting process may be exposed to a gradually increasing relative concentration of sheath fluid. Alternatively, the amount of cryoprotectant present in the staining media and in the sheath fluid can be coordinated, so that during the course of whatever process is manipulating the sperm sample, a predetermined concentration of cryoprotectant is reached at the end of that manipulation. In alternative embodiments, cryoprotectant can be incorporated into only one of the sheath fluid and the staining media.

In some embodiments, the cryoprotectant may be provided in the sheath fluid at concentrations between about 0.1% vol/.vol. or wt./vol. and about 6% vol./vol. or wt./vol. For example, the stained sperm solution to undergo further processing, such as sorting in a flow cytometer may comprise cryoprotectant at a vol./vol. or wt./vol. concentration between about 0.1% and about 2%; between about 2% and about 4%; between about 4% and about 6%; between about 1% and about 2%; between about 2% and about 3%; between about 3% and about 4%; between about 4% and about 5%; between about 5% and about 6%; between about 2% and about 6%; or between about 3% and about 5%.

Those of skill in the art can appreciate that the described embodiment relates to a droplet forming jet-in-air flow cytometer, but that the sheath fluid having a cryoprotectant additive provides the same benefits in other sorting systems, such in systems that utilize fluid switching, systems that utilize photo-damaging lasers, and in microfluidic chips.

During operation the operation of sorting sperm, the sheath fluid (18) forms a fluid stream coaxially surrounding the sperm sample having stained sperm which exits the nozzle (14) at the nozzle orifice (22). By providing an oscillator (24) which may be precisely controlled with an oscillator control (26), pressure waves may be established within the nozzle (14) and transmitted to the fluids exiting the nozzle (14) at nozzle orifice (22). In response to the pressure waves, the fluid stream (16) exiting the nozzle orifice (22) eventually forms regular droplets (28) at precise intervals. The frequency, and to some extent the shape of the formed droplets may be controlled by a drop drive frequency and drop drive amplitude supplied to the oscillator (24) or the oscillator controller (26).

Each droplet, so formed, retains the sheath fluid and sperm sample that previously formed a portion of the fluid stream (16). Because the stained sperm are surrounded by the fluid stream (16) or sheath fluid environment, the droplets (28) ideally contain individually isolated sperm. However, the sample concentration, sample pressure, and other instrument parameters dictate the frequency with which multiple cells will regularly occupy a single droplet, as well as the percentage of droplets containing sperm.

The flow cytometer (10) acts to sort droplets based on the characteristics of sperm predicted to be contained within the droplets. This can be accomplished through a cell sensing system (30) in communication with an analyzer (36). The cell sensing system (30) includes at least one sensor (32) responsive to the cells contained within fluid stream (16). As one example, two orthogonal photomultiplier tubes (PMTs) may be incorporated into a sperm sorting flow cytometer for detecting fluorescence at 0 degrees and 90 degrees, although other sensor configurations can readily be employed, such as those described in WO2010/021627, which is incorporated herein by reference.

The cell sensing system (30) provides data to the analyzer (36), which may cause an action depending upon the relative presence or relative absence of a characteristic of cells in the fluid stream (16). Certain characteristics, such as the relative DNA content of sperm, can be detected through excitation with an electromagnetic radiation source (34), such as a laser generating an irradiation beam to which the stained sperm are responsive. The electromagnetic radiation source (34) can be a laser operated at UV wavelength, such as at about 355 nm. An example of such a laser can be a Vanguard 350 (available from Spectra-Physics), which operates at 350 mW. Various optics may be employed to shape the beam profile of the laser, split the beam to more than one stream, or reduce the beam power at a stream. Non-limiting examples of such optics can be found in WO/2004/104178 and WO/2001/85913, each being incorporated herein by reference.

The characteristics of individual sperm, particularly the presence of an X-chromosome or a Y-chromosome can be determined from the detected fluorescence produced in response to the electromagnetic radiation source (34). In particular, configurations of the cell sensing system (30) may be in communication with an analyzer (36) for providing a variety of fluorescence in formation, such as the forward fluorescence of an event, the side fluorescence of an event, or the amount of scatter associated with an event. The analyzer (36) may include written instructions for analyzing the signals produced by the one or more sensors (32) in the cell sensing system (30). The DNA selective fluorescent dye binds stoichiometrically to sperm DNA. Because X-chromosome bearing sperm contain more DNA than Y-chromosome bearing sperm, the X-chromosome bearing sperm can bind a greater amount of DNA selective fluorescent dye than Y-chromosome bearing sperm. Thus, by measuring the fluorescence emitted by the bound dye upon excitation, it is possible to differentiate between X-bearing spermatozoa and Y-bearing spermatozoa. Distinctions, such as sperm which is viable or not viable, may be differentiated in addition to oriented and unoriented sperm by the analyzer (36) according to sorting logic incorporated gating regions.

Once an analyzer differentiates sperm based upon a sperm characteristic, the droplets entraining X-chromosome bearing spermatozoa can be charged positively and thus deflect in one direction, while the droplets entraining Y-chromosome bearing spermatozoa can be charged negatively and thus deflect the other way, and the wasted stream (that is droplets that do not entrain a particle or cell or entrain undesired or unsortable cells) can be left uncharged and thus collected from an undeflected stream into a suction tube or the like. Alternatively, one of the X-chromosome bearing sperm or the Y-chromosome bearing sperm may be collected, while the other is discarded with waste.

As a result, the flow cytometer (10) acts to separate stained sperm by causing the droplets (28) containing sperm to be directed to one or more collection containers (40). The collection containers (40) can be collection tube such as centrifugation tubes or Falcon tubes. In one embodiment, the one or more collection containers comprise a 50 ml centrifugation tube. The one or more collection containers may include a collection media that both acts to cushion cells in deflected droplets from impact with the bottom of the container and which includes components for preserving the health of sorted sperm cells. By way of an example, a Tris-Citrate and egg yolk catch fluid may be employed with certain embodiments of the present invention. Other catch fluids which may be used in certain embodiments include TRIS citrate, sodium citrate, sodium bicarbonate, HEPES, TRIS, TEST, MOPS, KMT, TALP, derivatives thereof and combinations thereof. However, other extenders having a buffer for buffering pH may also be employed, and may be used in combination with additional components which promote sperm viability after sorter. As an example of an additive, protein is commonly incorporated in catch fluid in the form of egg yolk. However, other forms of protein such as, milk, lipoproteins, lecithin, casein or albumin or other protein sources could alternatively be used, or even used in combination with egg yolk. In one embodiment, an egg yolk substitute, such as phospholipid available from soy lecithin may be used in placed of egg yolk. An energy source may also be incorporated in the form of a monosaccharide such as fructose, glucose, or mannose, or even a disaccharide or trisaccharide. Additionally, antioxidants and antibiotics may be employed in the initial extender to promote sperm viability.

In one embodiment, the collection media includes a cryoprotectant. Cryoprotectants suitable for addition to the collection media include a number of sugar alcohols and glycols described above. As non-limiting examples sugar alcohols such as ethylene glycol; glycerol; erythritol; threitol; arabitol; ribitol; xylitol; sorbitol; galactitol; iditol; volemitol; fucitol; inositol; a glycylglycitol, and combinations thereof may be included in the catch fluid as a cryoprotectant. Additionally, glycols such as propylene glycol, butane triol may be included in the catch fluid as a cryoprotectant.

In some embodiments, the collection of a manipulated sperm sample in a collection media may be the first time the sperm comes into contact with a cryoprotectant. In some embodiments, the staining media and/or the sheath fluid include a cryoprotectant in addition to the collection media. In other embodiments, the staining media and/or the sheath fluid contain a cryoprotectant, while the collection media does not. In each of said embodiments, sperm collected in a collection media is collected in a mixture that includes both sperm and a cryoprotectant by virtue of the cryoprotectant present in the collection media or alternatively because of any amounts of cryoprotectant present in either the staining media or the sheath fluid, which are themselves collected with the manipulated or collected sperm.

In embodiments, where cryoprotectant is present in the collection media and in at least one other fluid, the same cryoprotectant may be used in the collection media as in the staining media and/or the sheath fluid. As a non-limiting example of such an embodiment, glycerol may be provided at a first vol./vol. or wt./vol. concentration during the staining step and at a second vol./vol. or wt./vol. concentration in the sheath fluid. In one embodiment, the first vol./vol. or wt./vol. concentration provided during staining may be lower than the second vol./vol. or wt./vol. concentration provided in the sheath fluid. In this way, sperm cells undergoing the sperm sorting process may be exposed to a gradually increasing relative concentration of sheath fluid. Alternatively, the amount of cryoprotectant present in the collection media can be coordinated with the amount of cryoprotectant present in the staining media and/or in the sheath fluid, so that during the course of whatever process is manipulating the sperm sample, a predetermined concentration of cryoprotectant is reached at the end of that manipulation. In alternative embodiments, cryoprotectant can be incorporated into only one of the sheath fluid, the staining media and the collection media.

In some embodiments, the cryoprotectant may be provided in the collection media at a vol./vol. or wt./vol. concentration between about 1% and about 2%; between about 2% and about 4%; between about 4% and about 6%; between about 3% and about 5%; between about 3.5% and about 5.5%; or about 4.5%.

In one embodiment, the cryoprotectant is added to the catch fluid, but not to the sheath fluid or the staining step(s). In another embodiment the cryoprotectant is added to any two of the catch fluid, sheath fluid and the staining step(s). In still another embodiment the cryoprotectant is added to each of the catch fluid, sheath fluid and the stain. As a non-limiting example of an embodiment in which cryoprotectant is added in more than one processing step, glycerol may be provided at a first vol./vol. or wt./vol. concentration during the staining step and at a second vol./vol. or wt./vol. concentration in the sheath fluid. In one embodiment, the first vol./vol. or wt./vol. concentration provided during staining may be lower than the second vol./vol. or wt./vol. concentration provided in the sheath fluid. In this way, sperm cells undergoing the sperm sorting process may be exposed to a gradually increasing relative concentration of sheath fluid. As a non-limiting example of an embodiment in which a cryoprotectant is added in each of the catch fluid, the sheath fluid and at the staining step(s) glycerol may be provided at a first vol./vol. or wt./vol. concentration during the staining step, at a second vol./vol. or wt./vol. concentration in the sheath fluid, and at a third vol./vol. or wt./vol. concentration in the catch fluid. In one embodiment, the vol./vol or wt./vol. concentration of the cryoprotectant may be increased in each successive step in which it is introduced. For example, the first concentration of cryoprotectant during the staining step may be a lower concentration than the second concentration of cryoprotectant in the sheath fluid and the third concentration of cryoprotectant in the catch fluid. The gradual introduction of cryoprotectant may particularly benefit the ability of sperm to ultimately survive eventual freezing and thawing, or may improve the health of viable sperm which is eventually frozen and thawed.

In an alternative embodiment, the deflection plates a (38) and other components required for forming droplets, such as the oscillator (24) or the oscillator controller (26), may be replaced by a photo-damaging laser, sometimes also referred to as laser ablation. In such an embodiment, the analyzer (36) and controller (42) may cooperate in triggering a photo-damaging laser timed to strike cells in the fluid stream (16) at a second location downstream of the electromagnetic radiation source (34) based on the classifications of the cells. Such a laser may be operated at a different wavelength as compared to the electromagnetic radiation source (34), or at a higher power to ensure that sperm cells are ablated, deactivated, or rendered incapable of fertilization. Embodiments which incorporate such a photo-damaging laser still utilize a staining media and a sheath fluid and may optionally utilize a collection media. In accordance with certain embodiments of the present invention any one of the staining media, sheath fluid and collection media, when present, can include a cryoprotectant.

In a further alternative, certain aspects of the current invention may be equally applicable in microfluidic chips. As but one example, the microfluidic chips, such as those described in International Application WO 2011/097032, which is incorporated herein by reference, may likewise benefit from the inclusion of a cryoprotectant containing sheath fluid. Similarly, embodiments which incorporate flow channels on microfluidic chips still utilize a staining media and may optionally utilize a sheath fluid and a collection media. In accordance with certain embodiments of the present invention any one of the staining media, sheath fluid and collection media, when present, can include a cryoprotectant.

FIG. 2 illustrates a representative bivariate plot of side fluorescence and forward fluorescence from a jet-in-air flow cytometer of stained sperm, which may be generated by an analyzer (36). The visual representation of data may be used by an operator to receive feedback relating to the sample undergoing sorting and to graphically demonstrate certain aspects of the current sorting logic. R1, for example, can be seen as a gating region which may be applied to the sort logic of the flow cytometer. Additional numerical output may be provided in a display of the analyzer (36). Such numerical output may be in the form of measured sorting parameters, such as an event rate, an abort rate, sort rate, sorting efficiency, or the percentage of particles in any region or gate. R1 is illustrated as a region which may be considered the live oriented region, because the boundaries of R1 include two dense populations of cells which reflect a closely related X-chromosome bearing population of sperm and Y-chromosome bearing population of sperm. R2 is a gating region set around the non-viable sperm, or the membrane compromised sperm whose fluorescence is quenched by a quenching dye. While a variety of sort logics may be employed, two strategies relating to R1 and R2 might be a first step in a sorting logic whereby all events falling in R1 are accepted for further processing or gating. Alternatively, all events falling outside of R2 are accepted for further processing or gating.

FIG. 3 illustrates a univariate plot in the form of a histogram that may be produced by the analyzer (36) and generated into a graphical presentation for an operator. The data illustrated in FIG. 3 may represent the number of occurrence of peak signal intensities from the side or forward fluoresce within a certain period. In the case of sperm, X-chromosome bearing sperm and Y-chromosome bearing sperm tend to have peak intensities that vary by between 2 and 5%, depending on the species, and this difference is reflected in the bimodal distribution of peak intensities seen in FIG. 2. Because X-chromosome bearing sperm and Y-chromosome bearing sperm tend to have differing fluorescence values, each of the peaks represents either X-chromosome bearing sperm of Y-chromosome bearing sperm. Based on the sort logic applied within the analyzer (36), the population of cells in the histogram may be only those cells which were determined to be viable oriented cells, such as those falling into R1 in FIG. 2, or they may represent cells which were not determined to be dead or undesirable, such as every event except those falling in R2. A variety of sorting parameters may be derived from the information contained within this histogram. For example, the level of distinctiveness between the two peaks may provide an indication of what a sorted purity may look like. FIG. 3 further illustrates relative intensity measurements at the lowest point between the two groups, which may be considered a value V and a second relative intensity at the peak or peaks of the histogram at P. A visual inspection of a histogram may provide an operator with an idea of how a flow cytometer is performing, but computer executed instructions for determining a P value, a V value, and a ratio of V to P has not been implemented in commercial sperm sorters. The valley to peak ratio, may be determined as a measured sorting parameter periodically during the course of sorting. The valley to peak ratio, while not the necessarily completely determinative of sorting purities, may provide a means for quickly estimating purity values, either automatically by the execution of written instruction in the analyzer (36), or manually by visual inspection of an operator. Alternatively, the inverse relationship, namely a peak to valley ratio, provides similar information as the inverse value.

Turning to FIG. 4, a second bimodal plot may be generated by the analyzer (36) in response to signals acquired by the cell sensing system (30). The bimodal plot may represent a first axis illustrating the peak intensity value of a forward fluorescence signal or the peak intensity of side fluorescence signal. Like FIG. 3, the data illustrated in FIG. 4 may be gated such that only events falling within R1 in FIG. 2 are included. Alternatively, in the case of sperm, all events which do not fall into the dead gate R2 may also be displayed.

R3 may represent an X-sort gate for collecting X-chromosome bearing sperm. The term X-sort gate may be used interchangeably herein with the term X-gate. With reference to FIG. 4, it may demonstrate how changing the dimensions of the gating regions may affect efficiency, purity, and productivity. If the R3 region were to be expanded, it could be seen that every second more sperm would be sorted as X-chromosome bearing sperm resulting in higher sorting efficiency and higher productivity. However, the expansion of the R3 gate or region would begin to include events having an increasing likelihood of being Y-chromosomes bearing sperm. In order to increase the sorted purity of sperm, the R3 region can be made smaller and/or moved away from the Y-chromosome region. As fewer events fall within the X-sort gate, fewer sperm are sorted in the X-chromosome bearing sperm population and those which are have a greater probability of actually being X-chromosome bearing sperm, meaning the collected purity may be increased. However, both the efficiency, in terms of cells collected, and the productivity, in terms of sorts per second, will decrease as fewer events fall within the R3 region and more coincident events are aborted. Additionally, as other instrument parameters are modified, the illustrated graphs of FIG. 2, FIG. 3, and FIG. 4 may change in shape and nature. For example, increasing a sample pressure or a sample flow rate may result in a reduction in the valley to peak ratio, or may otherwise lessen the bimodal distinction between X-chromosome bearing sperm and Y-chromosome bearing sperm.

Processed sperm may then be pooled and frozen according to known methodologies for conventional or for sex-selected sperm. As but one example, the freezing methodologies described in International Patent Application WO/200137655, incorporated herein by reference in its entirety, may particularly benefit from certain embodiments of the described invention in which a cryoprotectant is introduced into the sperm sorting processes at earlier steps, such as at the time or staining, in the sheath fluid, or even in the catch fluid. Alternatively, the inclusion of a cryoprotectant in one or more earlier steps may be incorporated into a new freezing methodology.

In one embodiment, collected sorted sperm may be cooled to a temperature of about 5° C., or to another suitable cooled temperature based on the particular species sperm. Alternatively, the sperm may be collected in a collection container which is already cooled. Depending on the size of the collection container, collected sperm may be pooled with additional collection containers. Pooled collection containers may be centrifuged and the supernatant run off. According to some previous methodologies the isolated sperm would be re-suspended in an A fraction (or cryoprotectant free fraction) of extender and a B fraction (or cryoprotectant containing fraction) having twice the desired concentration of cyroprotectant would be added at an equal volume to the A fraction. Some previous methodologies added the B fraction in two equal volumes about 15 minutes apart, while other methodologies introduced the B fraction through a steady drip.

In some embodiments of the invention, cryoprotectants are included in various medias throughout the staining, sorting and collection steps, which may reduce, or even eliminate, the need to cool a manipulated sperm sample prior to reconcentrating. Further, the inclusion of cryoprotectant in the various staining and sorting steps may eliminate the need for the use of an "A" and "B" fraction paradigm.

Figure 5:
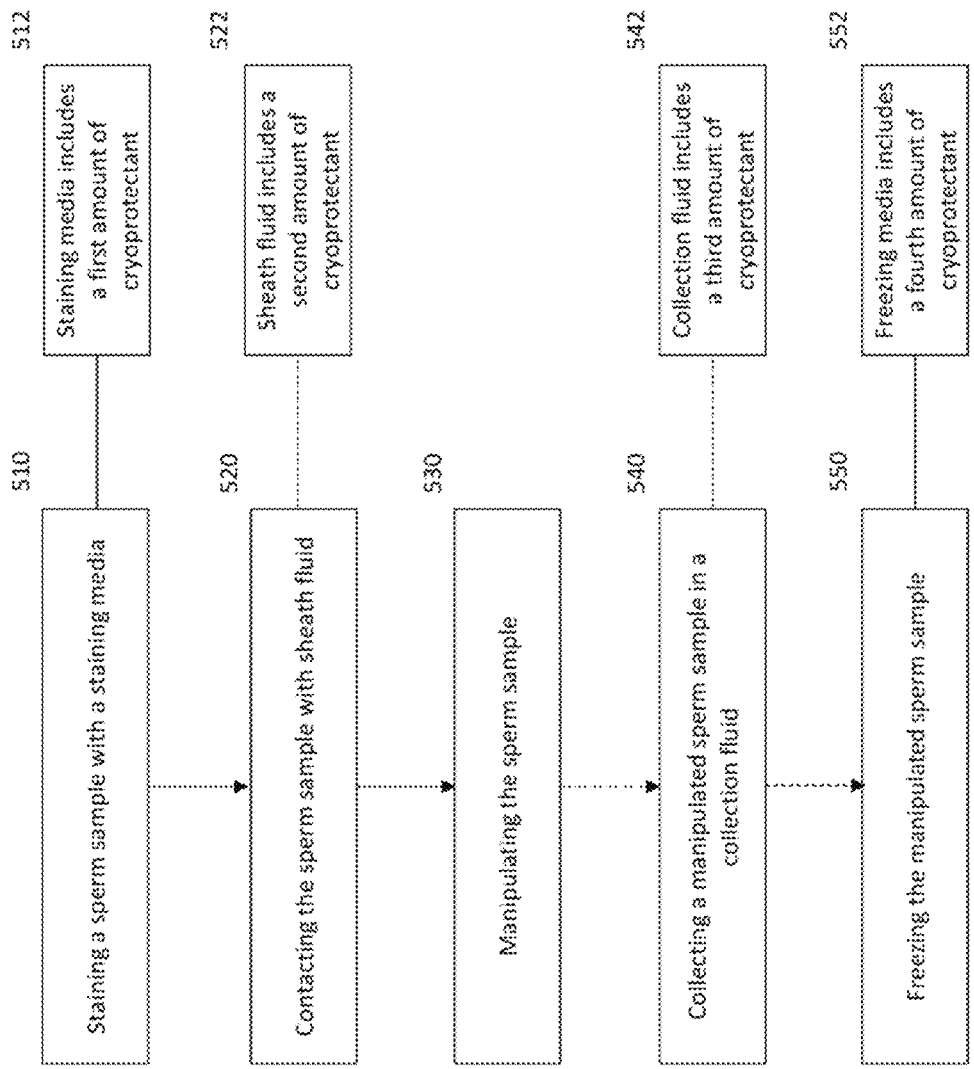
FIGS. 5-7 illustrate alternative embodiments in the use of cryoprotectant at various stages of sperm sample processing.

Turning to FIG. 5, an illustrated embodiment of the current invention relates to a method in which cryoprotectants are added to multiple medias during the processing of sperm, such as in the staining media, the sheath fluid and in the collection media. At step (510) the method begins with the step of staining a sperm sample in a staining media. The sperm sample may be neat semen or sperm extended in another solution, such as a those described previously. As an example, the sperm sample may be standardized by extension and reconcentration in the manner described previously. Alternatively, the sperm sample may take the form of neat semen, or neat semen extended with a buffer and and/or having antibiotics added.

Whether standardized or not, the DNA selective fluorescent dye may be Hoechst 33342 supplied in a modified TALP buffer (Table 1). The staining step itself may be performed in a single dilution which additionally includes a quenching dye. Alternatively, step 510 may be performed in two dilutions, such as in a first dilution with a modified TALP having the DNA selective fluorescent dye followed by a second dilution in a modified TALP having a quenching dye. It can be understood other DNA selective fluorescent dyes and other quenching dyes may be used in accordance with this example. For the purpose of this embodiment, each will be referred to as a staining media.

Regardless of where achieved in one dilution or two, the sperm sample can be diluted to between $640 \times 10^6$ and $40 \times 10^6$ sperm/ml, to between about $320 \times 10^6$ and $80 \times 10^6$ sperm/ml, to about $160 \times 10^6$ sperm/ml or to about $120 \times 10^6$ sperm/ml in the staining media. The DNA selective fluorescent dye can be added to the sperm suspended in the staining media in a concentration of between about 10 µM and 200 µM; between about 20 µM and 100 µM, or between about 30 µM and 70 µM. The pH of the staining media can be between about 6.8 and 7.9; about 7.1 and 7.6; or at about 7.4. In the case of two dilutions, the second dilution can be performed at or near the same pH as the first dilution or at a low pH, such as between 5.0 and 6.0, or at about 5.5. Optionally, the previously described antioxidants and concentrations may be incorporated into the staining media. The sperm sample can be incubated between 30-39° C., between about 32-37° C., or at about 34° C. The period of incubation can range between about 20 minutes and about three hours, between about 30 minutes and about 90 minutes, or for about 45 minutes to about 60 minutes.

At step 512, it can be seen that the staining media utilized in step 510 includes a first amount of cryoprotectant. The cryoprotectant can be a suitable sugar alcohol such as ethylene glycol; glycerol; erythritol; threitol; arabitol; ribitol; xylitol; sorbitol; galactitol; iditol; volemitol; fucitol; inositol; a glycylglycitol, or combinations thereof. The cyroprotectant may also be a suitable glycol, such as propylene glycol, butane triol or combinations thereof. It can be understood that the cyroprotectant selected may be specific to the species of animal, or perhaps even the breed. As an example, glycerol may be selected in the case of bovine sperm and by performing the steps illustrated in FIG. 5 the toxicity of glycerol may be mitigated. It can be appreciated, other suitable cryoprotectants may be utilized if suitable for preserving a sperm sample and that the steps of FIG. 5 may similarly mitigate toxic effects of those cryoprotectants as well.

The first amount of cyroprotectant can be a vol./vol. or wt./vol. concentration of cryoprotectant in the staining media of between about 0.1% and about 5%; between about 0.1% and about 1%; between about 1% and about 2%; between about 2% and about 3%; between about 3% and about 4%; between about 2% and about 4%; or between about 1.5% and about 3%.

Once stained, the sperm sample may be contacted with a sheath fluid in step 520. The step of contacting the sperm sample may be incident to processing the sperm sample, such as by flow cytometry, through a jet-in-air flow cytometer or in a similar process in a microfluidic chip. In one embodiment, the step of contacting the sperm sample with sheath fluid occurs in a jet-in-air flow cytometer, as described with respect to FIG. 1. It can be understood, however, that step 520 is not limited to processing in a jet-in-air flow cytometer, but rather encompasses any method of processing sperm in which a sperm containing sperm sample is contacted with a sheath fluid. As a non-limiting example, sorting on a microfluidic chip generally requires establishing a co-axial flow of sample and sheath fluid through a flow channel. In the case of sperm, a sperm sample would be flown through one or more flow channels in a laminar flow while surrounded by a sheath fluid to focus the location of sperm cells and to prevent them from touching the interior of the flow channel. The laminar flows of the sperm sample and sheath fluid in each channel would prevent, or at least minimize, any mixing of the sperm sample and the sheath fluid while maintaining the fluids in contact.

At step 522, it can be seen that the sheath fluid utilized in step 520 includes a second amount of cryoprotectant. The cryoprotectant can be the same as the cryoprotected in the staining media. Alternatively, the cyroprotectant may be another cryoprotectant such as a suitable sugar alcohol including ethylene glycol; glycerol; erythritol; threitol; arabitol; ribitol; xylitol; sorbitol; galactitol; iditol; volemitol; fucitol; inositol; a glycylglycitol, or combinations thereof or a suitable glycol, such as propylene glycol, butane triol or combinations thereof. The sheath fluid can include a second amount of cryoprotectant between about 0.1% and about 2% cryoprotectant by vol./vol. or wt./vol.; between about 2% and about 4% cryoprotectant by vol./vol. or wt./vol.; between about 4% and about 6% cryoprotectant by vol./vol. or wt./vol.; between about 1% and about 2% cryoprotectant by vol./vol. or wt./vol.; between about 2% and about 3% cryoprotectant by vol./vol. or wt./vol.; between about 3% and about 4% cryoprotectant by vol./vol. or wt./vol.; between about 4% and about 5% cryoprotectant by vol./vol. or wt./vol.; between about 5% and about 6% cryoprotectant by vol./vol. or wt./vol.; between about 2% and about 6% cryoprotectant by vol./vol. or wt./vol.; or between about 3% and about 5% cryoprotectant by vol./vol. or wt./vol.. In one embodiment, the second amount of cryoprotectant in the sheath fluid is about the same as the first amount of cryoprotectant found in the staining media. In an alternative embodiment, the second amount of cryoprotectant in the sheath fluid is at a greater vol./vol. or wt./vol. concentration as compared to the first amount of cryoprotectant in the staining media. In still another embodiment, the vol./vol. or wt./vol. concentration of cryoprotectant in both the staining media and in the sheath fluid can be coordinated to arrive at a desired concentration of cryoprotectant.

At step 530, the sperm sample is manipulated. In one embodiment the sperm sample is manipulated to produce a manipulated sperm sample having a manipulated ratio of viable X-chromosome bearing sperm to viable Y-chromosome bearing sperm. The step of manipulating can be performed by the physical separation of a subset of cells, such as is the case in the droplet forming embodiment described above with reference to FIG. 1. But the step of manipulating is not so limited and includes fluid switching, or diverting cells in the flow channels of microfluidic chips. Alternatively, a photo-damaging laser could be used in conjunction with either a jet-in-air flow cytometer or a microfluidic chip to incapacitate selected sperm cells in the sperm sample, leaving a manipulated sperm sample having a manipulated ratio of viable X-chromosome bearing sperm to viable Y-chromosome bearing sperm. Alternatively, the sperm sample may be manipulated based on other characteristics. As but one example, a sperm sample may be flowed through a flow cytometer to separate presumably viable sperm from sperm with compromised membranes.

One embodiment of the method depicted in FIG. 5 ends at the production of a manipulated sperm sample of step 530, while other embodiments of the method continue on to the step of collecting the manipulated sperm sample 540 and/or the step of freezing the manipulated sperm sample 550. In one embodiment, the method of FIG. 5 optionally proceeds to step 540, wherein the manipulated sperm sample is collected in a collection media. In the case of flow cytometry, the collection media may be described as a catch fluid located in a collection vessel or a catch tube into which selected sperm are deflected. As can be understood from step 542, the collection media in this embodiment also optionally contains an amount of cryoprotectant, which may be considered a third amount of cryoprotectant. Again, the cryoprotectant can be the same as the cryoprotected in the staining media and/or in the sheath fluid. Alternatively, the cyroprotectant may be another cryoprotectant such as a suitable sugar alcohol including ethylene glycol; glycerol; erythritol; threitol; arabitol; ribitol; xylitol; sorbitol; galactitol; iditol; volemitol; fucitol; inositol; a glycylglycitol, or combinations thereof or a suitable glycol, such as propylene glycol, butane triol or combinations thereof. The collection media can include a third amount of cryoprotectant between about 1% and about 2% cryoprotectant by vol./vol. or wt./vol.; between about 2% and about 4% cryoprotectant by vol./vol. or wt./vol.; between about 4% and about 6% cryoprotectant by vol./vol. or wt./vol.; between about 6% and about 8% cryoprotectant by vol./vol. or wt./vol.; between about 3% and about 7% cryoprotectant by vol./vol. or wt./vol.; or between about 3.5% and about 5.5% cryoprotectant by vol./vol. or wt./vol..

In certain embodiments of the invention, a cryoprotectant is included only in the sheath fluid, and is not present in the staining media or the collection media. In another embodiment of the invention, a cryoprotectant is included in the sheath fluid, in the staining media and in the freezing media, but is not included in the collection media.

In one embodiment, the method proceeds from the step of manipulating the sperm sample 530 directly to the step of freezing the manipulated sperm sample 550. For example, in the case of manipulation of the sperm sample with a microfluidic chip a collection media may not be necessary, as no droplets are formed which require the cushioning of a collection media. However, embodiments are envisioned in which a collection media is used in connection with manipulating a sperm sample on a microfluidic chip.

For the method embodied by FIG. 5, the freezing of step 550 may be achieved by a conventional technique, such as those described in WO/200137655. By way of an example only, one such method may begin by extending the manipulated sperm sample to be frozen in an A Fraction. Alternatively, the manipulated sperm sample could have been collected in a collection media including A Fraction extender in the collection step 540. By way of example only, the A fraction can comprise a TRIS citrate extender with 20% egg yolk. Other suitable extenders can include sodium citrate, Tris[hydroxymethyl]aminomethane, and TES (N-Tris [Hydroxymethyl]methyl-2-aminoethanesulfonic acid), and monosodium glutamate buffers; milk; HEPES-buffered medium; and any combination thereof.

The freezing step 550 may continue with cooling the manipulated sperm sample. The manipulated sperm sample can be cooled to a temperature between about 8° C. and 4° C. At one specific example, the manipulated sperm sample can be cooled to about 5° C. Following cooling, a B fraction can be added in one or more steps and then the manipulated sperm sample can be reconcentrated. Reconcentration may include centrifuging the manipulated sperm sample down to a pellet and resuspending the sperm in a final extender, sometimes called an AB extender. As one example, the AB extender may have a concentration of cryoprotectant which is one half the concentration of the cryoprotectant in the B fraction. As a non-limiting example, that concentration may be about 6% in the case of glycerol. Other methods of freezing are contemplated for use in accordance with the embodiment depicted in FIG. 5. In particular, certain methods of freezing described below may provide a synergy with the processing method depicted in FIG. 5.

Figure 6:
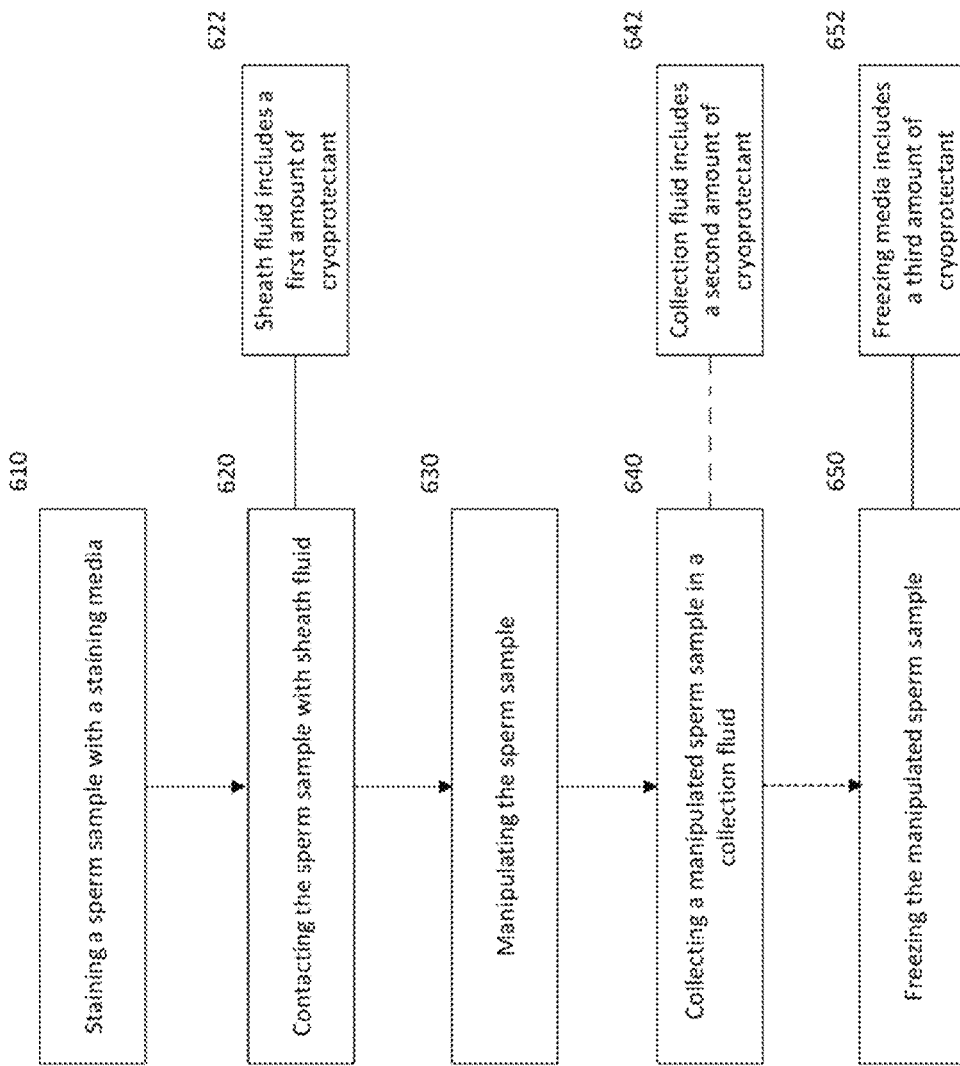

The method depicted in FIG. 6 largely reflects the method depicted in FIG. 5, except that the staining media is not provided with a cryoprotectant. At step (610) the method begins with the step of staining a sperm sample in a staining media. The sperm sample may be neat semen or sperm extended in another solution, such as a those described previously. As an example, the sperm sample may be standardized by extension and reconcentration in the manner described previously. Alternatively, the sperm sample may take the form of neat semen, or neat semen extended with a buffer and and/or having antibiotics added.

Whether standardized or not, the DNA selective fluorescent dye may be Hoechst 33342 supplied in a modified TALP buffer (Table 1). The staining step itself may be performed in a single dilution which additionally includes a quenching dye. Alternatively, step 510 may be performed in two dilutions, such as in a first dilution with a modified TALP having the DNA selective fluorescent dye followed by a second dilution in a modified TALP having a quenching dye. It can be understood other DNA selective fluorescent dyes and other quenching dyes may be used in accordance with this example. For the purpose of this embodiment, each will be referred to as a staining media.

Regardless of where achieved in one dilution or two, the sperm sample can be diluted to between $640 \times 10^6$ and $40 \times 10^6$ sperm/ml, to between about $320 \times 10^6$ and $80 \times 10^6$ sperm/ml, to about $160 \times 10^6$ sperm/ml or to about $120 \times 10^6$ sperm/ml in the staining media. The DNA selective fluorescent dye can be added to the sperm suspended in the staining media in a concentration of between about 10 μM and 200 μM; between about 20 μM and 100 μM, or between about 30 μM and 70 μM. The pH of the staining media can be between about 6.8 and 7.9; about 7.1 and 7.6; or at about 7.4. In the case of two dilutions, the second dilution can be performed at or near the same pH as the first dilution or at a low pH, such as between 5.0 and 6.0, or at about 5.5. Optionally, the previously described antioxidants and concentrations may be incorporated into the staining media. The sperm sample can be incubated between 30-39° C., between about 32-37° C., or at about 34° C. The period of incubation can range between about 20 minutes and about three hours, between about 30 minutes and about 90 minutes, or for about 45 minutes to about 60 minutes.

Once stained, the sperm sample may be contacted with a sheath fluid in step 620. The step of contacting the sperm sample may be incident to processing the sperm sample, such as by flow cytometry, through a jet-in-air flow cytometer or in a similar process in a microfluidic chip. In one embodiment, the step of contacting the sperm sample with sheath fluid occurs in a jet-in-air flow cytometer, as described with respect to FIG. 1. It can be understood, however, that step 620 is not limited to processing in a jet-in-air flow cytometer, but rather encompasses any method of processing sperm in which a sperm containing sperm sample is contacted with a sheath fluid. As a non-limiting example, sorting on a microfluidic chip generally requires establishing a co-axial flow of sample and sheath fluid through a flow channel. In the case of sperm, a sperm sample would be flown through one or more flow channels in a laminar flow while surrounded by a sheath fluid to focus the location of sperm cells and to prevent them from touching the interior of the flow channel. The laminar flows of the sperm sample and sheath fluid in each channel would prevent, or at least minimize, any mixing of the sperm sample and the sheath fluid while maintaining the fluids in contact.

At step 622, it can be seen that the sheath fluid utilized in step 620 includes a first amount of cryoprotectant which may be a suitable sugar alcohol including ethylene glycol; glycerol; erythritol; threitol; arabitol; ribitol; xylitol; sorbitol; galactitol; iditol; volemitol; fucitol; inositol; a glycylglycitol, or combinations thereof or a suitable glycol, such as propylene glycol, butane triol or combinations thereof. The first amount of cryoprotectant in the sheath fluid can be between about 0.1% and about 2% cryoprotectant by vol./vol. or wt./vol.; between about 2% and about 4% cryoprotectant by vol./vol. or wt./vol.; between about 4% and about 6% cryoprotectant by vol./vol. or wt./vol.; between about 1% and about 2% cryoprotectant by vol./vol. or wt./vol.; between about 2% and about 3% cryoprotectant by vol./vol. or wt./vol.; between about 3% and about 4% cryoprotectant by vol./vol. or wt./vol.; between about 4% and about 5% cryoprotectant by vol./vol. or wt./vol.; between about 5% and about 6% cryoprotectant by vol./vol. or wt./vol.; between about 2% and about 6% cryoprotectant by vol./vol. or wt./vol.; or between about 3% and about 5% cryoprotectant by vol./vol. or wt./vol.. In one embodiment, the second amount of cryoprotectant in the sheath fluid is about the same as the first amount of cryoprotectant found in the staining media. In an alternative embodiment, the second amount of cryoprotectant in the sheath fluid is at a greater vol./vol. or wt./vol. concentration as compared to the first amount of cryoprotectant in the staining media.

At step 630, the sperm sample is manipulated. In one embodiment the sperm sample is manipulated to produce a manipulated sperm sample having a manipulated ratio of viable X-chromosome bearing sperm to viable Y-chromosome bearing sperm. The step of manipulating can be performed by the physical separation of a subset of cells, such as is the case in the droplet forming embodiment described above with reference to FIG. 1. But the step of manipulating is not so limited and includes fluid switching, or diverting cells in the flow channels of microfluidic chips. Alternatively, a photo-damaging laser could be used in conjunction with either a jet-in-air flow cytometer or a microfluidic chip to incapacitate selected sperm cells in the sperm sample, leaving a manipulated sperm sample having a manipulated ratio of viable X-chromosome bearing sperm to viable Y-chromosome bearing sperm. Alternatively, the sperm sample may be manipulated based on other characteristics. As but one example, a sperm sample may be flowed through a flow cytometer to separate presumably viable sperm from sperm with compromised membranes.

One embodiment of the method depicted in FIG. 6 ends at the production of a manipulated sperm sample of step 630, while other embodiments of the method continue on to the step of collecting the manipulated sperm sample 640 and/or the step of freezing the manipulated sperm sample 650. In one embodiment, the method of FIG. 6 optionally proceeds to step 640, wherein the manipulated sperm sample is collected in a collection media. In the case of flow cytometry, the collection media may be described as a catch fluid located in a collection vessel or a catch tube into which selected sperm are deflected. As can be understood from step 642, the collection media also optionally contains an amount of cryoprotectant, which may be considered a second amount of cryoprotectant. The cryoprotectant can be the same as the cryoprotected in the sheath fluid. Alternatively, the cyroprotectant may be another cryoprotectant such as a suitable sugar alcohol including ethylene glycol; glycerol; erythritol; threitol; arabitol; ribitol; xylitol; sorbitol; galactitol; iditol; volemitol; fucitol; inositol; a glycylglycitol, or combinations thereof or a suitable glycol, such as propylene glycol, butane triol or combinations thereof. The collection media can include a second amount of cryoprotectant between about 1% and about 2% cryoprotectant by vol./vol. or wt./vol.; between about 2% and about 4% cryoprotectant by vol./vol. or wt./vol.; between about 4% and about 6% cryoprotectant by vol./vol. or wt./vol.; between about 6% and about 8% cryoprotectant by vol./vol. or wt./vol.; between about 3% and about 7% cryoprotectant by vol./vol. or wt./vol.; or between about 3.5% and about 5.5% cryoprotectant by vol./vol. or wt./vol..

In one embodiment, the method proceeds from the step of manipulating the sperm sample 630 directly to the step of freezing the manipulated sperm sample 650. For example, in the case of manipulation of the sperm sample with a microfluidic chip a collection media may not be necessary, as no droplets are formed which require the cushioning of a collection media. However, embodiments are envisioned in which a collection media is used in connection with manipulating a sperm sample on a microfluidic chip.

For the method embodied by FIG. 6, the freezing of step 650 may be achieved by a conventional technique, such as those described in WO/200137655. By way of an example only, one such method may begin by extending the manipulated sperm sample to be frozen in an A Fraction. Alternatively, the manipulated sperm sample could have been collected in a collection media including A Fraction extender in the collection step 540. By way of example only, the A fraction can comprise a TRIS citrate extender with 20% egg yolk. Other suitable extenders can include sodium citrate, Tris[hydroxymethyl]aminomethane, and TES (N-Tris [Hydroxymethyl]methyl-2-aminoethanesulfonic acid), and monosodium glutamate buffers; milk; HEPES-buffered medium; and any combination thereof.

The freezing step 650 may continue with cooling the manipulated sperm sample. The manipulated sperm sample can be cooled to a temperature between about 8° C. and 4° C. At one specific example, the manipulated sperm sample can be cooled to about 5° C. Following cooling, a B fraction can be added in one or more steps and then the manipulated sperm sample can be reconcentrated. Reconcentration may include centrifuging the manipulated sperm sample down to a pellet and resuspending the sperm in a final extender, sometimes called an AB extender. As one example, the AB extender may have a concentration of cryoprotectant which is one half the concentration of the cryoprotectant in the B fraction. As a non-limiting example, that concentration may be about 6% vol./vol. or wt./vol. in the case of glycerol.

Other methods of freezing are contemplated for use in accordance with the embodiment depicted in FIG. 6. In particular, certain methods of freezing described below may provide a synergy with the processing method depicted in FIG. 6.

Figure 7:
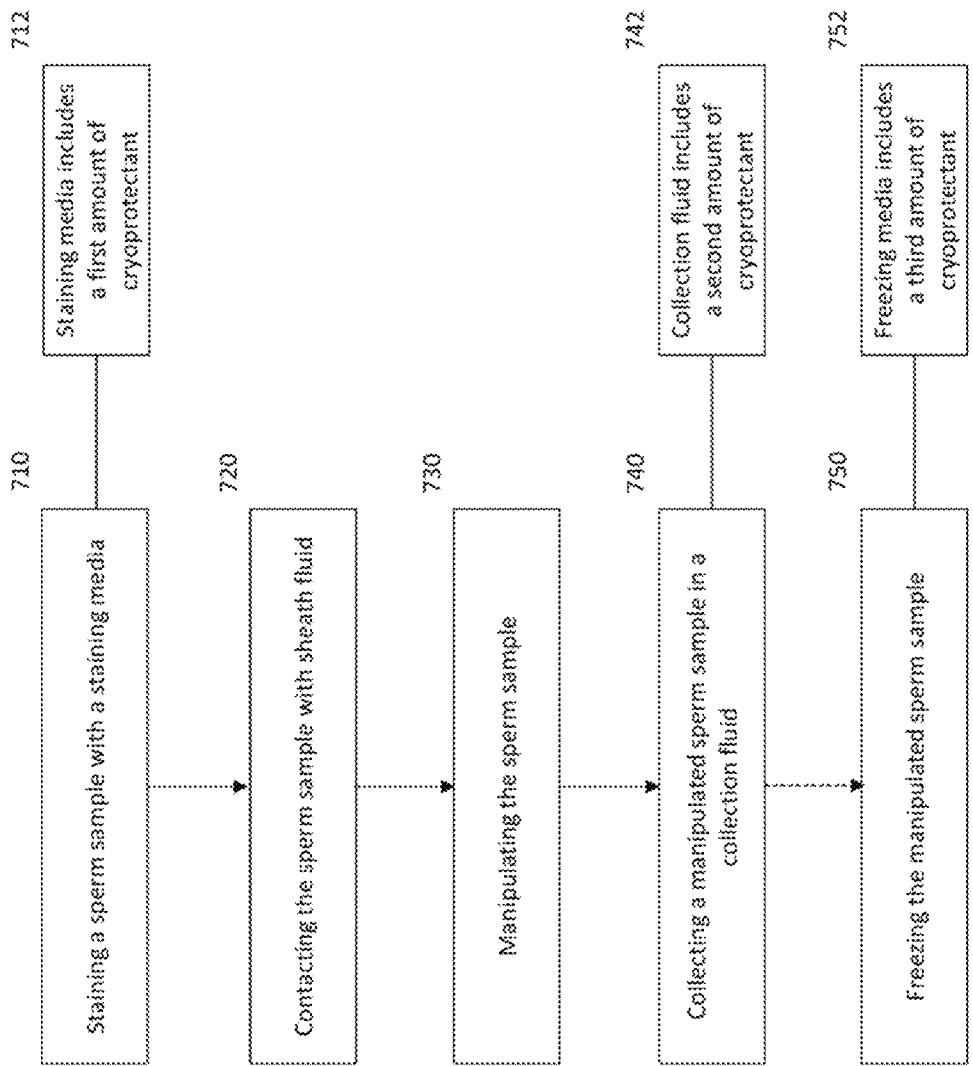

The method depicted in FIG. 7 differs from the method depicted in FIG. 5 in that the sheath fluid is not supplemented with cryoprotectant. At step (710) the method begins with the step of staining a sperm sample in a staining media. The sperm sample may be neat semen or sperm extended in another solution, such as a those described previously. As an example, the sperm sample may be standardized by extension and reconcentration in the manner described previously. Alternatively, the sperm sample may take the form of neat semen, or neat semen extended with a buffer and and/or having antibiotics added.

Whether standardized or not, the DNA selective fluorescent dye may be Hoechst 33342 supplied in a modified TALP buffer (Table 1). The staining step itself may be performed in a single dilution which additionally includes a quenching dye. Alternatively, step 510 may be performed in two dilutions, such as in a first dilution with a modified TALP having the DNA selective fluorescent dye followed by a second dilution in a modified TALP having a quenching dye. It can be understood other DNA selective fluorescent dyes and other quenching dyes may be used in accordance with this example. For the purpose of this embodiment, each will be referred to as a staining media.

Regardless of where achieved in one dilution or two, the sperm sample can be diluted to between 640×10$^6$ and 40×10$^6$ sperm/ml, to between about 320×10$^6$ and 80×10$^6$ sperm/ml, to about 160×10$^6$ sperm/ml or to about 120×10$^6$ sperm/ml in the staining media. The DNA selective fluorescent dye can be added to the sperm suspended in the staining media in a concentration of between about 10 μM and 200 μM; between about 20 μM and 100 μM, or between about 30 μM and 70 μM. The pH of the staining media can be between about 6.8 and 7.9; about 7.1 and 7.6; or at about 7.4. In the case of two dilutions, the second dilution can be performed at or near the same pH as the first dilution or at a low pH, such as between 5.0 and 6.0, or at about 5.5. Optionally, the previously described antioxidants and concentrations may be incorporated into the staining media. The sperm sample can be incubated between 30-39° C., between about 32-37° C., or at about 34° C. The period of incubation can range between about 20 minutes and about three hours, between about 30 minutes and about 90 minutes, or for about 45 minutes to about 60 minutes.

At step 712, it can be seen that the staining media utilized in step 710 includes a first amount of cryoprotectant. The cryoprotectant can be a suitable sugar alcohol such as ethylene glycol; glycerol; erythritol; threitol; arabitol; ribitol; xylitol; sorbitol; galactitol; iditol; volemitol; fucitol; inositol; a glycylglycitol, or combinations thereof. The cryoprotectant may also be a suitable glycol, such as propylene glycol, butane triol or combinations thereof. It can be understood that the cryoprotectant selected may be specific to the species of animal, or perhaps even the breed. As an example, glycerol may be selected in the case of bovine sperm and by performing the steps illustrated in FIG. 7 the toxicity of glycerol may be mitigated. It can be appreciated, other suitable cryoprotectants may be utilized if suitable for preserving a sperm sample and that the steps of FIG. 7 may similarly mitigate toxic effects of those cryoprotectants as well.

The first amount of cryoprotectant can be a vol./vol. or wt./vol. concentration of cryoprotectant in the staining media of between about 0.1% and about 5%; between about 0.1% and about 1%; between about 1% and about 2%; between about 2% and about 3%; between about 3% and about 4%; between about 2% and about 4%; or between about 1.5% and about 3%.

Once stained, the sperm sample may be contacted with a sheath fluid in step 720. The step of contacting the sperm sample may be incident to processing the sperm sample, such as by flow cytometry, through a jet-in-air flow cytometer or in a similar process in a microfluidic chip. In one embodiment, the step of contacting the sperm sample with sheath fluid occurs in a jet-in-air flow cytometer, as described with respect to FIG. 1. It can be understood, however, that step 720 is not limited to processing in a jet-in-air flow cytometer, but rather encompasses any method of processing sperm in which a sperm containing sperm sample is contacted with a sheath fluid. As a non-limiting example, sorting on a microfluidic chip generally requires establishing a co-axial flow of sample and sheath fluid through a flow channel. In the case of sperm, a sperm sample would be flown through one or more flow channels in a laminar flow while surrounded by a sheath fluid to focus the location of sperm cells and to prevent them from touching the interior of the flow channel. The laminar flows of the sperm sample and sheath fluid in each channel would prevent, or at least minimize, any mixing of the sperm sample and the sheath fluid while maintaining the fluids in contact.

At step 730, the sperm sample is manipulated. In one embodiment the sperm sample is manipulated to produce a manipulated sperm sample having a manipulated ratio of viable X-chromosome bearing sperm to viable Y-chromosome bearing sperm. The step of manipulating can be performed by the physical separation of a subset of cells, such as is the case in the droplet forming embodiment described above with reference to FIG. 1. But the step of manipulating is not so limited and includes fluid switching, or diverting cells in the flow channels of microfluidic chips. Alternatively, a photo-damaging laser could be used in conjunction with either a jet-in-air flow cytometer or a microfluidic chip to incapacitate selected sperm cells in the sperm sample, leaving a manipulated sperm sample having a manipulated ratio of viable X-chromosome bearing sperm to viable Y-chromosome bearing sperm. Alternatively, the sperm sample may be manipulated based on other characteristics. As but one example, a sperm sample may be flowed through a flow cytometer to separate presumably viable sperm from sperm with compromised membranes.

One embodiment of the method depicted in FIG. 7 ends at the production of a manipulated sperm sample of step 730, while other embodiments of the method continue on to the step of collecting the manipulated sperm sample 740 and/or the step of freezing the manipulated sperm sample 750. In one embodiment, the method of FIG. 7 optionally proceeds to step 740, wherein the manipulated sperm sample is collected in a collection media. In the case of flow cytometry, the collection media may be described as a catch fluid located in a collection vessel or a catch tube into which selected sperm are deflected. As can be understood from step 742, the collection media also contains an amount of cryoprotectant, which may be considered a third amount of cryoprotectant. Again, the cryoprotectant can be the same as the cryoprotected in the staining media and/or in the sheath fluid. Alternatively, the cyroprotectant may be another cryoprotectant such as a suitable sugar alcohol including ethylene glycol; glycerol; erythritol; threitol; arabitol; ribitol; xylitol; sorbitol; galactitol; iditol; volemitol; fucitol; inositol; a glycylglycitol, or combinations thereof or a suitable glycol, such as propylene glycol, butane triol or combinations thereof. The collection media can include a third amount of cryoprotectant between about 1% and about 2% cryoprotectant by vol./vol. or wt./vol.; between about 2% and about 4% cryoprotectant by vol./vol. or wt./vol.; between about 4% and about 6% cryoprotectant by vol./vol. or wt./vol.; between about 3% and about 7% cryoprotectant by vol./vol. or wt./vol.; or between about 3.5% and about 5.5% cryoprotectant by vol./vol. or wt./vol., or at about 4.5% cryoprotectant by vol./vol. or wt./vol..

In one embodiment, the method proceeds from the step of manipulating the sperm sample 530 directly to the step of freezing the manipulated sperm sample 750. For example, in the case of manipulation of the sperm sample with a microfluidic chip a collection media may not be necessary, as no droplets are formed which require the cushioning of a collection media. However, embodiments are envisioned in which a collection media is used in connection with manipulating a sperm sample on a microfluidic chip.

For the method embodied by FIG. 7, the freezing of step 750 may be achieved by a conventional technique, such as those described in WO/200137655. By way of an example only, one such method may begin by extending the manipulated sperm sample to be frozen in an A Fraction. Alternatively, the manipulated sperm sample could have been collected in a collection media including A Fraction extender in the collection step 540. By way of example only, the A fraction can comprise a TRIS citrate extender with 20% egg yolk. Other suitable extenders can include sodium citrate, Tris[hydroxymethyl]aminomethane, and TES (N-Tris [Hydroxymethyl]methyl-2-aminoethanesulfonic acid), and monosodium glutamate buffers; milk; HEPES-buffered medium; and any combination thereof.

The freezing step 750 may continue with cooling the manipulated sperm sample. The manipulated sperm sample can be cooled to a temperature between about 8° C. and 4° C. At one specific example, the manipulated sperm sample can be cooled to about 5° C. Following cooling, a B fraction can be added in one or more steps and then the manipulated sperm sample can be reconcentrated. Reconcentration may include centrifuging the manipulated sperm sample down to a pellet and resuspending the sperm in a final extender, sometimes called an AB extender. As one example, the AB extender may have a concentration of cryoprotectant which is one half the concentration of the cryoprotectant in the B fraction. As a non-limiting example, that concentration may be about 6% vol./vol. or wt./vol. in the case of glycerol. Other methods of freezing are contemplated for use in accordance with the embodiment depicted in FIG. 7. In particular, certain methods of freezing described below may provide a synergy with the processing method depicted in FIG. 7.

Figure 8:
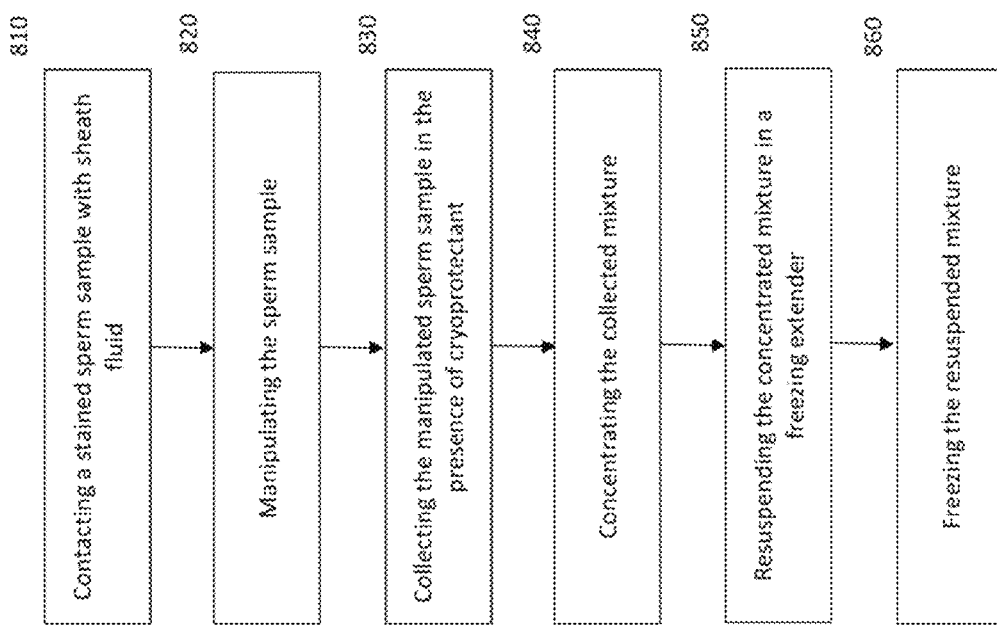
FIG. 8 illustrates an embodiment involving freezing a sperm sample.

FIG. 8 illustrates a new method for freezing sperm, which may be used in conjunction with any of the methods of sorting, or systems, described above in which cryoprotectant is introduced into a process for manipulating a sperm population. As non-limiting examples, the sperm sample can be manipulated to alter the ratio of viable X-chromosome bearing sperm to viable Y-chromosome bearing sperm with a jet-in-air flow cytometer or with a microfluidic chip. The mechanism for manipulating the sperm sample can be droplet deflection, fluid switching, photo-damage with a laser or other means.

Regardless of the means employed to manipulate a sperm sample, the step 810 begins with the collection of a manipulated sperm sample in a mixture which includes cryoprotectant. The cryoprotectant may be present in a container prior to receiving the manipulated sperm sample, of the cryoprotectant may be present in the sperm sample prior to manipulation.

As described previously, in one embodiment sperm are stained in a staining media which includes a cryoprotectant. Similarly, during the manipulation of the sperm sample, the sperm may be contacted with a sheath fluid having a cryoprotectant. Whether stained in a staining media that includes a cryoprotectant or sorted in a system what includes a sheath fluid with a cryoprotectant, or both, the cryoprotectant remains in the sperm sample and is collected at step 810 along with the manipulated sperm cells.

In embodiments in which the sperm is collected with a sufficient concentration of cryoprotectant, the freezing process may be simplified to omit or modify steps that were previously required to effect the gradual introduction of cryoprotectant to the sperm. For example, in one embodiment, manipulated sperm contacted with glycerol-containing staining media, sheath fluid or catch fluid may be taken directly from the sorter, concentrated by centrifugation, resuspended in a cryoprotectant and then cryopreserved. In a further embodiment, after resuspension in the cryoprotectant, the sperm are held for a holding time of less than 24 hours, less than 8 hours, less than 4 hours, 2 hours, less than 2 hours, or less than 1 hour, prior to cryopreservation. In yet a further embodiment, the sperm are cooled during the holding time. In a specific embodiment of the invention, sperm are contacted with sheath fluid comprising 3% glycerol (vol./vol. or wt./vol.), concentrated by centrifugation, resuspended in a cryoprotectant comprising 4.5% glycerol (vol./vol. or wt./vol.) and then cryopreserved. The aforementioned embodiments thus do not include steps of cooling the sperm and addition of cryoprotectant to the cooled sperm, prior to the step of concentrating the sperm.

Set-Up and Conditions for Examples 1-10

Sorter Set-up—All sort analysis and sorting was performed on a modified MoFlo-SX (Beckman Coulter, Brea Calif.) sperm sorter using Genesis digital processing hardware upgrades (available from CytonomeST, Boston, Mass.) and sperm sorting specific software. The Genesis sorting software includes a parameter logging function that records average values for various parameters such as Event Rate (in KHz), Sort Rate (in KHz), Abort Rate (in KHz), dead sperm amount (as rate of dead sperm events divided by Event Rate—in %), live-oriented amount (as rate of live-oriented sperm events divided by Event Rate—in %), X-gated amount (as percent of live oriented sperm chosen to be collected) and Peak-to-Valley Ratio (PVR). Bulk sorting refers to the use of X-gate amount to include both X-chromosome-bearing and Y-chromosome-bearing sperm to provide sperm which are treated by the sorting method but are not sex selected, based on the experience that the quality of sperm after sorting and freezing is not influenced by sex of sperm and bulk sorting is about two times faster than sex sorting. Pressurized sheath fluid was provided either from a sterile bag of sheath fluid inside a pressurized tank with airhead, or from a bag or open beaker of sheath fluid supplying a SheathMaster™ (CytonomeST) precision fluid delivery system where pressure is applied to a small-volume pressurized plenum. In both cases, sheath fluid flow rate is precisely controlled by air pressure controlled by the MoFlo sample station. A TRIS based sheath fluid for commercial production of sexed semen was used for all sorting.

Discontinuous Method of Sheath Fluid Change—A multiple of TRIS based sheath fluid, each containing a specified amount of glycerol, were placed in sterile bags or open beakers and used to supply sorter from pressurized tank or SheathMaster™ fluid delivery system, respectively. The concentration of the glycerol for each sheath fluid is known by its composition.

Staining of Sperm—160 million per mL freshly ejaculated bovine sperm are stained with 65.0 mM Hoechst 33342 in modified TALP for 60 minutes at 34° C., cooled to room temperature, and diluted with ⅓ volume of same modified TALP supplemented with 8% v/v clarified egg yolk to create a final sperm concentration of 120 million sperm per milliliter and an egg yolk concentration of 2% v/v, then filtered through a Partec 50 micron filter.

Alignment of Sperm to Establish/Measure a PVR—PVR (Peak-to-Valley Ratio) is an objective measurement of the univariate plot depicted graphically on the graphic user interface of the Genesis computer running the sorter. The univariate plot of FIG. 3 illustrates the frequency of events having different fluorescence intensities in the forward direction. The representation in a correctly aligned stained sperm sample corresponds to two overlapping curves, with similar numbers of events at two different peak intensities (two maxima), along with a location where the two curves begin to overlap and the number of samples from each of the two curves is about equal (single local minimum about equidistant between the two maximums). The local minimum may be called a valley (V), while the two local maximum may be called peaks (P), the value P as utilized in the example is an average of the two peaks intensity values. Ordinal values for P and V were determined in software, from which a PVR was calculated with the following equation: $((P-V)/P)*100$. Prior to analysis, alignment was performed on the sperm sorter by a trained operator, in order to correct the positioning of the optics, the sperm sorting nozzle and tip, as well the Forward Fluorescence Detector (FAF) and the Side Fluorescence Detector (SAF). In addition, appropriate signal gain must be applied to the FAF and SAF.

Analysis of Logged Data for PVR—The Genesis sorter operation software provides a real-time calculation of the PVR. For each 25,000 events the PVR is calculated and buffered as a raw value, while 100 consecutively occurring PVR raw value measurements are averaged. The average PVR value may be recorded (logged) on demand by the operator. Generally, operating a flow cytometer at lower event rates creates improved PVR ratios due to the improved precision of individual event (sperm) measured values caused by more narrow core sample stream cross section. The alignment was first optimized for sorting at 40,000 events per second, then the sorting gate (examples of which are seen as R1, R3 and R4 in FIG. 4) were applied to collect both the live-X and live-Y populations simultaneously (bulk sort) and the sorter is operated without any further modification for an amount of time corresponding to 500,000 to 700,000 sorted cells before the demand for average value, assuring that the logged parameters are a representative average. After the demand for average value at 40,000 events per second, the operator lowers the stained sperm sample pressure to adjust to a new pressure that established an event rate of about 30,000, with the sorting gate applied to live-X and live-Y populations simultaneously (bulk sort) and the sorter is operated without any further modification for an amount of time corresponding to 500,000 to 700,000 sorted cells before the demand for average value. The same is repeated for a sample running at 20,000 events per second. The sample pressure is then increased to establish an average event rate of 40,000 per second, followed by alignment (if needed) and three consecutive measurements as above. This is done in series over time and the logged data is then analyzed.

Example 1

Table 2 summarizes the treatments for Example 1.

TABLE 2

| | STANDARD. | STAINING | CATCH | VOL SORTED | SORTING | COOLING | FREEZING |
|---|---|---|---|---|---|---|---|
| Control | HOLDING MEDIA (1:3) | TALP 2% EY (120 mill/mL) | TRIS A (3.5 mL) | 20 mL | 0% Gly vol./vol. SF | FREEZING MEDIA (12% Gly vol./vol.) (1:1) | AB (6% Gly vol./vol.) (4 mill/straw) |
| T1 | | | TRIS A (7.0 mL) | 40 mL | 0% Gly vol./vol. SF | — | |
| T2 | | | TRIS A (7.0 mL) | 40 mL | 1% Gly vol./vol. SF | — | |
| T3 | | | TRIS A (7.0 mL) | 40 mL | 2% Gly vol./vol. SF | — | |
| T4 | | | TRIS A (7.0 mL) | 40 mL | 4% Gly vol./vol. SF | — | |
| T5 | | | TRIS A (7.0 mL) | 40 mL | 8% Gly vol./vol. SF | — | |

1. One ejaculate was obtained from a bull.
2. Ejaculate was quality checked (QCed) for motility and morphology and sperm cell concentrations estimated.
3. Ejaculate was standardized by combining with holding media (physiological saline salts and buffer with egg yolk and nutrients) in a 1:3 ratio respectively and then stained in accordance with the above-referenced staining procedure.
4. Control sheath fluid (SF) was connected to flow cytometer and waste fluid was collected in a pre-weighted tube for 3 minutes.
5. Fluid in tube was weighed to determine flow rate with each specific sheath fluid.
6. Stained sample was placed on the sorter and drop delay verified.
7. Logged flow cytometer data was collected for 1 million sperm sex-sorted at 30,000, 20,000 and 40,000 eps.
8. After collection of logged data, 1 catch tube up to 20 mL was bulk sorted.

Figure 9:
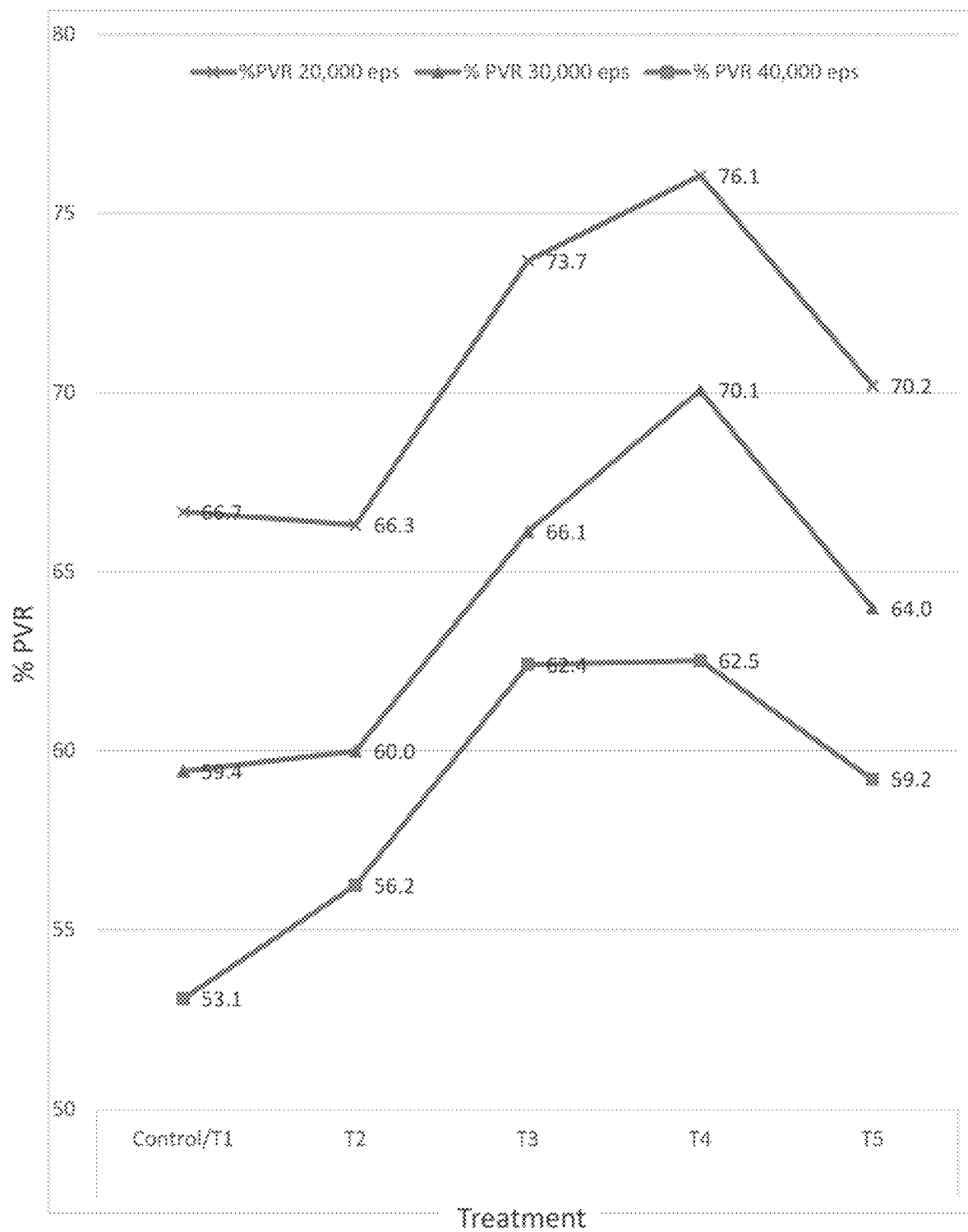
FIG. 9 shows Peak-to-Valley Ratios obtained when using sheath fluid containing varying amounts of glycerol.
Figure 10:
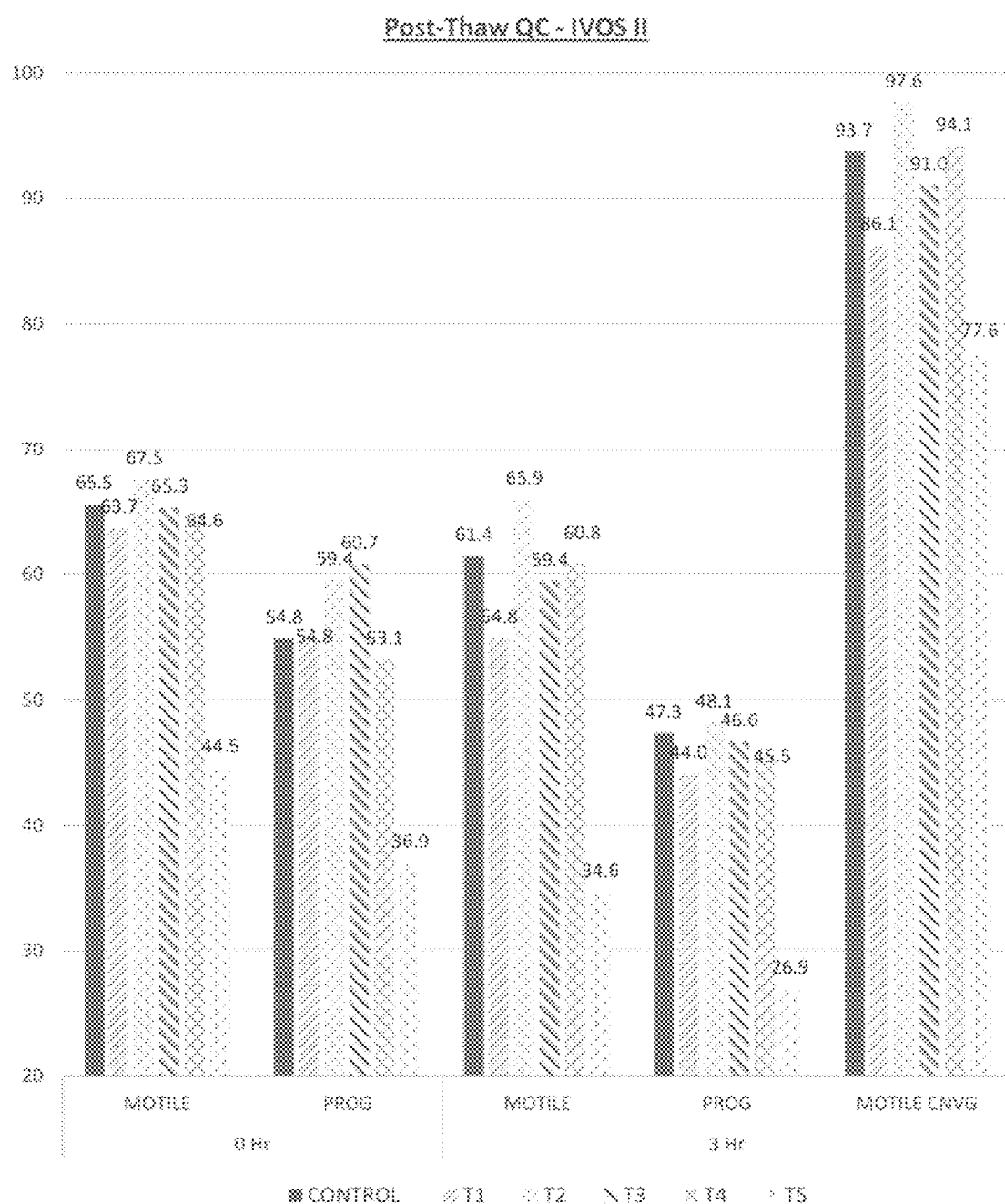
FIG. 10 shows post-thaw motility of sperm sorted using varying amounts of glycerol in sheath fluid.
Figure 11:
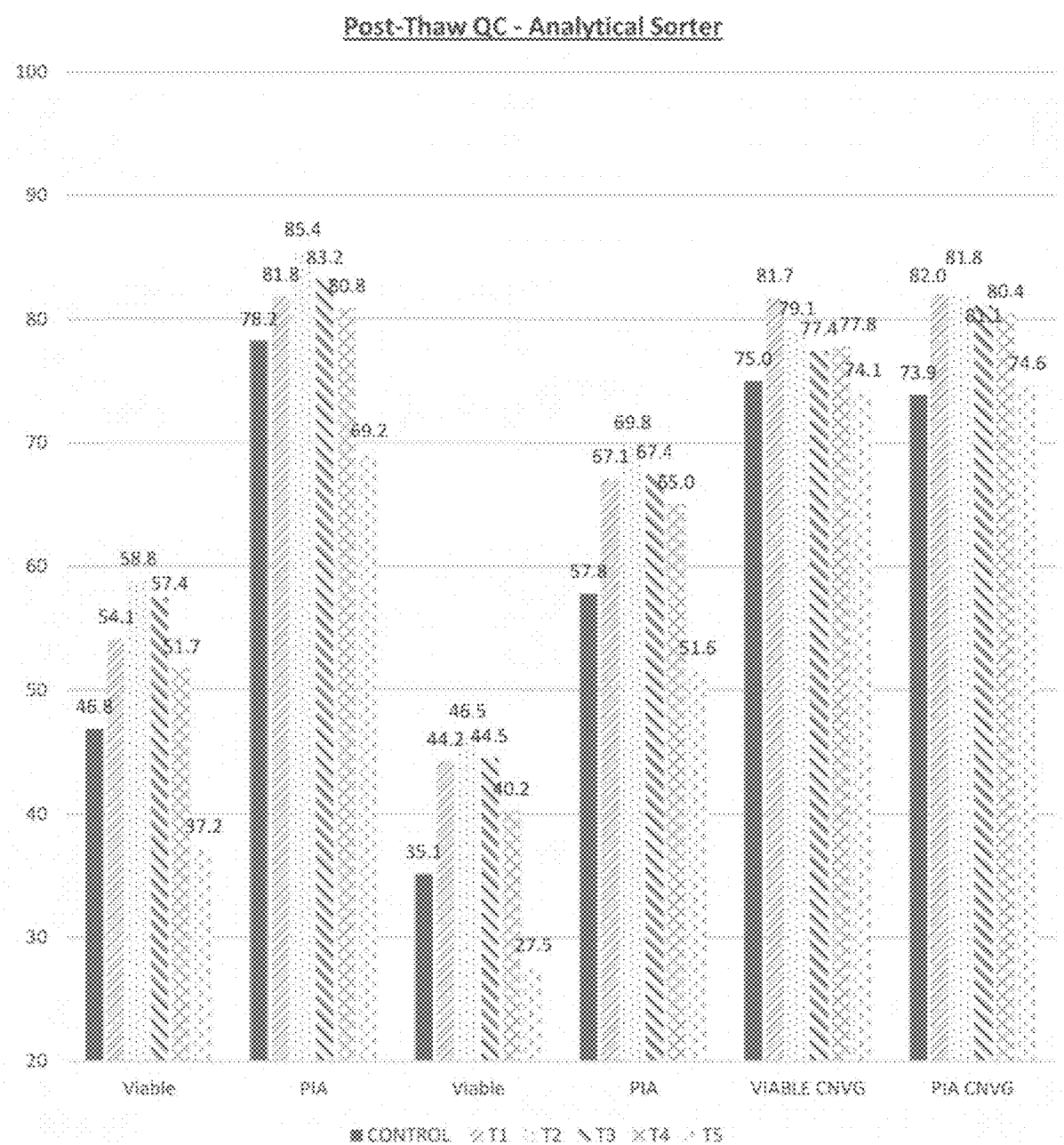
FIG. 11 shows post-thaw viability and percent intact acrosomes (PIA) of sperm sorted using varying amounts of glycerol in sheath fluid.

9. For the treatment groups, steps 7 and 8 were repeated using each treatment sheath fluid described above in Table 2.
10. After collection of logged data, 1 catch tube per treatment up to 40 mL was bulk sorted.
11. All catch tubes were placed in cold room for 90 minutes.
12. 20 mL of freezing media (12% vol./vol. glycerol) was added to the control (two step addition).
13. All catch tubes were centrifuged and supernatant decanted.
14. An appropriate volume of AB (6% glycerol vol./vol.) was added to each catch tube in order to bring the sperm concentration per ¼ cc AI straw to 4 million cells/straw.
15. Diluted sperm were held in cold room overnight.
16. Sperm were placed in straws and cryopreserved.
17. Steps 1-16 were replicated two more times using ejaculates from the same bull.
18. PVR was assessed for the control and each treatment. Results are shown in FIG. 9. Sperm motility (IVOS II), viability (PI) and PIA (PNA) were also assessed at 0 and 3 hours post-thaw. Results are shown in FIGS. 10 and 11, respectively.

Example 2

Instead of the discontinuous method of sheath fluid change described above, Example 2 utilized a gradient sheath fluid method of sheath fluid change as follows.
Gradient Sheath Fluid Method of Sheath Fluid Change—
Beaker 1, providing sheath fluid to SheathMaster™ fluid delivery system containing Bovine Sheath Fluid with 0% glycerol is stirred by magnetic stir bar. Bovine Sheath Fluid containing 6% vol./vol. glycerol (820 mM) in beaker 2 is slowly pumped to Beaker 1 with a peristaltic pump providing a continuously increasing glycerol concentration in Beaker 1 over a period of about 3 hours, where the final glycerol concentration is about 5.5% vol./vol. (750 mM). The concentration of glycerol at time intervals is determined by measuring the osmolarity of the sheath fluid exiting the nozzle and comparing the measurement to an appropriate standard curve. The typical curve for glycerol in sheath fluid is Percent Glycerol (G)=(Measured mOsm (X)−300)/161, or differently stated, each increase in 161 mOsm corresponds to a 1% (vol./vol.) increase in the glycerol concentration.

Figure 12:
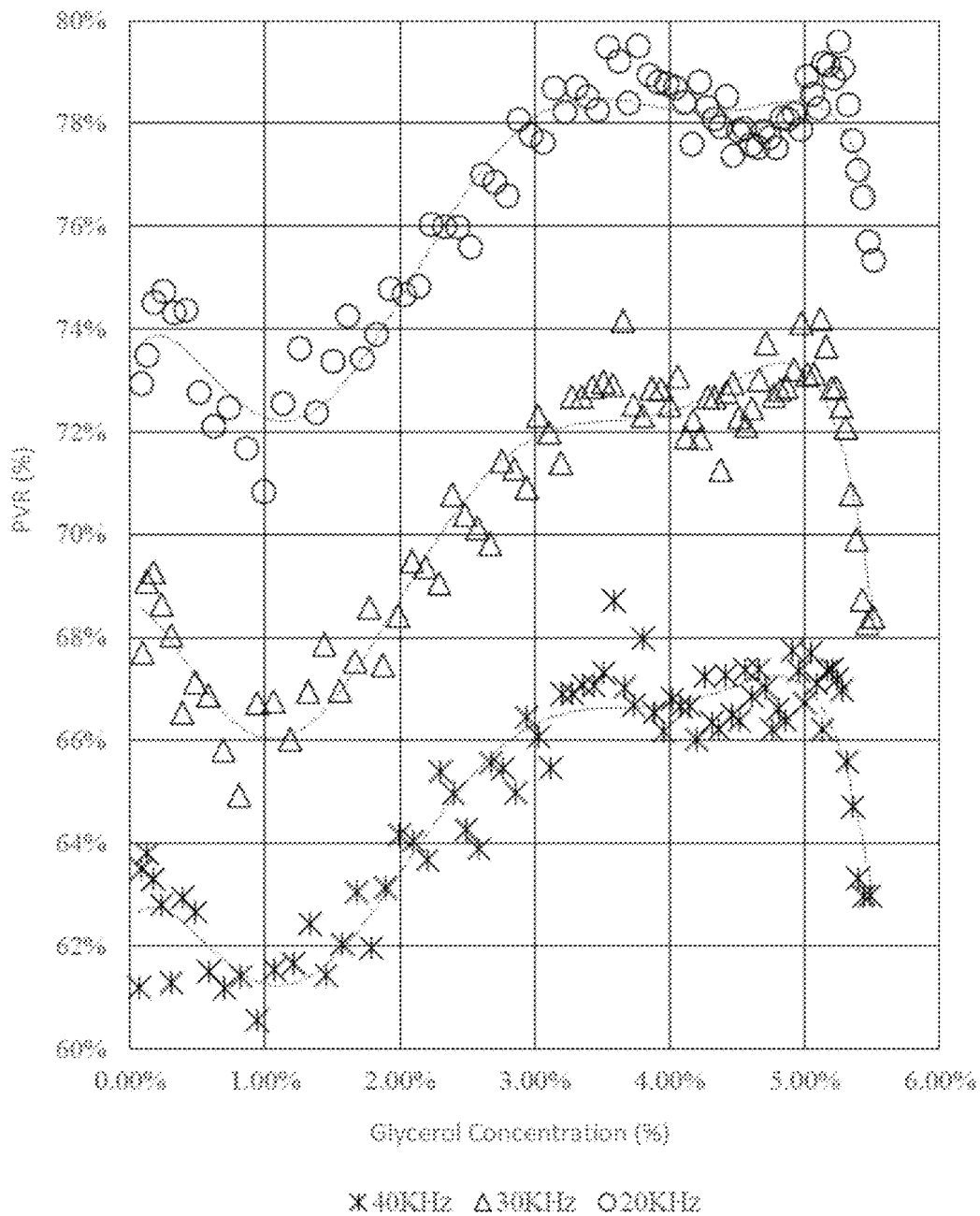
FIG. 12 shows PVRs obtained when using sheath fluid containing varying amounts of glycerol.

1. Fresh ejaculates were obtained from three bulls.
2. Ejaculates were QCed, standardized and stained in accordance with the procedures delineated in Example 1.
3. A beaker containing 0% glycerol sheath fluid was connected the fluid delivery system of a flow cytometer. Fluid was continuously mixed with a magnetic stir bar.
4. Stained sperm sample was placed on the flow cytometer and drop delay verified.
5. 1 million sperm were sex-sorted at 20,000 eps, then 30,000 eps and finally 40,000 eps.
6. 6.0% glycerol vol./vol. sheath fluid was pumped with a peristaltic pump into the 0% glycerol sheath fluid at an average flow rate of 204 g/h.
7. Logged flow cytometer data was continuously collected at the different event rates until only 6.0% glycerol vol./vol. sheath fluid was available.
8. PVR was calculated for each control and treatment sample. The results are shown in FIG. 12.

Example 3

Table 3 summarizes the treatments for Example 3.

TABLE 3

| | STANDARD. | STAIN | CATCH (Volume) | VOL SORTED | SORTING | COOLING MEDIA | COOLING TIME | FREEZING |
|---|---|---|---|---|---|---|---|---|
| Control | HOLDING MEDIA (1:3) | TALP 2% EY (120 mill/mL) | TRIS A (3.5 mL) | 20 mL | 0% Gly vol./vol.SF | FREEZING MEDIA (12% Gly vol./vol.) (1:1) | 90 minutes | COLD AB |
| T1 | | | TRIS A (7.0 mL) | 40 mL | 3.5% Gly vol./vol. SF | — | 90 minutes | |
| T2 | | | TRIS A (7.0 mL) | 40 mL | 3.5% Gly vol./vol. SF | — | 30 minutes | |
| T3 | | | TRIS A (7.0 mL) | 40 mL | 3.5% Gly vol./vol. SF | — | 0 minutes | |
| T4 | | | TRIS A (7.0 mL) | 40 mL | 3.5% Gly vol./vol. SF | — | 0 minutes | RT AB |

1. Ejaculates were obtained from ten bulls.
2. Ejaculates were QCed, standardized and stained in accordance with the procedures delineated in Example 1.
3. 1 catch tube up to 20 mL was bulk sorted.
   Control—Place tubes in cold room for 90 minutes.
   20 mL of freezing media (12% vol./vol. glycerol) added to control (two step addition).
4. Step 3 repeated. 4 catch tubes up to 40 mL were bulk-sorted using 3.5% glycerol vol./vol. sheath fluid (SF).
   Treatment 1—Tubes placed in cold room for 90 minutes.
   Treatment 2—Tubes placed in cold room for 30 minutes.
   Treatment 3—Kept at room temperature until ready to centrifuge
   Treatment 4—Kept at room temperature until ready to centrifuge
5. All catch tubes were centrifuged and supernatant decanted.
6. An appropriate volume of cold AB (6% glycerol vol./vol.) was added to each catch tube in order to bring the sperm concentration per ¼ cc AI straw to 4 million cells/straw, except that room temperature AB was added to treatment 4.
7. Diluted sperm held over-night in cold room.
8. Sperm cells were placed in straws and cryopreserved (3 straws per treatment at 4 million cells/straw).
9. 0 and 3 hr motility (IVOS), viability (PI) and PIA (PNA) were assessed post-thaw. Results are shown in FIG. 13. Convergence (3 hr/0 hr) for motility, viability and PIA are shown in FIG. 14.

Example 4

Table 4 summarizes the treatments for Example 4.

TABLE 4

| | STANDARD. | STAIN | CATCH (Volume) | VOL SORTED | SORTING | COOLING MEDIA | COOLING TIME | FREEZING |
|---|---|---|---|---|---|---|---|---|
| Control | HOLDING MEDIA (1:3) | TALP 2% EY (120 mill/mL) | TRIS A (3.5 mL) | 20 mL | 0% Gly vol./vol. SF | FREEZING MEDIA (12% Gly vol./vol.) (1:1) | 90 minutes | AB (6% Gly vol./vol.) |
| T1 | | | TRIS A (7.0 mL) | 40 mL | 3.0% Gly vol./vol. SF | — | 90 minutes | AB (5% Gly vol./vol.) |
| T2 | | | TRIS A (7.0 mL) | 40 mL | 3.0% Gly vol./vol. SF | — | 0 minutes | AB (5% Gly vol./vol.) |
| T3 | | | TRIS A (7.0 mL) | 40 mL | 5.0% Gly vol./vol. SF | — | 90 minutes | AB (5% Gly vol./vol.) |
| T4 | | | TRIS A (7.0 mL) | 40 mL | 5.0% Gly vol./vol. SF | — | 0 minutes | AB (5% Gly vol./vol.) |

1. Ejaculates were obtained from five bulls.
2. Ejaculates were QCed, standardized and stained in accordance with the procedures delineated in Example 1.
3. 1 catch tube up to 20 mL was bulk sorted.
   Control—catch tubes placed in cold room for 90 minutes. 20 mL of freezing media (12% vol./vol. glycerol) added to control (two step addition).
   All catch tubes were centrifuged and supernatant decanted.
   An appropriate volume of AB (6% glycerol vol./vol.) was added to each catch tube in order to bring the sperm concentration per ¼ cc AI straw to 4 million cells/straw.
4. 3.0% glycerol sheath fluid (SF) connected and tank pressurized.
5. 2 catch tubes up to 40 mL were bulk sorted:
   Treatment 1—catch tubes placed in cold room for 90 minutes.
   Treatment 2—catch tubes placed in cold room for 0 minutes.
6. 5.0% glycerol vol./vol. sheath fluid connected and tank pressurized.
7. 4 catch tubes up to 40 mL bulk sorted:
   Treatment 3—catch tubes placed in cold room for 90 minutes.
   Treatment 4—catch tubes placed in cold room for 0 minutes.

Figure 15:
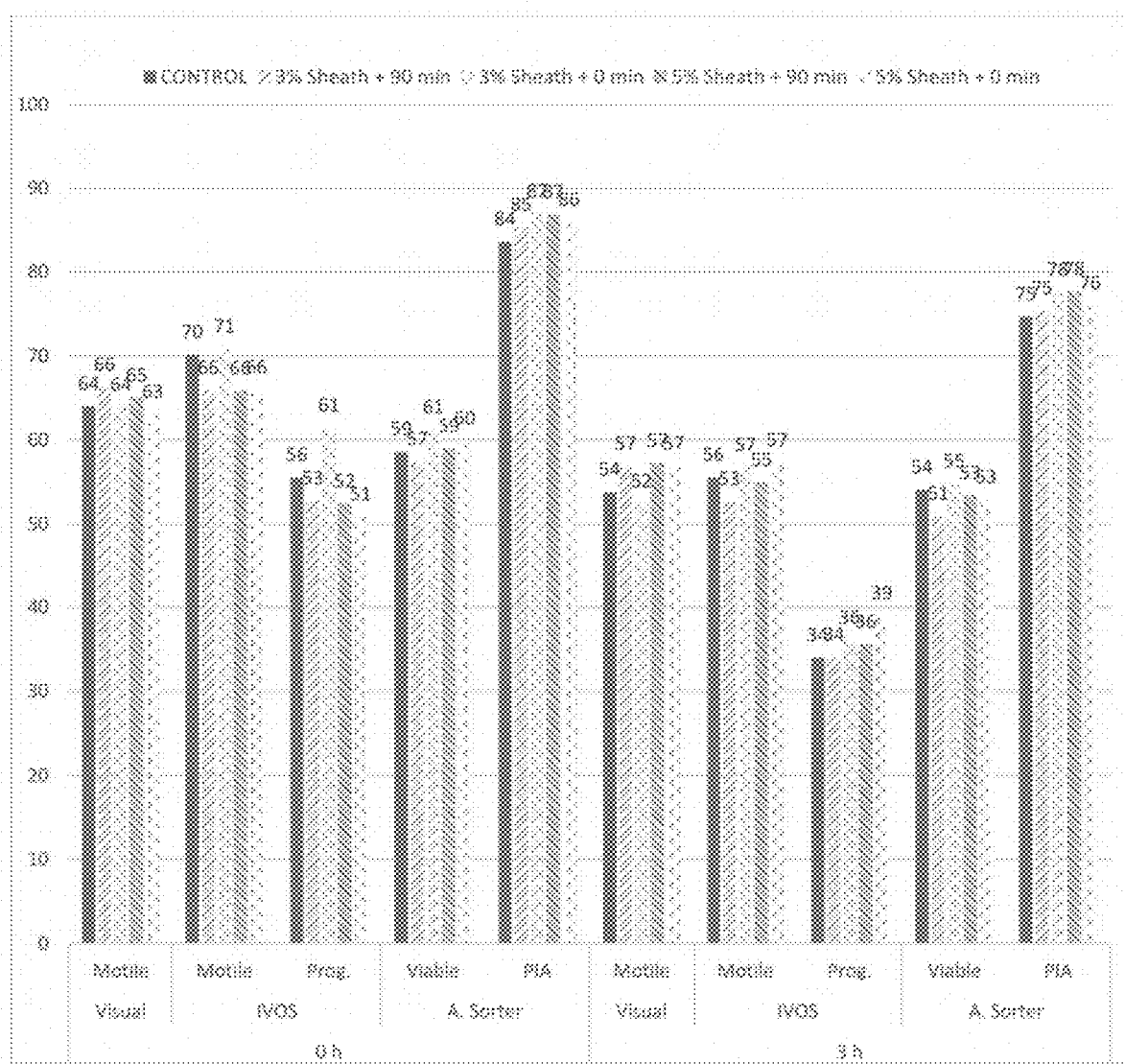
FIG. 15 shows post-thaw motility, viability and PIAs of sperm sorted using varying amounts of glycerol in sheath fluid.
Figure 16:
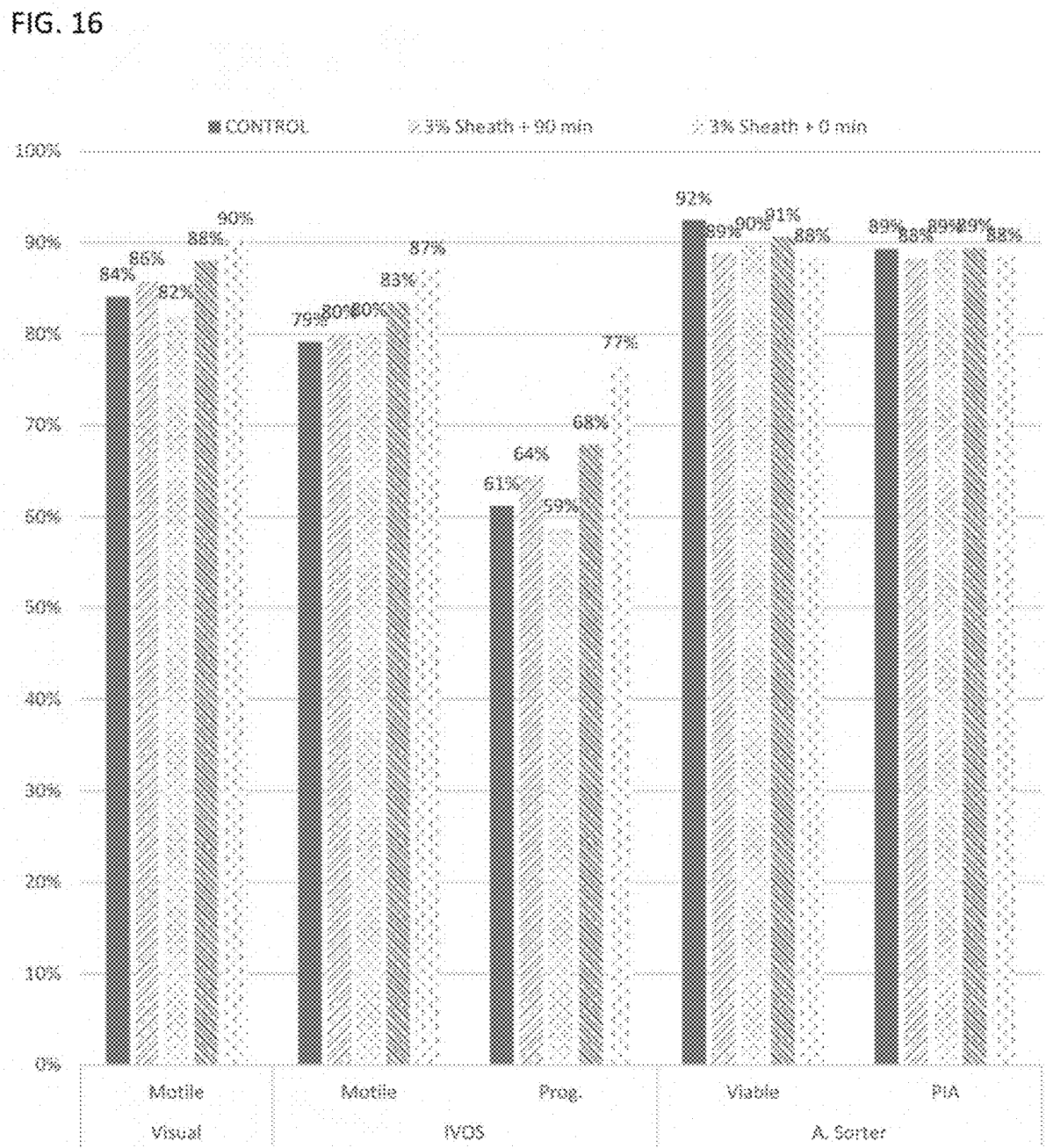
FIG. 16 shows convergence of post-thaw motility, viability and PIAs of sperm sorted using varying amounts of glycerol in sheath fluid.

All tubes centrifuged and supernatant decanted.
AB (5% glycerol vol./vol.) added to each tube for a final of 4 million sperm per straw.
8. Diluted sperm held over-night in cold room.
9. Sperm cells were placed in straws and cryopreserved.
10. 0 and 3 hr motility (IVOS), viability (PI) and PIA (PNA) were assessed post-thaw. Results are shown in FIG. 15. Convergence (3 hr/0 hr) for motility, viability and PIA are shown in FIG. 16.

Example 5

Table 5 summarizes the treatments for Example 5.

TABLE 5

| | Standard.; Stain | Catch Volume | Sort Volume | Concentration in SF (Normalized to Glycerol) | Cooling Time | Cryoprotectant for freezing |
|---|---|---|---|---|---|---|
| Glycerol (Control) | HOLDING MEDIA (1:3); TALP 2% EY (120 mill/mL) | TRIS A (7.0 mL) | 40 mL | 3.5% Gly vol./vol. SF | 0 minutes | 5% Gly vol./vol. AB |
| Ethylene Glycol | | TRIS A (7.0 mL) | 40 mL | 3.5% EG vol./vol. SF | 0 minutes | 5% Gly vol./vol. AB |
| Propylene Glycol | | TRIS A (7.0 mL) | 40 mL | 3.5% PG vol./vol. SF | 0 minutes | 5% Gly vol./vol. AB |
| Erythritol | | TRIS A (7.0 mL) | 40 mL | 3.5% Erythritol vol./vol. SF | 0 minutes | 5% Gly vol./vol. AB |
| Erythritol | | TRIS A (7.0 mL) | 40 mL | 5.0% Erythritol vol./vol. SF | 0 minutes | 5% Gly vol./vol. AB |

1. Ejaculates were obtained from four bulls.
2. Ejaculates were QCed, standardized and stained in accordance with the procedures delineated in Example 1.
3. Sheath fluid control was connected and sheath fluid tank pressurized.
4. Stained sample was placed on a flow cytometer and drop delay verified.
5. 1 catch tube up to 40 mL was bulk sorted using glycerol 3.5% vol./vol. sheath fluid (SF).
6. 1 catch tube up to 40 mL was bulk sorted using ethylene glycol 3.5% vol./vol. SF.
7. 1 catch tube up to 40 mL was bulk sorted using propylene glycol 3.5% vol./vol. SF.

8. 1 catch tube up to 40 mL was bulk sorted using erythritol 3.5% vol./vol. SF 9. 1 catch tube up to 40 mL was bulk sorted using erythritol 5.0% vol./vol. SF.

10. All tubes were centrifuged and decanted.

11. AB 5% glycerol vol./vol. was added to each tube in an amount able to yield 4 million sperm per straw.

12. Diluted sperm was held overnight in cold room.

13. Sperm cells were placed in straws and cryopreserved.

Figure 17:
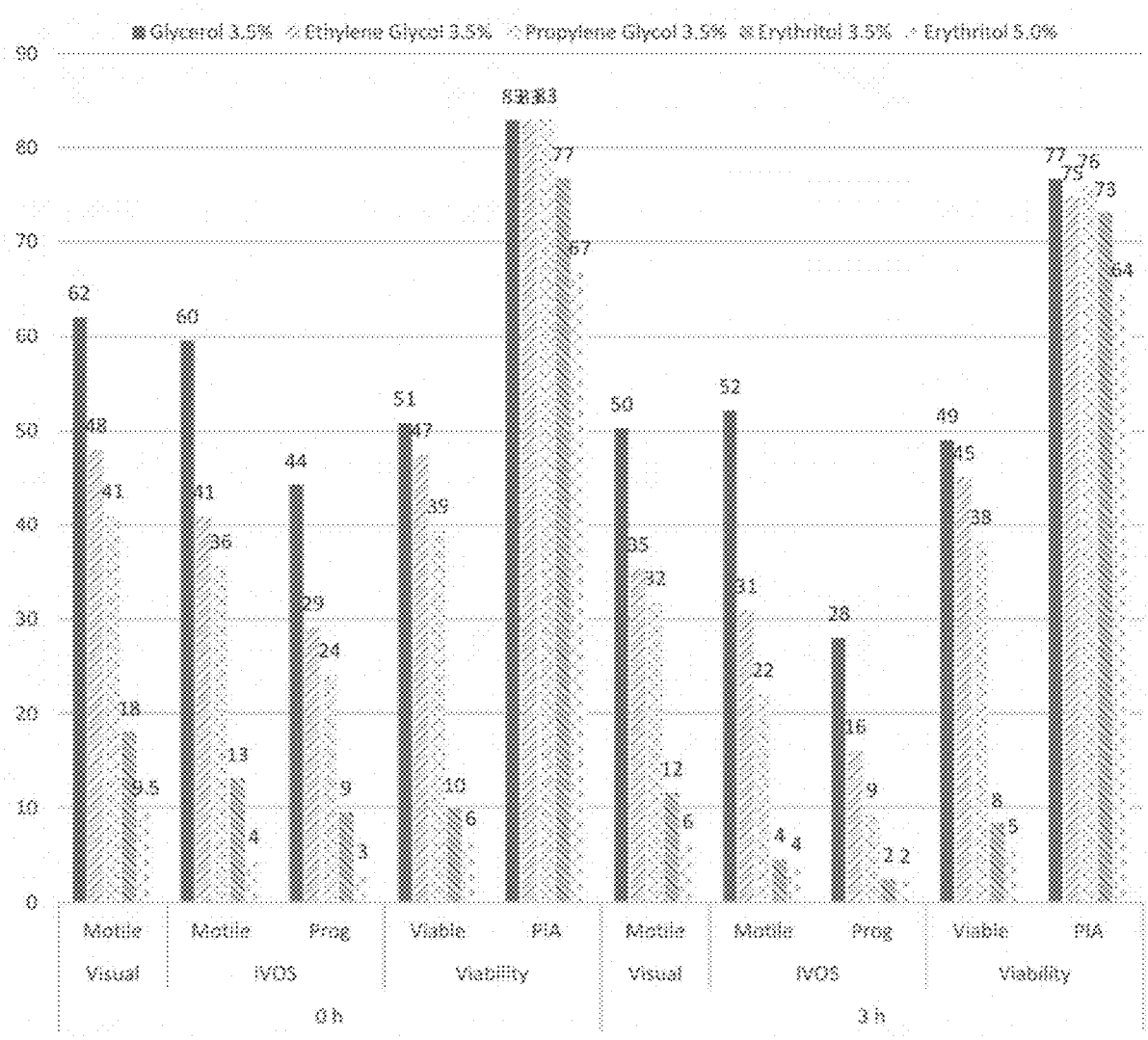
FIG. 17 shows post-thaw motility, viability and PIAs of sperm sorted using different glycols in sheath fluid.
Figure 18:
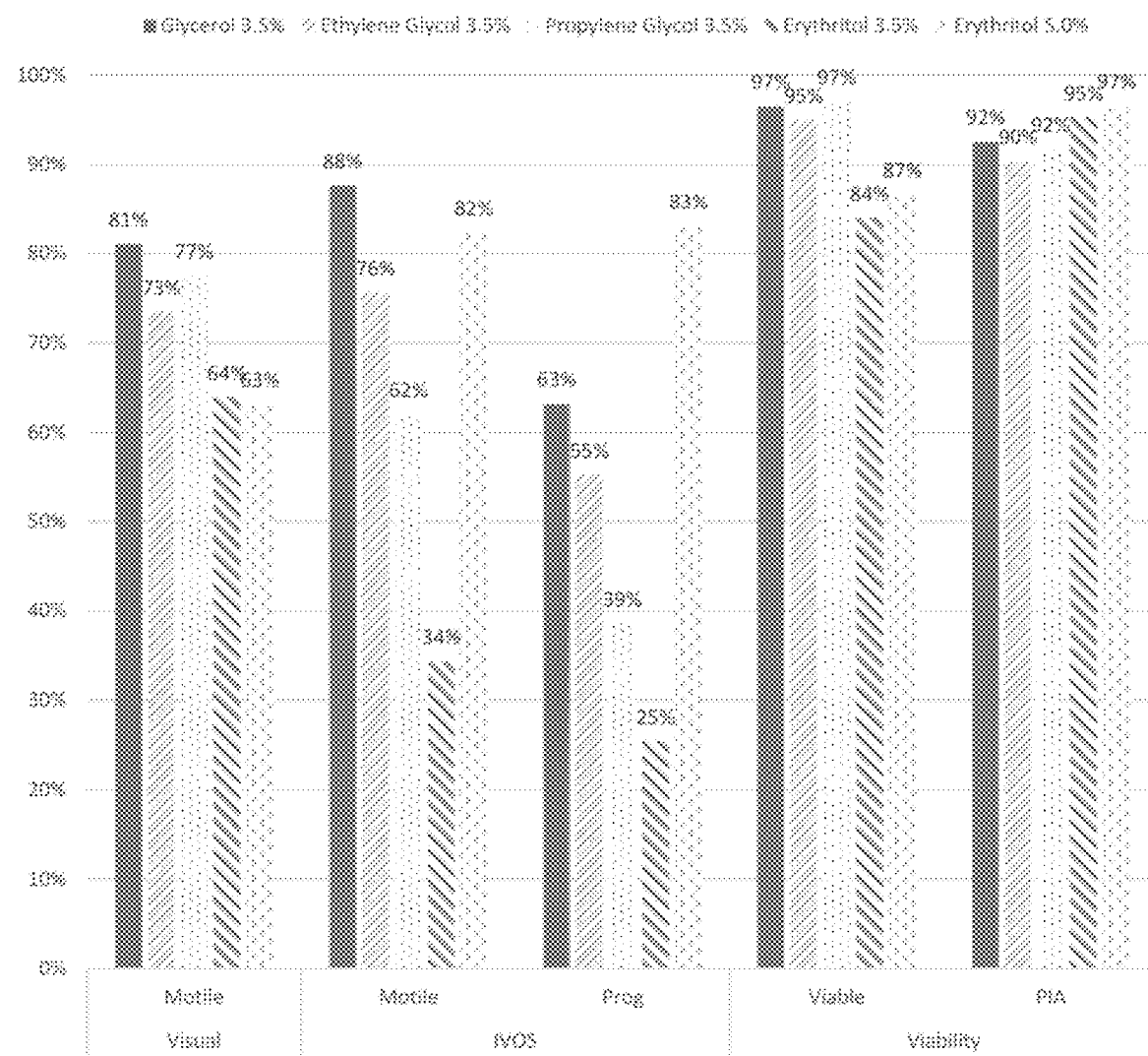
FIG. 18 shows convergence of post-thaw motility, viability and PIAs of sperm sorted using different glycols in sheath fluid.

14. 0 and 3 hr post-thaw motility (IVOS), viability (PI) and PIA (PNA) were assessed. Results are shown in FIG. 17. Convergence (3 hr/0 hr) for motility, viability and PIA are shown in FIG. 18.

Example 6

Table 6 summarizes the treatments for Example 6.

7. 1 catch tube up to 40 mL was bulk sorted using glycerol 3.0% vol./vol. SF (T2)

8. 1 catch tube up to 40 mL was bulk sorted using glycerol 5.0% vol./vol. SF (T3)

9. 1 catch tube up to 40 mL was bulk sorted using glycerol 7.0% vol./vol. SF (T4)

10. Control tubes placed in cold room for 90 minutes and 20 mL of freezing media (12% v/v glycerol) was added (two step addition).

11. All tubes were centrifuged and decanted.

12. Sufficient AB was added to each tube in order to yield 4 million sperm per straw:
AB 6.0% glycerol vol./vol. (Control)
AB 1.0% glycerol vol./vol. (T1)
AB 3.0% glycerol vol./vol. (T2)
AB 5.0% glycerol vol./vol. (T3 and Control 2)
AB 7.0% glycerol vol./vol. (T4)

TABLE 6

|  | STANDARD. | STAIN | Catch Volume | Sort Volume | Gly in sheath | Cooling Time | Cryoprotectant for freezing |
|---|---|---|---|---|---|---|---|
| CONTROL | HOLDING MEDIA (1:3) | TALP 2% EY (120 mill/mL) | TRIS A (3.5 mL) | 20 mL | 0.0% Gly vol./vol. SF | 90 minutes + FREEZING MEDIA (12% Gly vol./vol.) | 6.0% Gly vol./vol. AB |
| CONTROL 2 |  |  | TRIS A (7.0 mL) | 40 mL | 3.0% Gly vol./vol. SF | 0 minutes | 5.0% Gly vol./vol. AB |
| T1 |  |  | TRIS A (7.0 mL) | 40 mL | 1.0% Gly vol./vol. SF | 0 minutes | 1.0% Gly vol./vol. AB |
| T2 |  |  | TRIS A (7.0 mL) | 40 mL | 3.0% Gly vol./vol. SF | 0 minutes | 3.0% Gly vol./vol. AB |
| T3 |  |  | TRIS A (7.0 mL) | 40 mL | 5.0% Gly vol./vol. SF | 0 minutes | 5.0% Gly vol./vol. AB |
| T4 |  |  | TRIS A (7.0 mL) | 40 mL | 7.0% Gly vol./vol. SF | 0 minutes | 7.0% Gly vol./vol. AB |

1. Fresh ejaculates were obtained from four bulls.

2. Ejaculates were QCed, standardized and stained in accordance with the procedures delineated in Example 1.

3. Sheath fluid control was connected and sheath fluid tank pressurized.

4. Bulk sort 1 catch tube up to 40 mL using glycerol 0.0% sheath fluid (SF) (Control)

5. 1 catch tube up to 40 mL was bulk sorted using glycerol 1.0% vol./vol. SF (T1)

6. 1 catch tube up to 40 mL was bulk sorted using glycerol 3.0% vol./vol. SF (Control 2)

13. Diluted sperm was then held overnight in cold room.

14. Sperm cells were placed in straws and cryopreserved.

Figure 19:
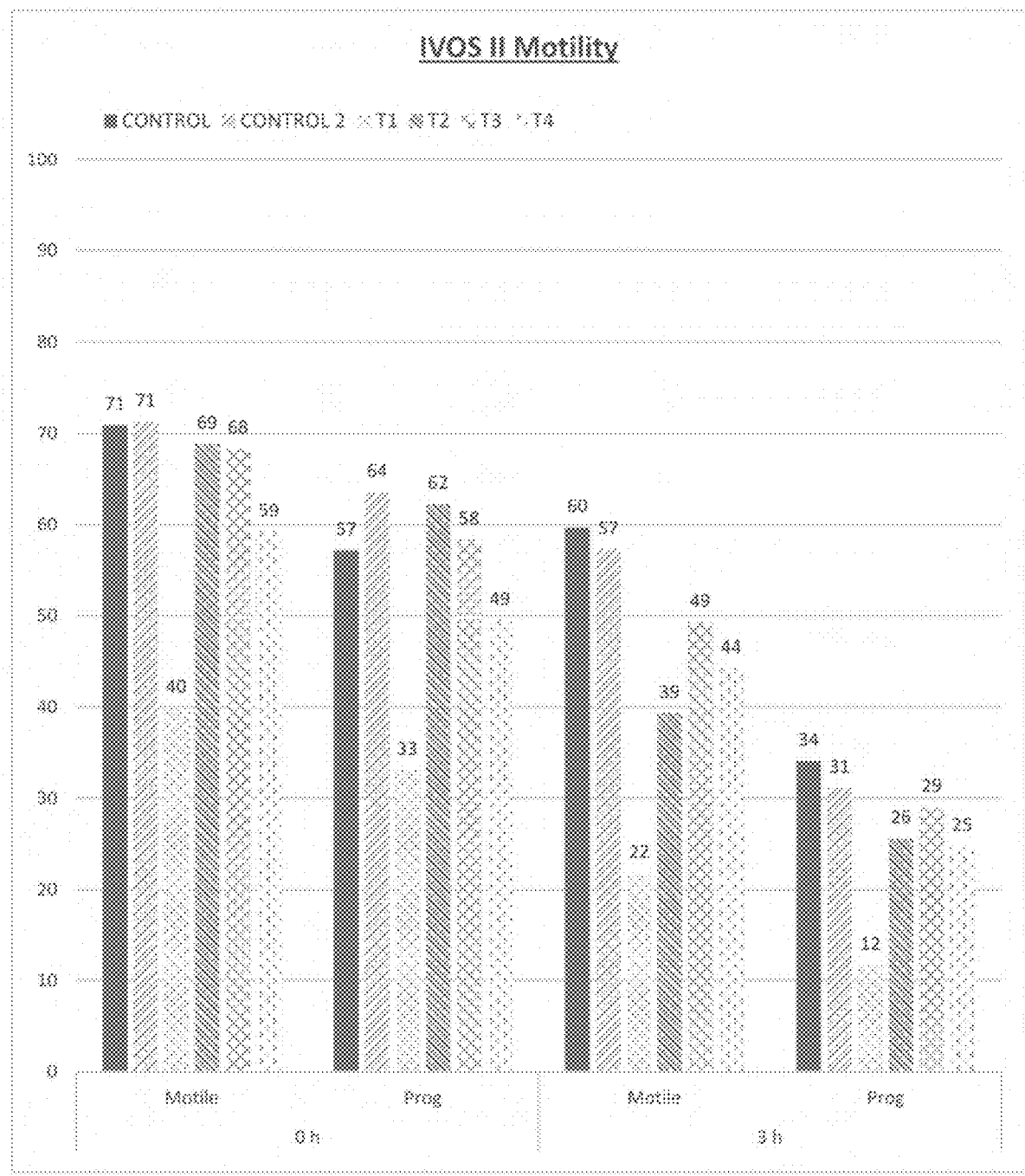
FIG. 19 shows post-thaw motility of sperm sorted using varying amounts of glycerol in sheath fluid.
Figure 20:
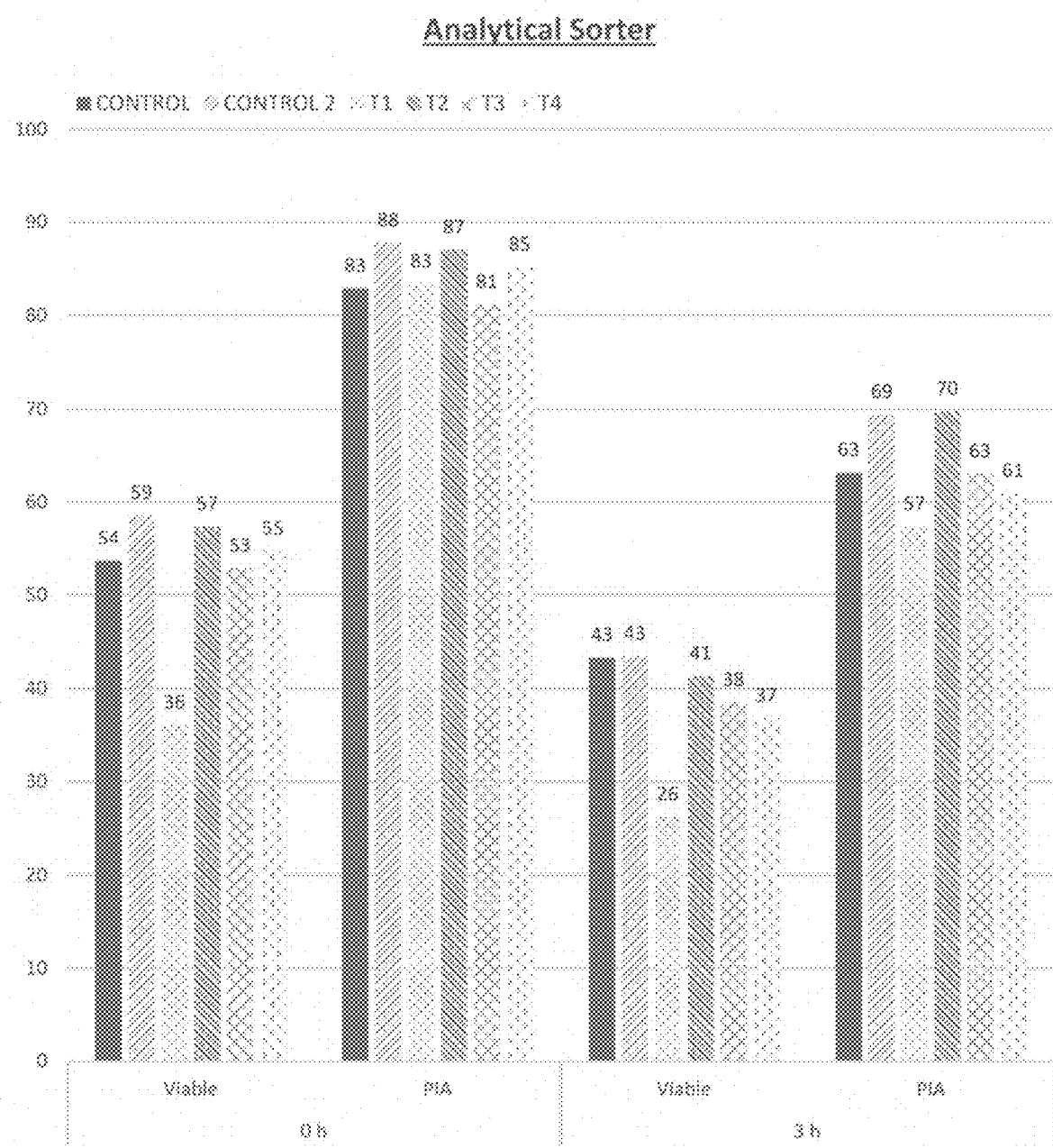
FIG. 20 shows post-thaw viability and PIAs of sperm sorted using varying amounts of glycerol in sheath fluid.

15. 0 and 3 hr post-thaw motility (IVOS II) are shown in FIGS. 19. 0 and 3 hr post-thaw viability (PI) and PIA (PNA) are shown in FIG. 20.

Example 7

Table 7 summarizes the treatments for Example 7.

TABLE 7

|  | STANDARD. | STAIN | Catch Volume | Sort Volume | Polyol in sheath fluid | Cooling Time | Cryoprotectant for freezing |
|---|---|---|---|---|---|---|---|
| CONTROL | HOLDING MEDIA (1:3) | TALP 2% EY (120 mill/mL) | TRIS A (3.5 mL) | 20 mL | 0.0% Gly vol./vol. SF | 90 minutes + FREEZING MEDIA (12% Gly) | 6.0% Gly vol./vol. AB |
| CONTROL 2 |  |  | TRIS A (7.0 mL) | 40 mL | 3.0% Gly vol./vol. SF | 0 minutes | 5.0% Gly vol./vol. AB |

TABLE 7-continued

| STANDARD. | STAIN | Catch Volume | Sort Volume | Polyol in sheath fluid | Cooling Time | Cryoprotectant for freezing |
|---|---|---|---|---|---|---|
| T1 | | TRIS A (7.0 mL) | 40 mL | 1.0% Propylene Glycol vol./vol. SF | 0 minutes | 1.0% Prop. Glycol vol./vol. AB |
| T2 | | TRIS A (7.0 mL) | 40 mL | 3.0% Propylene Glycol vol./vol. SF | 0 minutes | 3.0% Prop. Glycol vol./vol. AB |
| T3 | | TRIS A (7.0 mL) | 40 mL | 5.0% Propylene Glycol vol./vol. SF | 0 minutes | 5.0% Prop. Glycol vol./vol. AB |
| T4 | | TRIS A (7.0 mL) | 40 mL | 7.0% Propylene Glycol vol./vol. SF | 0 minutes | 7.0% Prop. Glycol vol./vol. AB |

1. Fresh ejaculates were obtained from four bulls.
2. Ejaculates were QCed, standardized and stained in accordance with the procedures delineated in Example 1.
3. Sheath fluid control was connected and sheath fluid tank pressurized.
4. 1 catch tube up to 20 mL was bulk sorted using glycerol 0.0% vol./vol. sheath fluid (SF) (Control)
5. 1 catch tube up to 40 mL was bulk sorted using glycerol 3.0% vol./vol. SF (Control 2)
6. 1 catch tube up to 40 mL was bulk sorted using propylene glycol 1.0% vol./vol. SF (T1)
7. 1 catch tube up to 40 mL was bulk sorted using propylene glycol 3.0% vol./vol. SF (T2)
8. 1 catch tube up to 40 mL was bulk sorted using propylene glycol 5.0% vol./vol. SF (T3)
9. 1 catch tube up to 40 mL was bulk sorted using propylene glycol 7.0% vol./vol. SF (T4)
10. Control tubes placed in cold room for 90 minutes and 20 mL of freezing media (12% vol//vol. glycerol) was added (two step addition).
11. All tubes were centrifuged and decanted.
12. Sufficient AB was added to each tube in order to yield 4 million sperm per straw:

AB 6.0% glycerol vol./vol. (Control)
AB 5.0% glycerol vol./vol. (Control 2)
AB 1.0% propylene glycol vol./vol. (T1)
AB 3.0% propylene glycol vol./vol. (T2)
AB 5.0% propylene glycol vol./vol. (T3)
AB 7.0% propylene glycol vol./vol. (T4)

Figure 21:
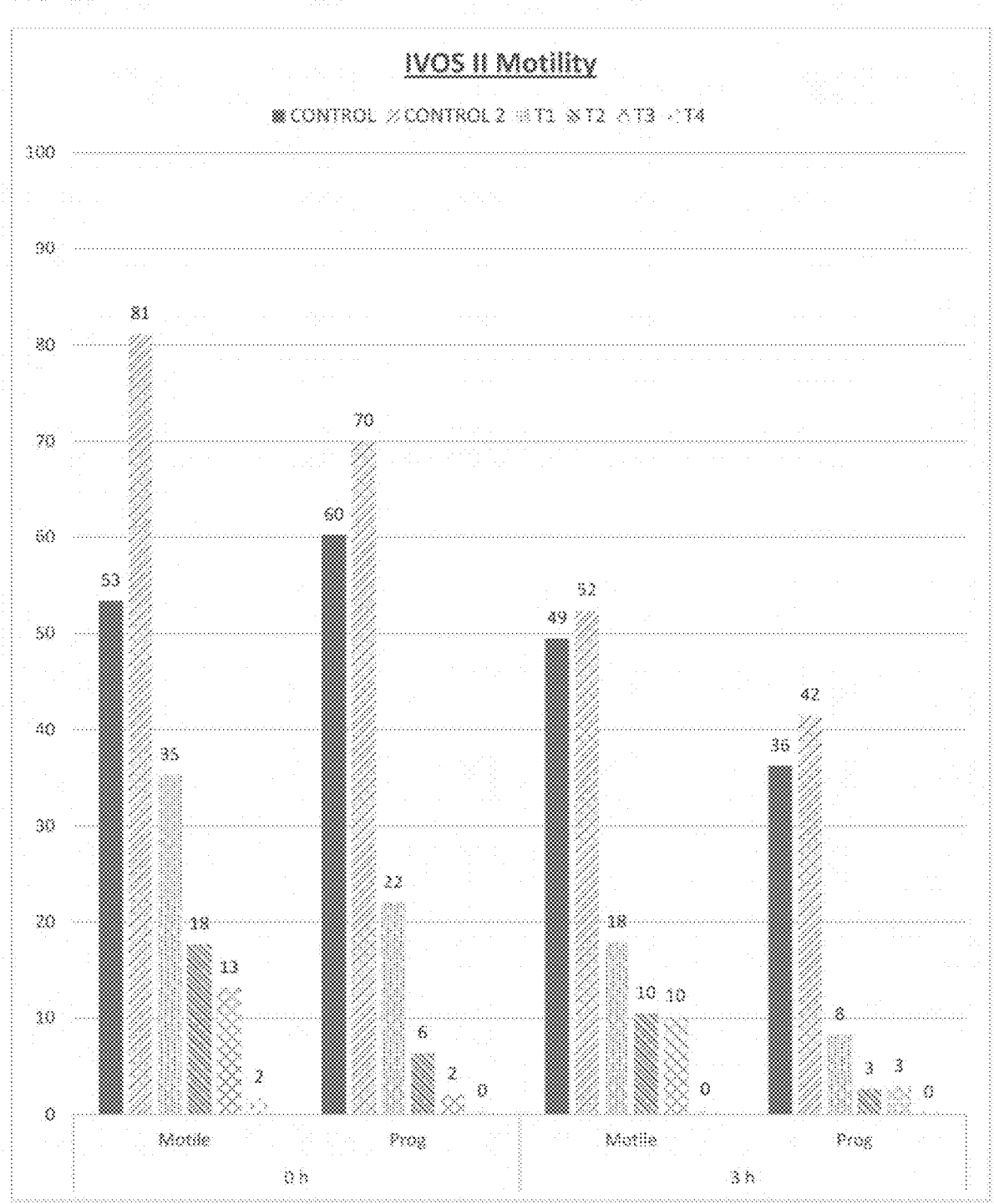
FIG. 21 shows post-thaw motility of sperm sorted using different glycols in sheath fluid.
Figure 22:
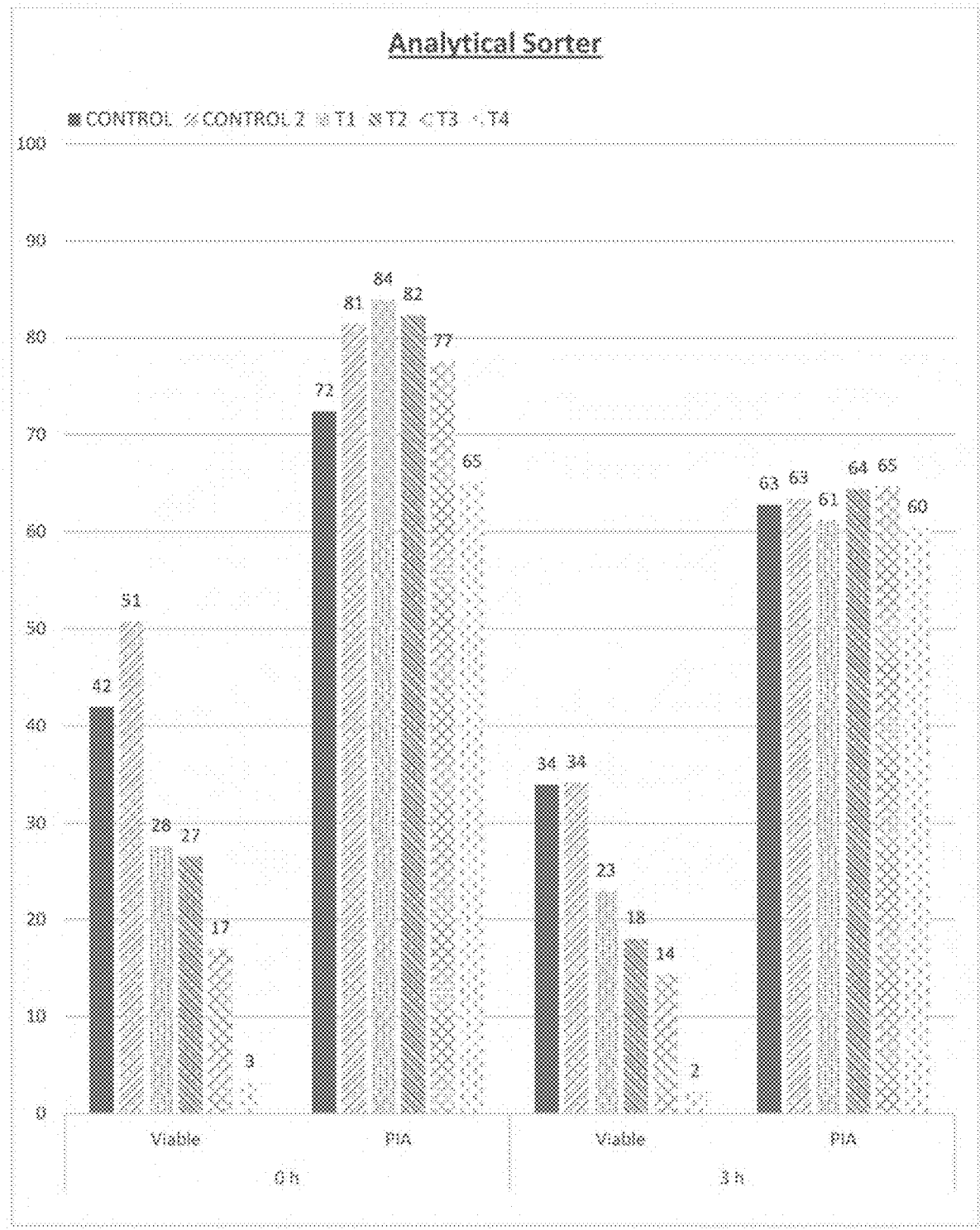
FIG. 22 shows post-thaw viability and PIAs of sperm sorted using different glycols in sheath fluid.

13. Diluted sperm was then held overnight in cold room.
14. Sperm cells were placed in straws and cryopreserved.
15. 0 and 3 hr post-thaw motility (IVOS II) are shown in FIG. 21. 0 and 3 hr post-thaw viability (PI) and PIA (PNA) are shown in FIG. 22.

Example 8

Table 8 summarizes the treatments for Example 8.

TABLE 8

| | STANDARD. | STAIN | Catch Volume | Sort Volume | Glycerol in sheath fluid | Cooling Time | Cryoprotectant for freezing |
|---|---|---|---|---|---|---|---|
| T1 | HOLDING MEDIA (1:3) | TALP 2% EY (120 mill/mL) | TRIS A (7.0 mL) | 40 mL | 3.0% Gly vol./vol. SF | 0 minutes | 3.0% Gly vol./vol. AB |
| T2 | | | | | | | 3.5% Gly vol./vol. AB |
| T3 | | | | | | | 4.0% Gly vol./vol. AB |
| T4 | | | | | | | 4.5% Gly vol./vol. AB |
| T5 | | | | | | | 5.0% Gly vol./vol. AB |
| T6 | | | | | | | 5.5% Gly vol./vol. AB |
| T7 | | | | | | | 6.0% Gly vol./vol. AB |

1. Fresh ejaculates were obtained from four bulls.
2. Ejaculates were QCed, standardized and stained in accordance with the procedures delineated in Example 1.
3. Sheath fluid control was connected and sheath fluid tank pressurized.
4. Stained sample placed on flow cytometer and drop delay verified.
5. 7 catch tubes up to 40 mL were bulk sorted using glycerol 3.0% sheath fluid (SF).

6. All tubes were centrifuged and decanted.

7. Sufficient AB was added to each tube in order to yield 4 million sperm per straw:
AB 3.0% glycerol vol./vol. (T1)
AB 3.5% glycerol vol./vol. (T2)
AB 4.0% glycerol vol./vol. (T3)
AB 4.5% glycerol vol./vol. (T4)
AB 5.0% glycerol vol./vol. (T5)
AB 5.5% glycerol vol./vol. (T6)
AB 6.0% glycerol vol./vol. (T7)

8. Diluted sperm was then held overnight in cold room.

9. Sperm cells were placed in straws and cryopreserved.

Figure 23:
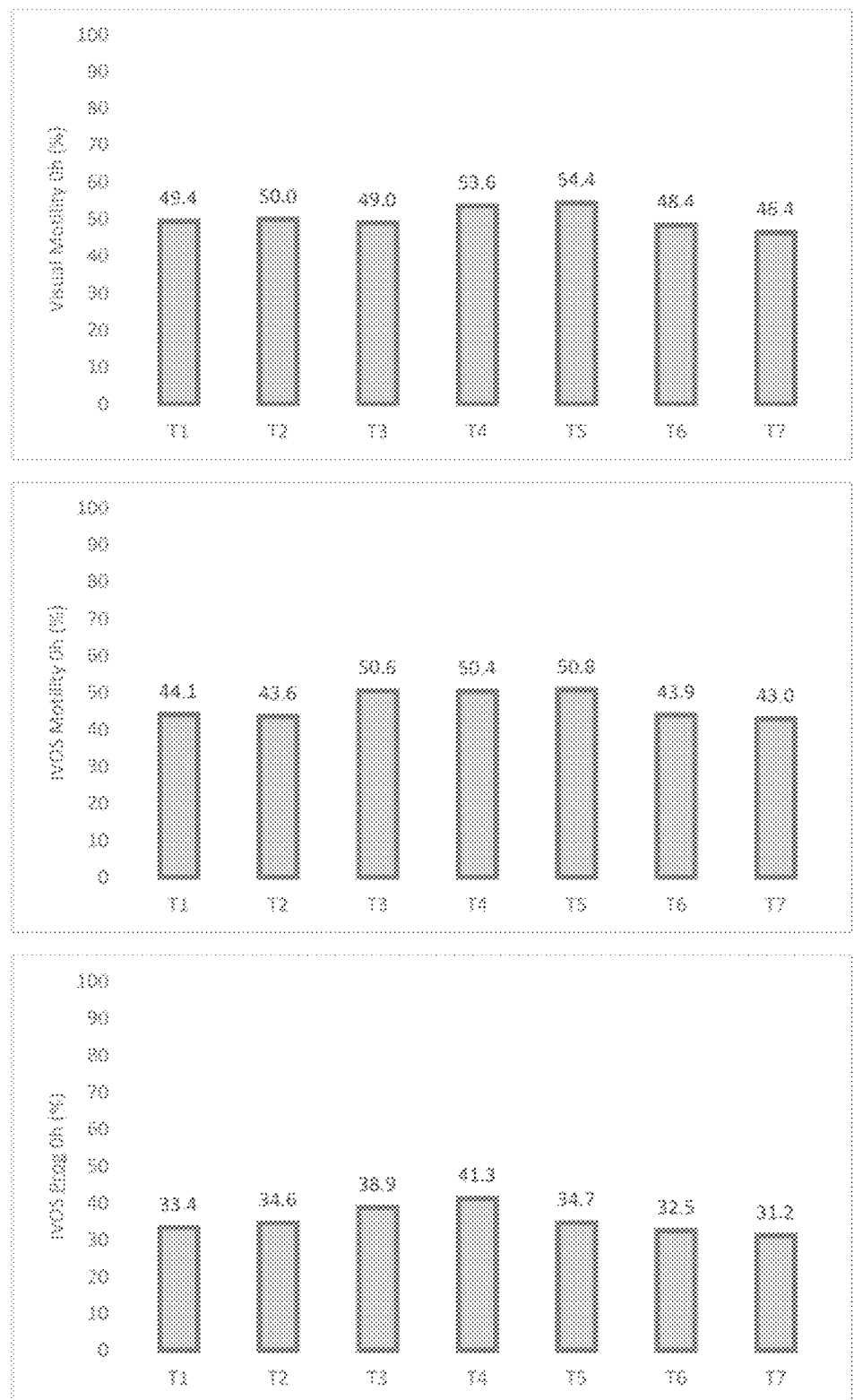
FIG. 23 shows 0 h post-thaw motility for sperm sorted using 3% glycerol in the sheath fluid and cryopreserved in media having varying concentrations of glycerol.
Figure 24:
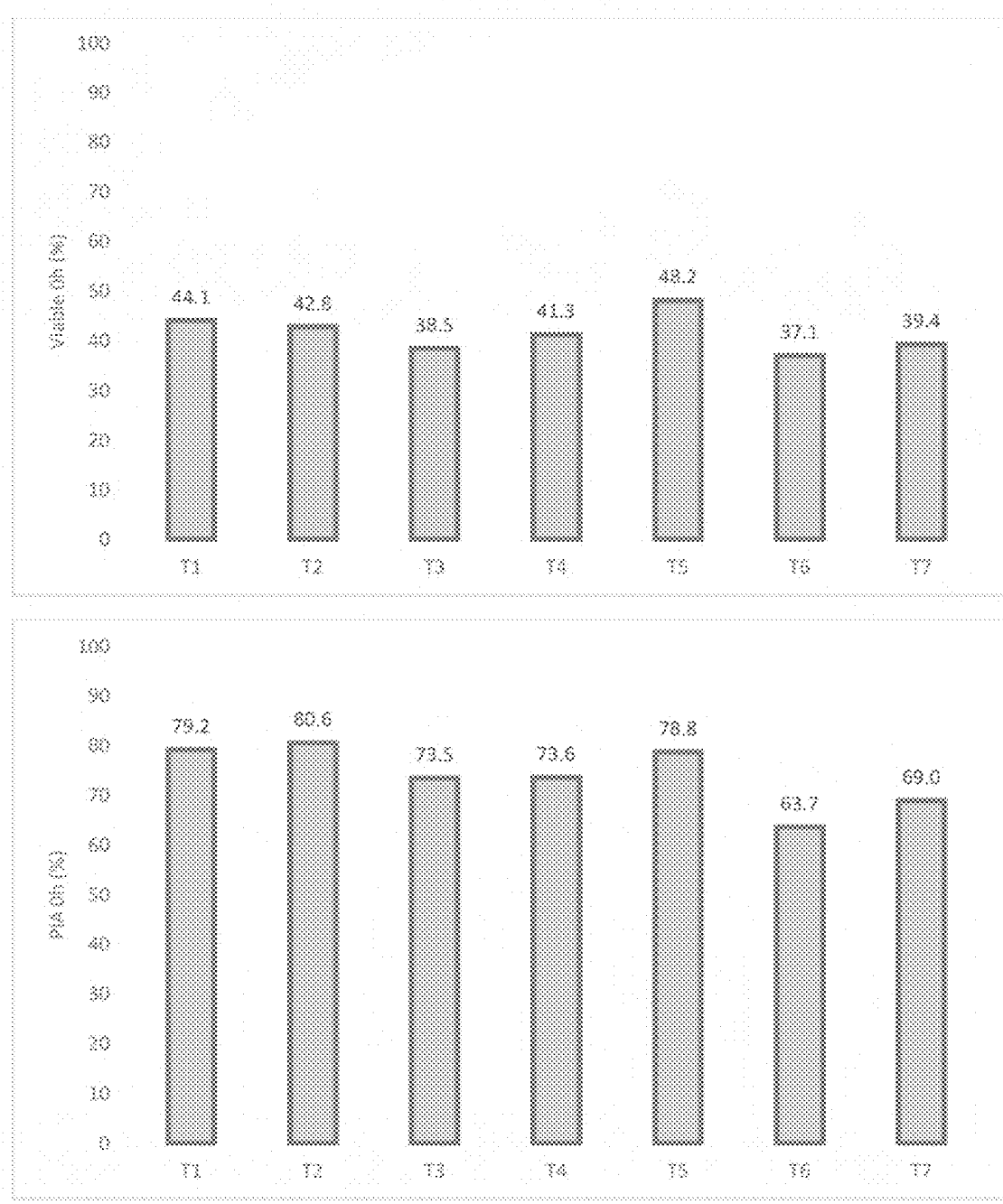
FIG. 24 shows 0 h post-thaw viability and PIAs for sperm sorted using 3% glycerol in the sheath fluid and cryopreserved in media having varying concentrations of glycerol.
Figure 25:
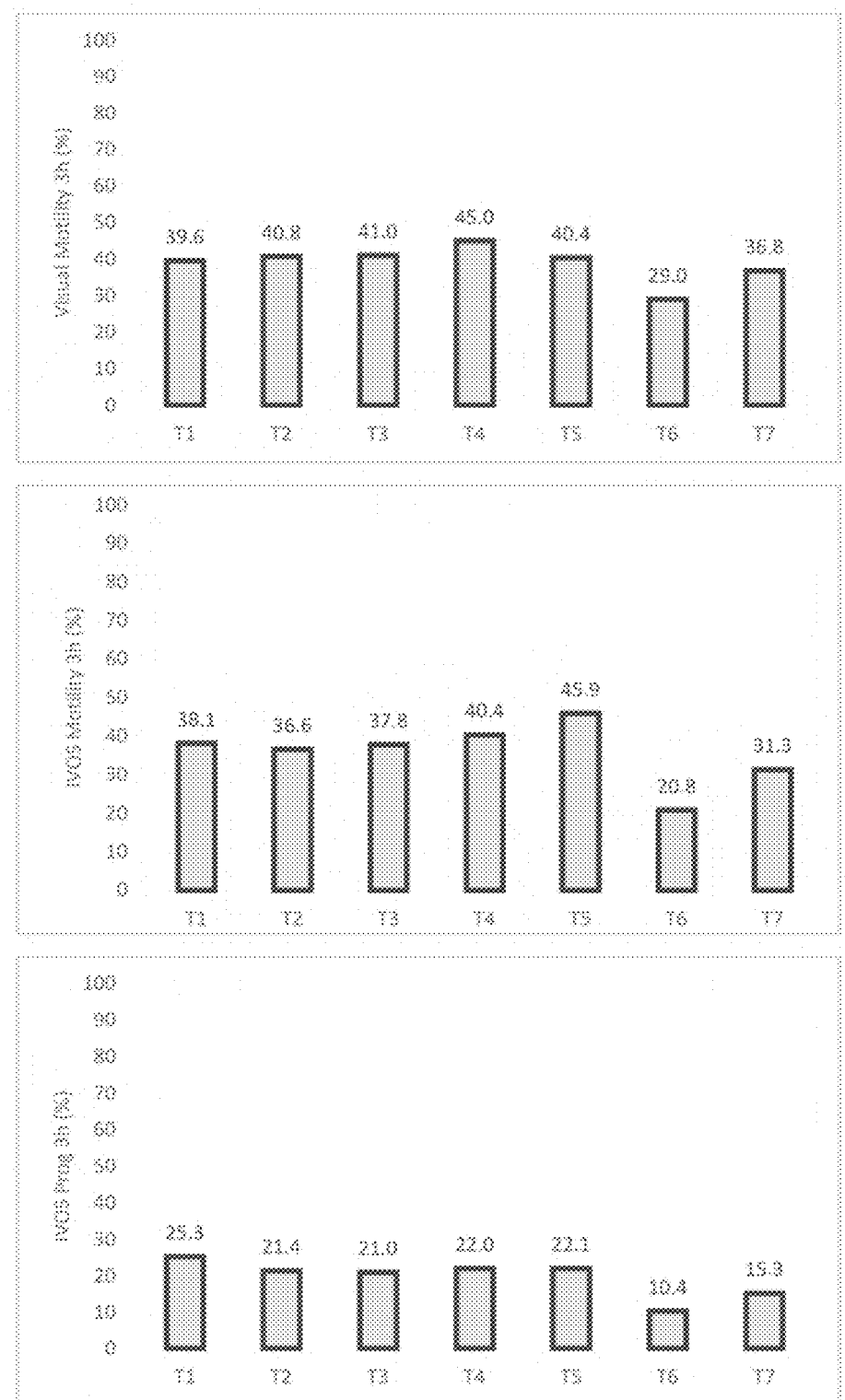
FIG. 25 shows 3 h post-thaw motility for sperm sorted using 3% glycerol in the sheath fluid and cryopreserved in media having varying concentrations of glycerol.

10. 0 hr and 3 hr motility (visual and IVOS) are shown in FIGS. 23 and 25. 0 hr and 3 hr viability (PI) and PIA (PNA) are shown in FIGS. 24 and 26. Convergence (3 hr/0 hr) for motility are shown in FIG. 27. Convergence for viability and PIA are shown in FIG. 28.

Example 9

Table 9 summarizes the treatments for Example 9.

TABLE 9

| | Catch Volume | Sort Volume | Sheath fluid | Cooling Time | Freezing media | Cryoprotectant for freezing | Hold time before freezing |
|---|---|---|---|---|---|---|---|
| Control 1 | TRIS A (3.5 mL) | 20 mL (15 Mill) | 0% Gly vol./vol. SF | 90 minutes | Yes (12% vol./vol. glycerol) | 6.0% Gly vol./vol. AB | 2 hours |
| Control 2 | | | | | | | Overnight |
| T1 | | | | | No | | 2 hours |
| T2 | TRIS A (7.0 mL) | 40 mL (30 Mill) | 3.0% Gly vol./vol. SF + AKG (0.0875 mg/mL) | 0 minutes | | 4.5% Gly vol./vol. AB | Overnight |

1. Fresh ejaculates were obtained from ten bulls.

2. Ejaculates were QCed, standardized and stained in accordance with the procedures delineated in Example 1.

3. Sheath fluid control was connected and sheath fluid tank pressurized.

4. 2 catch tubes up to 20 mL (or 15 million sperm) were bulk sorted using glycerol 0.0% vol/vol. sheath fluid (SF).

5. Tubes were placed in cold room for 90 minutes and 20 mL of freezing media (12% vol./vol. glycerol) was added (two step addition).

6. Treatment sheath fluid was connected and sheath fluid tank pressurized.

7. Stained sample placed on flow cytometer and drop delay verified.

8. 1 catch tube up to 40 mL (or 30 million sperm) was bulk sorted using glycerol 3.0% vol./vol. SF+alpha-keto glutarate (AKG).

9. All tubes were centrifuged and decanted.

10. AB was added to each tube:

1200 uL of AB 6.0% glycerol vol./vol. (Control 1 and Control 2)

1200 uL of AB 4.5% glycerol vol./vol. (T1 and T2)

11. Control 1 and T1 sperm held for 2 hours in AB and then cryopreserved in AI straws (2 straws per treatment at 4 mill. sperm/straw).

12. Control 2 and T2 held overnight in AB and then cryopreserved in AI straws (2 straws per treatment at 4 mill. sperm/straw).

Figure 30:
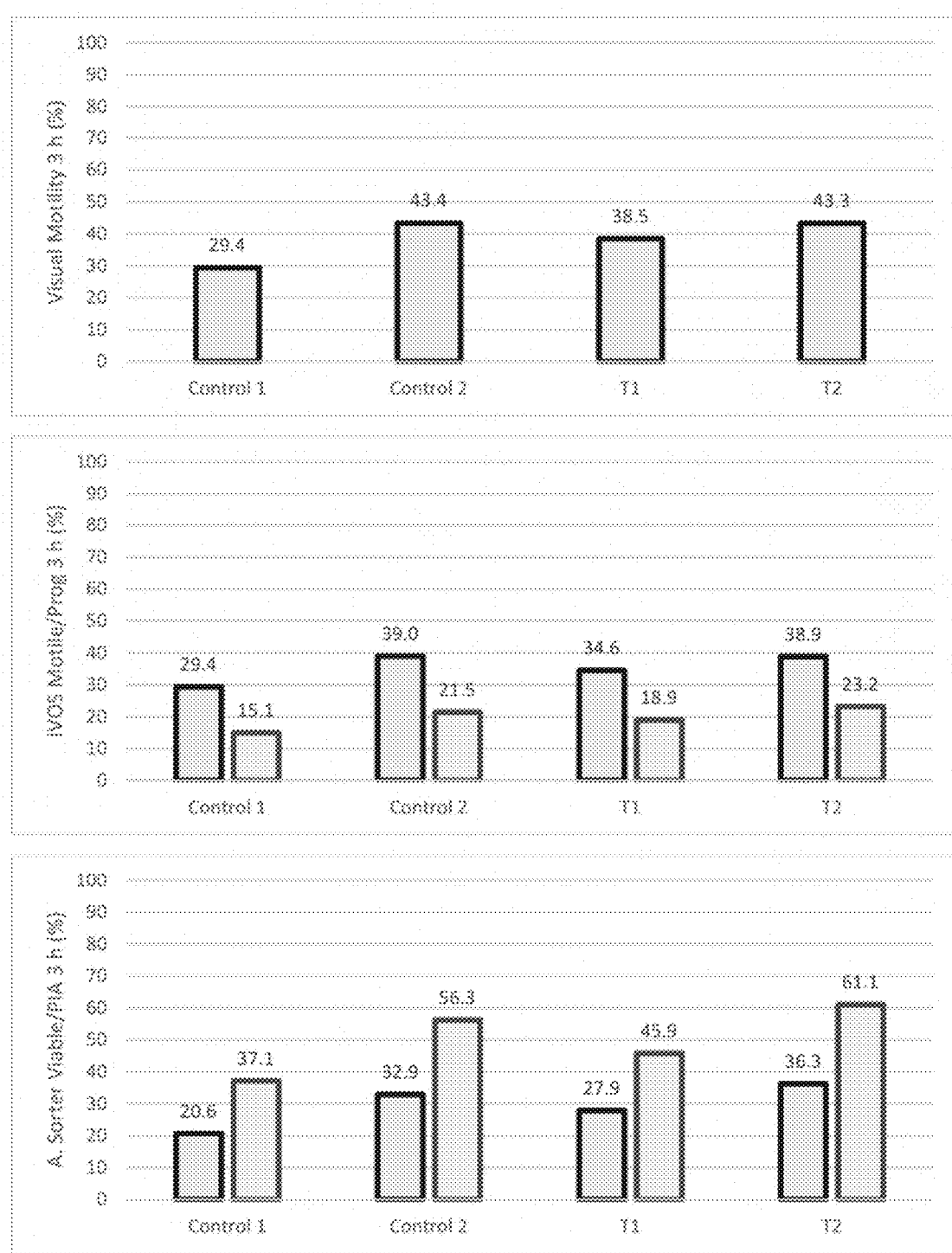
FIG. 30 shows 3 h post-thaw motility, viability and PIAs for sperm sorted using varying amounts of glycerol in the sheath fluid and cryopreserved in media having varying concentrations of glycerol.
Figure 31:
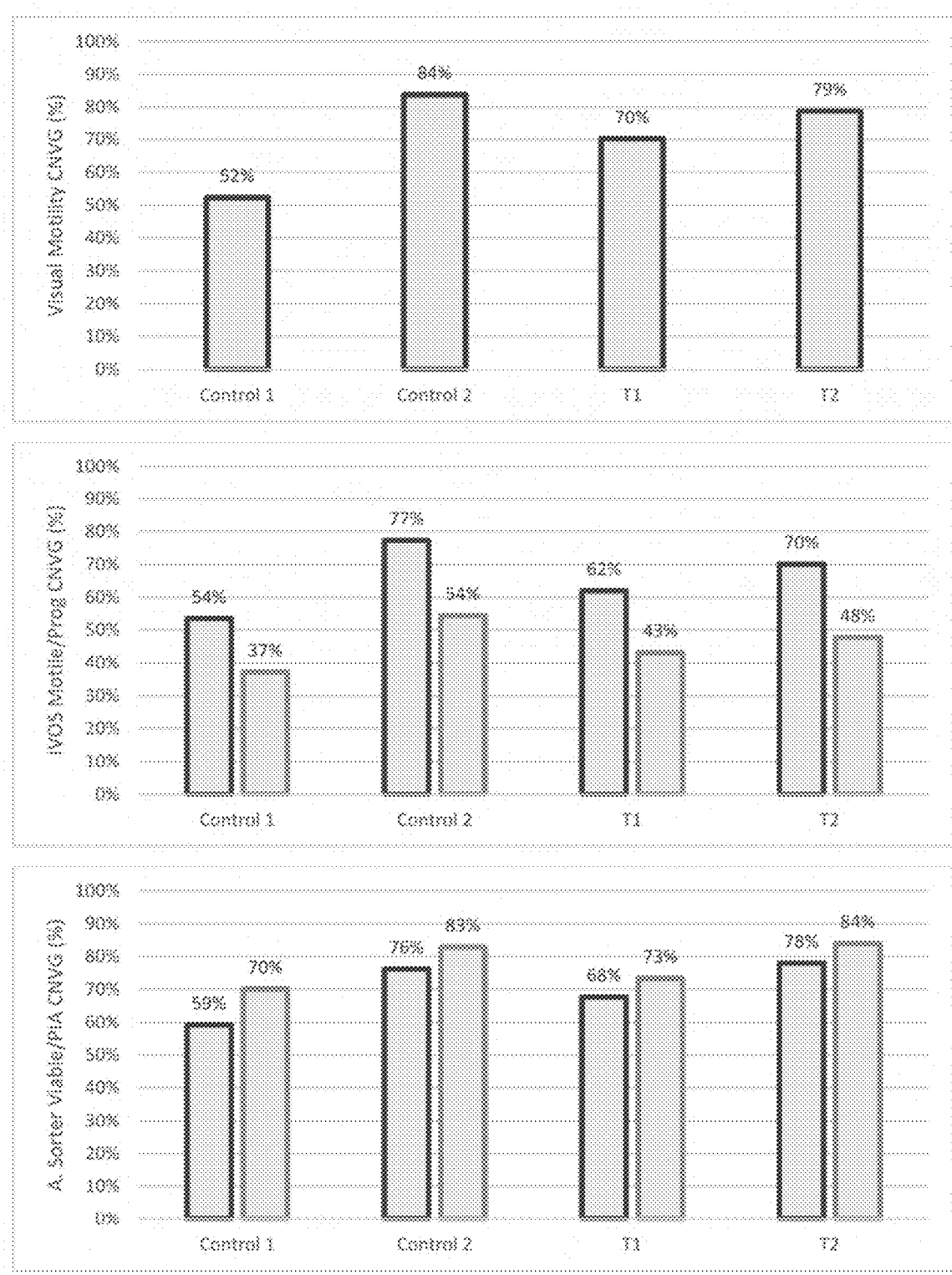
FIG. 31 shows convergence of post-thaw motility, viability and PIAs for sperm sorted using varying amounts of glycerol in the sheath fluid and cryopreserved in media having varying concentrations of glycerol.

13. 0 and 3 hr motility (visual and IVOS), viability (PI), PIA (PNA) and convergence (0 hr/3 hr) were assessed post-thaw. 0 hr motility (visual and IVOS), viability and PIAs are shown in FIG. 29. 3 hr motility (visual and IVOS), viability and PIAs are shown in FIG. 30. Convergence (3 hr/0 hr) for motility, viability and PIAs are shown in FIG. 31.

Example 10

Table 10 summarizes the treatments for Example 10.

TABLE 10

| | STANDARD. | STAIN | Catch Volume | Sort Volume | Gly. in SF | AKG | Cooling Time | Freezing Media | Cryoprotectant for freezing | Hold time before freezing |
|---|---|---|---|---|---|---|---|---|---|---|
| T1 - Control | HOLDING MEDIA (1:3) | TALP 2% EY (120 mill/mL) | TRIS A (3.5 mL) | 20 mL (15 Mill. sperm) | 0% vol./vol. | No | 90 minutes | Yes (12% vol./vol. glycerol) | 6.0% Gly vol./vol. AB | 2 hours |
| T2 - 3% gly. SF | | | TRIS A (7.0 mL) | 40 mL (30 Mill. sperm) | 3% vol./vol. | Yes (0.0875 mg/mL) | 0 minutes | No | 4.5% Gly vol./vol. AB | 2 hours |

1. Fresh ejaculates were obtained from three bulls.

2. Ejaculates were QCed, standardized and stained in accordance with the procedures delineated in Example 1.

3. Treatment 1 (control) sheath fluid (no glycerol) was connected and sheath fluid tank pressurized.

4. 4 control catch tubes up to 20 mL (or 15 million sperm) were bulk sorted.

5. Tubes were placed in cold room for 90 minutes and 20 mL of freezing media (12% glycerol vol./vol.) was added (two step addition).

6. Treatment 2 (3% glycerol vol./vol. with AKG) sheath fluid was connected and tank pressurized.

7. 2 catch tubes up to 40 mL (or 30 million sperm) were bulk sorted.

8. All tubes were then centrifuged and decanted. Pellets for T1 (4 tubes) were consolidated. Pellets for T2 (2 tubes) were consolidated.

9. AB was added to each tube:
AB 6.0% glycerol vol./vol. to Treatment 1
AB 4.5% glycerol vol./vol. to Treatment 2

10. Diluted sperm held for 2 hours in AB and then cryopreserved in AI straws (4 mill. sperm/straw).

11. 200 oocytes per treatment were then fertilized via IVF. Results of the IVF are shown in FIG. 32.

Example 11

Example 11 consists of a field trial to test the conception rate achieved with sexed semen sorted using sheath fluid comprising 3% glycerol vol./vol. and 0.0875 mg/mL of alpha-ketoglutarate. 5 Sires, and greater than 3000 heifers (up to 3' lactation) receiving 1 to 3 AI inseminations with 90% female sex-sorted semen, were utilized.

Figure 34:
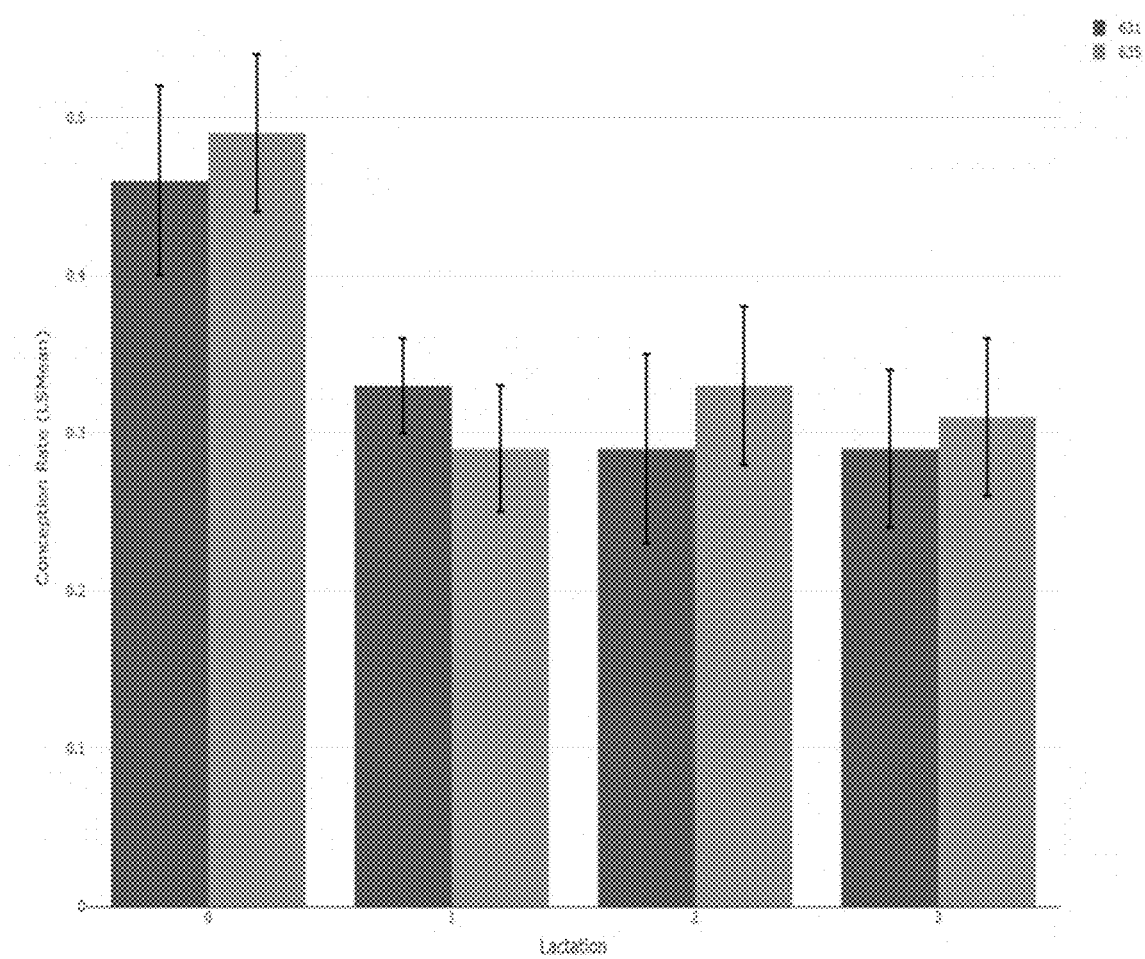
FIG. 34 shows conception rates for sperm sorted with either glycerol in the sheath fluid or absent from the sheath fluid.

Results from Example 11 are shown in FIGS. 33 and 34. FIG. 33 shows the post thaw motility, PIA, convergence and viability of sperm used in the field trial. FIG. 34 shows the conception rates achieved.

Example 12

Example 12 tested the efficacy of a diluted glycerol solution ("cryolizer") that, when mixed with a calculated amount of TRIS A (TRIS+20% egg yolk) becomes AB, eliminating the need for pure glycerol in sperm sorting laboratories.

Table 11 summarizes the treatments for Example 12.

TABLE 11

| Glycerol (v/v) | GRAMS TRIS A | GRAMS Glycerol STOCK | AB TOTAL | EY % | mOsm |
|---|---|---|---|---|---|
| 20% | 32.761 | 9.959 | 42.720 | 13.9 | 1077 mOsm |
| 45% | 40.183 | 4.937 | 45.120 | 17.5 | 1084 mOsm |
| 65% | 43.325 | 3.715 | 47.040 | 18.3 | 1085 mOsm |
| 100% | 47.628 | 2.772 | 50.400 | 19.1 | 1090 mOsm |

1. Five ejaculates were obtained from a bull.
2. Ejaculates were QCed, standardized and stained in accordance with the procedures delineated in Example 1.
3. 4 catch tubes were bulk sorted using sheath fluid containing glycerol 3.0% vol./vol. +alpha-keto glutarate (AKG).
4. Tubes were placed in a cold room for 15 minutes.
5. All tubes were centrifuged and decanted and pellets consolidated.
6. Pellets were separated into 5 tubes containing AB 4.5% Glycerol achieved as follows:
CONTROL—prepared with pure glycerol (100% v/v)
TREATMENT 1—prepared with 20% cryolizer
TREATMENT 2—prepared with 45% cryolizer
TREATMENT 3—prepared with 65% cryolizer
7. Sperm were held overnight and frozen.
8. Perform 0 and 3 h motility (visual and IVOS), viability (PI) and PIA (PNA).

Figure 35:
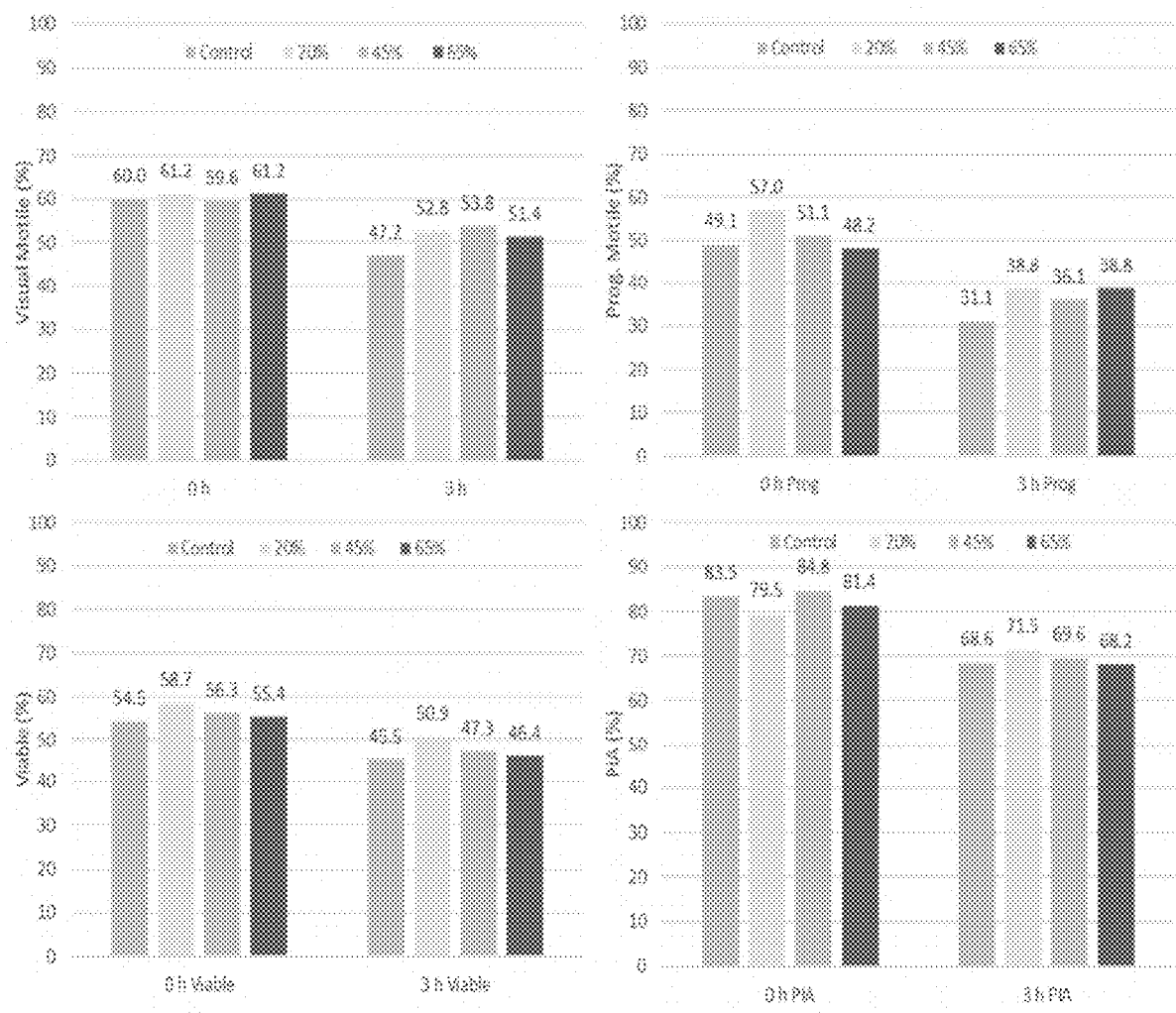
FIG. 35 shows the post thaw motility, viability and PIAs for sorted sperm frozen with AB prepared with cryolizer or with AB prepared with 100% glycerol vol./vol.

Results from Example 12 are shown in FIG. 35, which show a beneficial effect when AB is prepared with cryolizer (diluted glycerol) instead of 100% glycerol vol./vol..

Example 13

Table 12 summarizes the treatments for Example 13.

TABLE 12

| | Glycerol in Catch vol./vol. | Sort Volume | Glycerol in SF vol./vol. | Cool Time | Freezing media | Cryoprotectant |
|---|---|---|---|---|---|---|
| Control | 0% | 20 mL (15 Mill) | 0% | 90 minutes | Yes (12% vol./vol. glycerol) | 6.0% Gly AB |
| Glycerol in Catch | 2.4% | 40 mL (30 Mill) | 3% | 15 minutes | No | 4.5% Gly AB |

1. Ejaculates were obtained from 8 bulls.
2. Ejaculates were QCed, standardized and stained in accordance with the procedures delineated in Example 1.
3. CONTROL—Sheath Fluid (0.0% Glycerol) was used on Sorter A for bulls 1-4, and on sorter B for bulls 5-8.
1 catch tube per bull up to 20 mL (or 15 million) was bulk sorted into Tris A (0.0% Glycerol, No AKG).
Tubes were place in a cold room for 90 minutes. Freezing media (12% vol./vol. glycerol) was added after cool down.
4. TREATMENT—sheath fluid comprising 3.0% Glycerol and 0.0875 mg/mL AKG was used on Sorter B for bulls 1-4, and on sorter A for bulls 5-8.
1 catch tube per bull up to 40 mL (or 30 million) was bulk sorted into catch fluid comprising 2.4% Glycerol vol./vol..
Tube was place in a cold room for 15 minutes.
5. All tubes were centrifuged and decanted.
6. The following were added to the control tubes and treatment tubes respectively:
AB 6.0% Glycerol to CONTROL tubes
AB 4.5% Glycerol to TREATMENT tubes
7. Sperm were held for 12 hours (over-night) in AB and then frozen.
8. 0 and 3 h visual and IVOS motility, viability (PI) and PIA (PNA) were performed. Convergence was calculated for each parameter.

Figure 36:
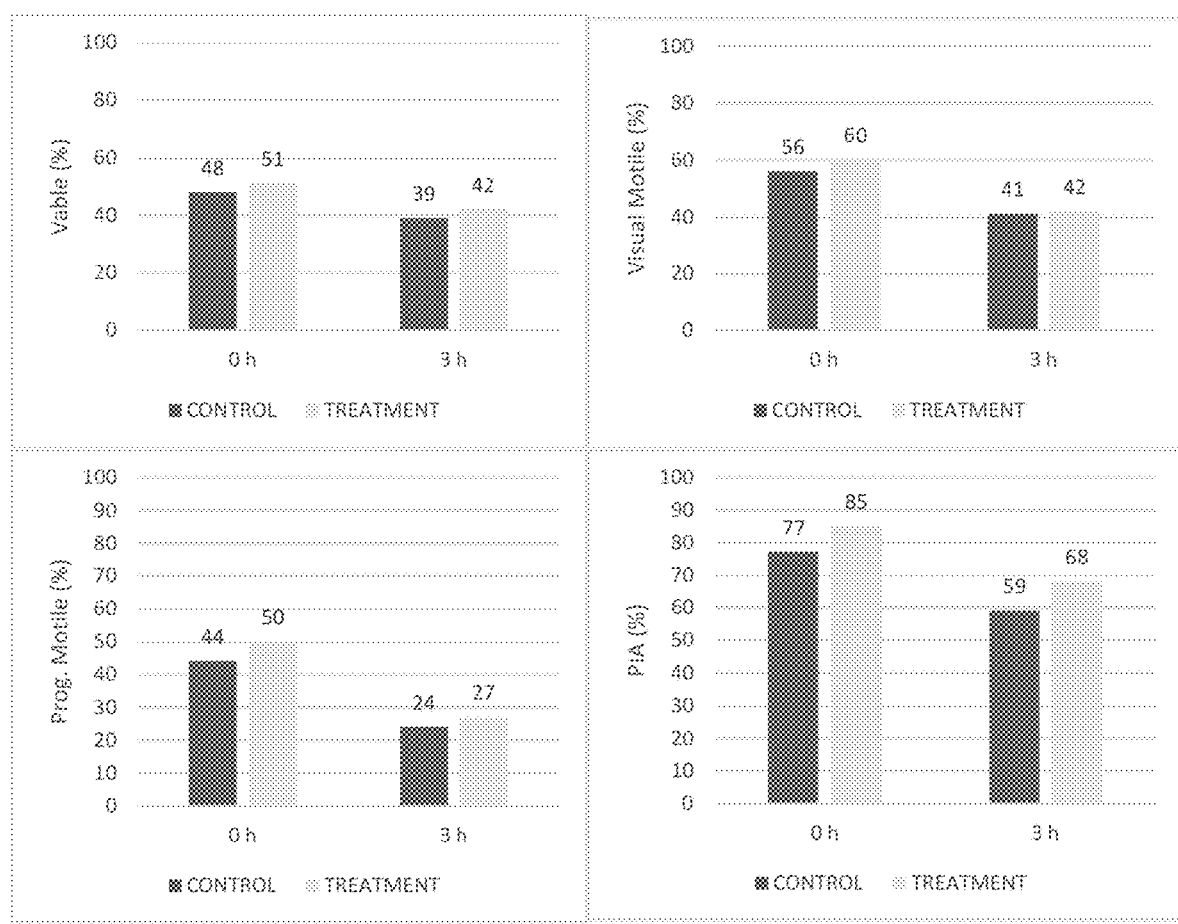
FIG. 36 shows the post thaw motility, viability and PIAs for sperm sorted with glycerol in the catch fluid and sheath fluid or absent from the catch fluid and sheath fluid.

Results from Example 13 are shown in FIG. 36.

Example 14

Example 14 demonstrates that as much as 400 millimolar Erythritol can be used in a fresh bovine extender with good support of bovine sperm motility over a 4 day period. This is with "conventional" (unsorted) sperm stained with Hoechst 33342 (to facilitate CASA using fluorescence).

The fresh extender is a media similar to Caprogen, which contains 5% (v/v) egg yolk and is bubbled with nitrogen gas prior to diluting sperm.

Caprogen with glycerol is one of the media compared in this Example and is comprised of the following components: Sodium Citrate Tribasic Dihydrate, 20.0 grams, Citric Acid Monohydrate, 0.25 grams, Glycine, 10.0 grams, D-(+)-Glucose, 3.0 grams, Potassium Phosphate Dibasic Anhydrous, 0.609 grams, n-Hexanoic Acid (caproic acid), 0.231 mL, Cyanocobalamin, 0.250 grams, Alphaketoglutarate Disodium Dihydrate, 0.35 grams, Trehalose Dihydrate, 0.750 grams, Glycerol, 10.0 mL, Streptomycin Sulphate, 0.150 grams, Gentamycin, 0.500 grams, Tylosin, 0.100 grams, Lincomycin, 0.300 grams, Spectinomycin, 0.500 grams, Chicken Egg Yolk, 5.0 mL.

Caprogen with erythritol is the other media compared in this Example and is comprised of the following components: Sodium Citrate Tribasic Dihydrate, 20.0 grams, Citric Acid Monohydrate, 0.225 grams, Glycine, 8.653 grams, D-(+)-Glucose, 2.50 grams, Potassium Phosphate Dibasic Anhydrous, 0.609 grams, n-Hexanoic Acid Sodium Salt, (caproic acid), 0.276 grams, Cyanocobalamin, 0.250 grams, Alphaketoglutarate Disodium Dihydrate, Trehalose Dihydrate, 0.750 grams, 0.35 grams, Erythritol, 14.64 grams, Streptomycin Sulphate, 0.150 grams, Gentamycin, 0.500 grams, Tylosin, 0.100 grams, Lincomycin, 0.300 grams, Spectinomycin, 0.500 grams, Chicken Egg Yolk, 5.0 mL.

In Caprogen with glycerol, the concentration of glycine is 135 millimolar and the concentration of glycerol is 135 millimolar. Control Media 1 was made with these same concentrations, while the balance of test media (Media 2-7) were made with the following concentrations as shown in Table 13:

TABLE 13

| | Concentration of Media Components Added | | |
|---|---|---|---|
| Media | Glycerol mMolar | Glycine mMolar | Erythritol mMolar |
| 1 | 135 | 135 | 0 |
| 2 | 0 | 135 | 0 |
| 3 | 0 | 135 | 35 |
| 4 | 0 | 135 | 65 |
| 5 | 0 | 135 | 135 |
| 6 | 0 | 135 | 270 |
| 7 | 0 | 135 | 400 |

Figure 37:
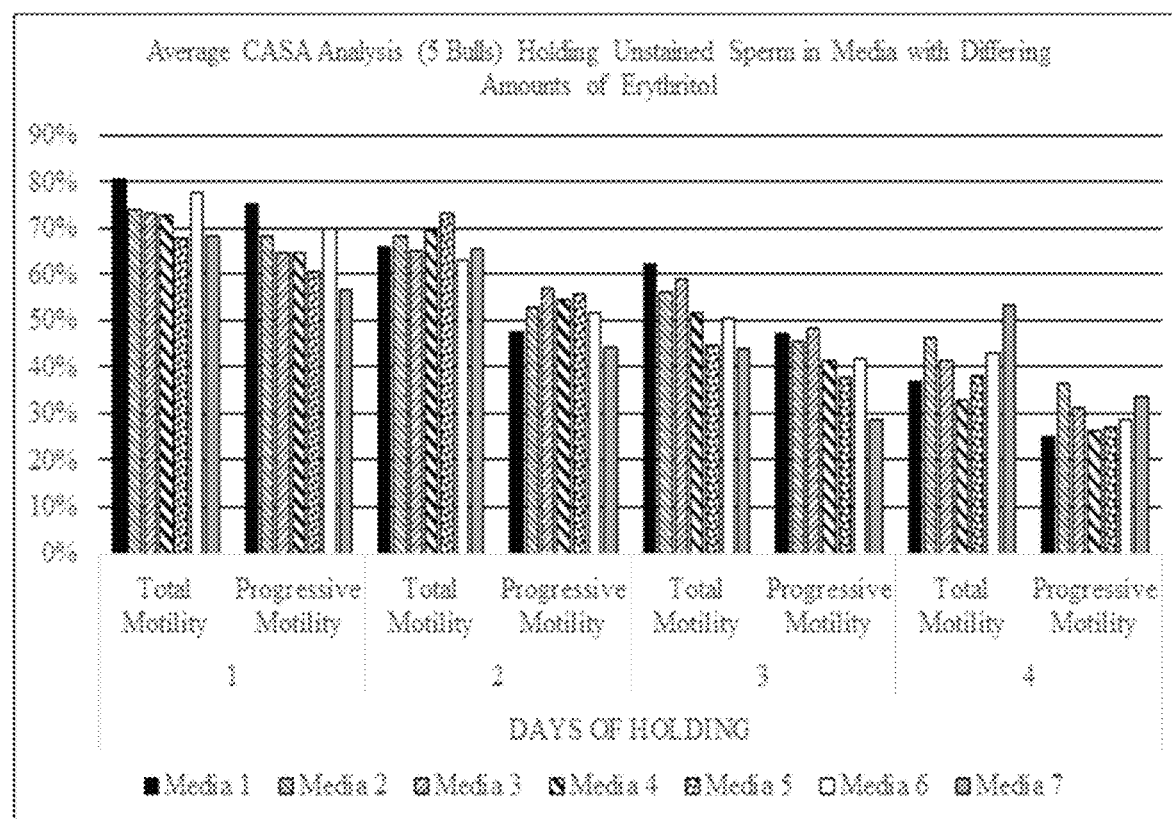
FIG. 37 shows motility of sperm held in Caprogen with glycerol and Caprogen with various concentrations of erythritol.

Fresh Bovine Ejaculates of 5 bulls were diluted to 160 million sperm per mL into Staining TALP, combined with Hoechst 33342 DNA stain, incubated 60 minutes at 34° C. (as standard staining for XY sperm sorting). Once stained, the sperm in TALP were diluted in the related media to a new concentration of 15 million sperm per mL and placed into 0.25 cc straws, sealed and held horizontal at 18° C. for 4 days. On each day, one straw of sperm was warmed for 15 minutes at 34° C. and the contents of about 200 microliters from the straw were combined with 100 microliters of fresh media identical to the specified test media used to hold the sperm. Sperm were analyzed on fluorescent CASA (Hamilton Thorne IVOS II) using UV illumination. The average Total and Progressive Motility for the 5 bulls is summarized in Table 14 and in FIG. 37.

TABLE 14

| | DAYS OF HOLDING | | | | | | | |
|---|---|---|---|---|---|---|---|---|
| | 1 | | 2 | | 3 | | 4 | |
| MEDIA NUMBER | Total Motility | Progressive Motility | Total Motility | Progressive Motility | Total Motility | Progressive Motility | Total Motility | Progressive Motility |
| 1 | 80% | 75% | 66% | 47% | 62% | 47% | 37% | 25% |
| 2 | 74% | 68% | 68% | 53% | 56% | 45% | 46% | 37% |
| 3 | 73% | 65% | 65% | 57% | 59% | 48% | 42% | 31% |
| 4 | 73% | 65% | 69% | 55% | 52% | 41% | 33% | 26% |
| 5 | 68% | 61% | 73% | 56% | 45% | 38% | 38% | 27% |
| 6 | 78% | 70% | 63% | 52% | 50% | 42% | 43% | 29% |
| 7 | 69% | 57% | 65% | 44% | 44% | 29% | 53% | 34% |

This test shows that 135 millimolar glycerol is beneficial for supporting sperm motility for up to 4 days and that replacement of glycerol with erythritol in a Caprogen fresh media provides similar support of sperm motility, with a benefit of erythritol showing up in the longer 4 day period.

Example 15

Example 15 demonstrates that the glycerol in the standard Caprogen recipe for extension of sorted bovine sperm stored for up to nine days at 17° C. may be replaced completely with erythritol to create longer time sperm storage when visual and CASA motilities are compared. Standard Caprogen (with glycerol) is referred to as "CaproGLY" and erythritol containing Caprogen is referred to as "CaproERY."

Preparation of media in volume of 100 mL: 95 mL of the respective media working solution is combined with 5 mL of egg yolk, stirred for 15 minutes, held overnight at 4° C., centrifuged for 60 minutes at 1200 G in 50 mL Falcon Tubes (clarified). On day of use, nitrogen gas is bubbled through the clarified media for 15 minutes. Table 15 shows the properties of the 2 media.

TABLE 15

| | pH | mOsm | mM Glycine | mM Glycerol | mM Erythritol |
|---|---|---|---|---|---|
| CaproGLY | 7.01 | 512 | 133 | 133 | |
| CaproERY | 7.03 | 482 | 120 | | 120 |

Sorting of the sperm to be held in the two fresh extenders: Fresh Ejaculates of 3 Jersey bulls are bulk sorted according to standard proprietary sex sorting methods disclosed in other patents. In brief, sperm are washed, concentrated and resuspended in a Hepes buffered TRIS Citrate extender to normalize concentration to about 1200 sperm per mL and pH about 7.15. Each 1 mL of staining comprises: 0.150 mL of sperm solution (about 160 million sperm), 64 nanomoles of Hoechst 33342 in 8 microliters, 592 mL of staining TALP and 100 nanomoles of FD&C food dye. The sample is incubated in a 4 mL sample tube at 34° C. for 60 minutes after which 0.25 mL of 8% (v/v) Egg Yolk TALP, which dilutes the sperm to about 120 million per mL and provides a final egg yolk concentration of 2% for the sample to be sorted.

Freshly stained sperm are bulk sorted at event rates of about 40,000 per second, where bulk sorting means collecting live-oriented sperm bearing both X and Y chromosomes, explicitly, the sorted sperm are equivalent quality to standard sorted sperm but not enriched for sex. 80 million sperm from each of the 3 Jersey bulls are sorted into a TRIS A catch fluid, cooled for a minimum of 90 minutes in a cold cabinet (typical temperature 4-7° C.), mixed in equal volumes with a non-egg-yolk TRIS B solution, concentrated by centrifugation and recovery of sperm pellets and determination of final concentration (concentrated sperm) in the range of 100-115 million sperm per mL. 3 volumes of CaproGLY or CaproERY is then combined with 1 volume of the concentrated sperm to a final formulated concentration of about 20-24 million per mL (about 5.0-5.5 million sperm per 0.25 cc straw).

The formulated sperm are filled into 0.25 cc straws, sealed and stored horizontally at 17° C. for up to nine days. On the specified test days, a straw is opened and checked for visual motility (counted by eye by technician using microscope analysis on heated stage), CASA total motility and CASA progressive motility using a Hamilton Thorne IVOS system. In addition to the straws, a 0.50 mL sample of each of the six samples is stored in a 4 mL sample tube at 17° C. for comparison on the eighth day.

Table 16 summarizes the average motilities of the three Jersey bulls at different days.

Example 16

Example 16 demonstrates that sex-sorted sperm stored in a Caprogen media using erythritol instead of glycerol is able to create a number of pregnancies similar the standard Caprogen.

In order to pre-evaluate the possible fertility outcomes using CaproERY as a substitute in this setting where CaproGLY has worked well, a small number (about 145) heifers were bred in four time segments and compared to data from the same bulls at the same farms using sex sorted sperm stored in CaproGLY. Typically, with fresh extended semen, the heifers are bred within 1-2 days of the sorting and formulation day.

|  | Total Heifers Bred | Total Pregnant | Percent Pregnant |
|---|---|---|---|
| CaproGLY | 277 | 159 | 57.4% |
| CaproERY | 145 | 77 | 53.1% |

This research field test did not use a split processing, does not have an evenly distributed number of straws in each treatment and is not equally distributed between bulls and farms. Accordingly, the relative nominal values (57.4% vs 53.1%) are not statistically different. Both values are well within the standard range seen for CaproGLY over the 40 month time period and accordingly, CaproERY gives similar fertility.

Example 17

Example 17 demonstrates that erythritol may be used (with or without glycine) in sheath fluid for sperm sorting or freezing extenders at concentrations between 15-110 mMolar and be equal or better to standard control media without erythritol.

TABLE 16

| TREATMENT | DAY | Hold in | VISUAL MOTILITY | CASA TOTAL MOTILITY | CASA PROG MOTILITY | CASA PROG/TOT |
|---|---|---|---|---|---|---|
| CaproERY | 1 | Straw | 68% | 76% | 55% | 72% |
| CaproGLY | 1 | Straw | 68% | 73% | 53% | 73% |
| CaproERY | 2 | Straw | 61% | 66% | 51% | 77% |
| CaproGLY | 2 | Straw | 58% | 61% | 44% | 72% |
| CaproERY | 3 | Straw | 71% | 73% | 48% | 65% |
| CaproGLY | 3 | Straw | 68% | 64% | 45% | 69% |
| CaproERY | 4 | Straw | 67% | 68% | 48% | 71% |
| CaproGLY | 4 | Straw | 51% | 51% | 35% | 68% |
| CaproERY | 7 | Straw | 63% | 59% | 45% | 76% |
| CaproGLY | 7 | Straw | 33% | 39% | 29% | 74% |
| CaproERY | 8 | Straw | 55% | 52% | 35% | 68% |
| CaproGLY | 8 | Straw | 23% | 16% | 4% | 28% |
| CaproERY | 8 | Tube | 65% | 61% | 55% | 89% |
| CaproGLY | 8 | Tube | 31% | 30% | 11% | 38% |
| CaproERY | 9 | Straw | 47% | 42% | 34% | 81% |
| CaproGLY | 9 | Straw | 20% | 9% | 2% | 23% |

The above results show that when the principle of having equal molarity of glycine and the accompanying polyol (glycerol or erythritol) is followed, fully substituting glycerol with erythritol creates a comparable Caprogen fresh semen extender that is as good or better than that made with glycerol. For holding times longer than 4 days the erythritol is better at preserving quality as seen in motility. It also appears that storage in tubes may be better than straws.

Standard bovine sperm sorting uses sheath fluid comprising 68 mM Fructose, 80 mM Citrate and 243 mM TRIS at pH 6.80 and osmolarity 290-300 mOsm. (CONTROL Sheath Fluid). Combining 80 volumes of such control sheath fluid with 20 volumes of fresh egg yolk followed by clarification results in a CONTROL cooling solution called TRIS A (The "A Fraction"). Combining 88 volumes of TRIS A with 12 volumes of pure glycerol creates a solution called TRIS B (The "B Fraction"). In the case of standard sperm sorting, the "B Fraction" may optionally contain no egg yolk and may be called "Eggless B Fraction" still containing 12 volumes of pure glycerol.

Table 18 shows the millimolar concentrations of the components used in this test, where the control media does not contain any glycine or erythritol and test samples contain various amounts of erythritol and in some cases glycine. The pH of all media was 6.70-6.75 and the osmolarity was 290-305 mOsm.

TABLE 18

| | Visual Motility | | Concentrations in mM at freeze. | | | | |
|---|---|---|---|---|---|---|---|
| | 0 h | 3 h | Erythritol | Glycine | Fructose | Citrate | TRIS |
| CONTROL | 36% | 27% | 0 | 0 | 54 | 64 | 194 |
| A | 42% | 34% | 51 | 50 | 30 | 35 | 106 |
| B | 40% | 24% | 108 | 0 | 30 | 36 | 109 |
| C | 42% | 31% | 53 | 46 | 30 | 35 | 105 |
| D | 42% | 36% | 35 | 34 | 30 | 43 | 130 |
| E | 54% | 35% | 25 | 0 | 51 | 45 | 138 |
| F | 37% | 31% | 14 | 14 | 30 | 63 | 190 |
| G | 41% | 40% | 25 | 0 | 30 | 61 | 186 |
| | Visual Motility | | Concentration (mM) in sheath fluid | | | | |
| | 0 h | 3 h | Erythritol | Glycine | Fructose | Citrate | TRIS |
| CONTROL | 35% | 23% | 0 | 0 | 68 | 80 | 243 |
| H | 35% | 28% | 62 | 0 | 61 | 33 | 102 |
| I | 47% | 28% | 35 | 35 | 8 | 75 | 235 |
| J | 47% | 37% | 65 | 0 | 8 | 72 | 223 |

The same two bulls were used for each of two tests and were measured for post-thaw quality at the same time. The first test was done with unstained non-sorted sperm similar to standard "conventional freezing." The second test was done using different sheath fluids for sorting sperm.

The first test compared control (standard media) to 7 alternate media (A-G) with compositions including various amounts of erythritol and in some cases glycine. 10 milliliters of sperm of each bull at a concentration of 100 million sperm per milliliter was cooled in standard TRIS A (control media) over 90 minutes from room temperature to about 4-6° C. Samples were then divided into 1 milliliter aliquots and 0.5 mL of cold TEST-B media was added, held for 15 minutes before an additional 0.5 mL of TEST-B media was added. This resulted in final sperm concentrations of 50 million per mL. These samples were loaded into 0.25 cc cryopreservation straws and frozen in a controlled vapor freeze method normally used to freeze conventional semen.

The glycerol concentrations in TEST-B media was always 6.0% (vol/vol) resulting in final glycerol concentrations of 3.0% (vol/vol). All of the TEST-B media had 0% egg yolk which resulted in final egg yolk concentrations of 10% (vol/vol). The concentrations of chemical components, at time of freezing are shown in the table (CONTROL vs A-G). These conditions cooled the sperm in the standard amount of egg yolk (20%), cryopreserving them in ½ of the standard amount of egg yolk and glycerol. The visual motility results show that under such control conditions that all 7 erythritol containing media supported cryopreservation as well as or better than the control without any erythritol. The results show that up to about 110 mM of erythritol may be used in freezing bovine sperm, with optimal freezing results being achieved with 15-50 mM erythritol.

The second test compared a CONTROL (standard) sheath fluid to three alternate sheath fluids (H-J). The compositions of all sheath fluids are shown in the table. After sorting all samples were handled in the identical manner to standard sperm sorting. A 3.5 mL volume of catch fluid (TRIS A) is placed in each catch tube and sorted sperm are sorted into the catch tube to a volume of 20 mL. That volume of fluid is then cooled for 90 minutes to about 4-6° C. then an equal volume of cold Eggless B Fraction is added. Sperm cells are concentrated by centrifugation and disposal of supernatant and resuspended in an egg yolk TRIS AB Fraction prepared by mixing equal volumes of A Fraction and B Fraction. Cells were formulated to about 18 million per mL and frozen in 0.25 cc straws in a controlled vapor freeze method normally used to freeze conventional semen (same as above).

The results show that up to 60 mM erythritol may be present in sheath fluid and be beneficial to sperm quality in the standard method for post-sort handling of sperm.

As can be easily understood from the foregoing, the basic concepts of the present invention may be embodied in a variety of ways. The invention involves numerous and varied embodiments of processing sperm including, but not limited to, the best mode of the invention.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of "sorter" should be understood to encompass disclosure of the act of "sorting"—whether explicitly discussed or not—and, conversely, were there effectively disclosure of the act of "sorting", such a disclosure should be understood to encompass disclosure of a "sorter" and even a "means for sorting." Such alternative terms for each element or step are to be understood to be explicitly included in the description.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

Moreover, for the purposes of the present invention, the term "a" or "an" entity refers to one or more of that entity. As such, the terms "a" or "an", "one or more" and "at least one" can be used interchangeably herein.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

We claim:

1. A method of increasing resolution while analyzing sperm comprising:
   staining a sperm sample having viable X-chromosome bearing sperm and viable Y-chromosome bearing sperm with a staining media;
   contacting the stained sperm sample with a sheath fluid in a flow path; and
   manipulating a ratio of viable X-chromosome bearing sperm to viable Y-chromosome bearing sperm to form at least one manipulated sperm population;
   the sheath fluid comprising cryoprotectant comprising a polyalcohol, the polyalcohol at a vol./vol. or wt./vol. concentration between about 0.1% and about 6% in the sheath fluid thereby increasing resolution.

2. The method of claim 1 further comprising the step of collecting the manipulated sperm population in a collection media.

3. The method of claim 2, wherein the collection media comprises an amount of cryoprotectant.

4. The method of claim 2, wherein each of the staining media, the sheath fluid and the collection media include an amount of cryoprotectant.

5. The method of claim 1, wherein the step of manipulating a ratio of viable X-chromosome bearing sperm to viable Y-chromosome bearing sperm to form at least one manipulated sperm population further comprises either selecting sperm for separation and collection or for photo-damage and collection.

6. The method of claim 1 further comprising the step of freezing the manipulated sperm sample.

7. The method of claim 1, further comprising one or more of the following processing steps: holding; transporting; buffering; chilling; warming; diluting; concentrating; exciting with a laser; charging; deflecting; ablating; collecting; shaking; oscillating; magnetically separating; oxygenating; labeling; precipitating; centrifuging; resuspending; mixing; dialyzing; cryostabilizing; microchip processing; and flow cytometry processing.

8. The method of claim 1, wherein the polyalcohol is selected from the group consisting of: ethylene glycol; glycerol; erythritol; threitol; arabitol; ribitol; xylitol; sorbitol; galactitol; iditol; volemitol; fucitol; inositol; a glycylglycitol, and combinations thereof.

9. The method of claim 1, wherein the polyalcohol is selected from the group consisting of: propylene glycol, butane triol and combinations thereof.

10. The method of claim 1, wherein at least one of the sheath fluid and the staining media further comprises an antioxidant.

11. The method of claim 10, wherein the antioxidant comprises an antioxidant selected from the group consisting of: pyruvate, vitamin B12; vitamin B12 vitamers; vitamin E; vitamin E vitamers; tocopherol; tocotrienol; α-tocophery; alpha ketoglutarate; derivatives thereof and combinations thereof.

12. The method of claim 1, wherein the sheath fluid comprises the cryoprotectant at a vol./vol. or wt./vol. concentration between about 0.1% and about 2%; between about 2% and about 4%; between about 4% and about 6%; between about 1% and about 2%; between about 2% and about 3%; between about 3% and about 4%; between about 4% and about 5%; between about 5% and about 6%; between about 2% and about 6%; or between about 3% and about 5%.

13. The method of claim 1, wherein the sheath fluid comprises a saline buffered with phosphates, TRIS citrate, or HEPES.

14. The method of claim 1, wherein cryoprotectant is added to the staining media in a first amount and added to the sheath fluid in a second amount, and wherein the second amount is greater than the first amount.

15. The method of claim 1, wherein increasing resolution comprises increasing a peak to valley ratio formed by the viable X-chromosome bearing sperm and the viable Y-chromosome bearing sperm.

16. The method of claim 1, wherein the step of manipulating comprises sorting the sperm sample at an event rate of at least 20,000 events per second.

17. A method of processing sperm comprising:
   staining a sperm sample with a staining media having a DNA selective dye;
   injecting the stained sperm sample into a flow of sheath fluid;
   exposing the stained sperm sample in the flow of sheath fluid to an electromagnetic radiation source which causes a detectable response in the DNA selective dye;
   detecting the response of the DNA selective dye to the electromagnetic radiation exposure;

manipulating a ratio of viable X-chromosome bearing sperm to viable Y-chromosome bearing sperm to form at least one manipulated sperm population; and collecting the at least one manipulated sperm population in one or more collection vessels having collection medias therein;

the staining media, the sheath fluid and the collection medias comprising a cryoprotectant, the cryoprotectant comprising a polyalcohol.

18. The method of claim 17, wherein the staining media comprises a first amount of the cryoprotectant, the sheath fluid comprises a second amount of the cryoprotectant, and the collection media comprises a third amount of the cryoprotectant.

19. The method of claim 18, wherein the first amount of the cryoprotectant is less than the second amount of the cryoprotectant and the third amount of the cryoprotectant.

20. The method of claim 18, wherein the third amount of the cryoprotectant is greater than the first amount of the cryoprotectant and the second amount of the cryoprotectant.

21. The method of claim 17, wherein the polyalcohol is selected from the group consisting of: ethylene glycol; glycerol; erythritol; threitol; arabitol; ribitol; xylitol; sorbitol; galactitol; iditol; volemitol; fucitol; inositol; a glycylglycitol, and combinations thereof.

22. The method of claim 17, wherein the polyalcohol is selected from the group consisting of: propylene glycol, butane triol and combinations thereof.

23. The method of claim 17, wherein at least one of the sheath fluid, the staining media and the collection media further comprises an antioxidant.

24. The method of claim 23, wherein the antioxidant comprises an antioxidant selected from the group consisting of: vitamin B12; vitamin B12 vitamers; vitamin E; vitamin E vitamers; tocopherol; tocotrienol; α-tocophery; alpha ketoglutarate; derivatives thereof and combinations thereof.

25. The method of claim 17, wherein at least one of the sheath fluid, the staining media, and the collection media further comprises a citrate, citric acid, citric acid monohydrate, or sodium citrate.

26. The method of claim 17, wherein the sheath fluid comprises the cryoprotectant at a vol./vol. or wt./vol. concentration between about 0.1% and about 6%.

27. The method of claim 17, wherein the sheath fluid comprises the cryoprotectant at a vol./vol. or wt./vol. concentration between about 0.1% and about 2%; between about 2% and about 4%; between about 4% and about 6%; between about 1% and about 2%; between about 2% and about 3%; between about 3% and about 4%; between about 4% and about 5%; between about 5% and about 6%; between about 2% and about 6%; or between about 3% and about 5%.

28. The method of claim 17, wherein the staining media comprises the cryoprotectant at a vol./vol. or wt./vol. concentration between about 0.1% and about 1%; between about 1% and about 2%; between about 2% and about 3%; between about 3% and about 4%; between about 2% and about 4%; or between about 1.5% and about 3%.

29. The method of claim 17, wherein the collection media comprises the cryoprotectant at a vol./vol. or wt./vol. concentration between about 1% and about 2%; between about 2% and about 4%; between about 4% and about 6%; between about 3% and about 5%; or between about 3.5% and about 5.5%; or at about 4.5%.

30. The method of claim 17, wherein the sheath fluid comprises a saline buffered with phosphates, TRIS citrate, or HEPES.

* * * * *